(12) United States Patent
Mueller et al.

(10) Patent No.: US 8,962,803 B2
(45) Date of Patent: Feb. 24, 2015

(54) ANTIBODIES AGAINST THE RGM A PROTEIN AND USES THEREOF

(75) Inventors: Bernhard K. Mueller, Neustadt (DE); Martin Schmidt, Bensheim (DE); Eve Barlow, Wellesley, MA (US); Mary Leddy, North Attleborough, MA (US); Chung-Ming Hsieh, Newton, MA (US); Philip Bardwell, Boston, MA (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 181 days.

(21) Appl. No.: 12/389,927

(22) Filed: Feb. 20, 2009

(65) Prior Publication Data

US 2010/0028340 A1 Feb. 4, 2010

Related U.S. Application Data

(60) Provisional application No. 61/032,707, filed on Feb. 29, 2008, provisional application No. 61/090,743, filed on Aug. 21, 2008.

(51) Int. Cl.
C07K 16/00 (2006.01)

(52) U.S. Cl.
USPC .................................. 530/387.1; 424/133.1

(58) Field of Classification Search
None
See application file for complete search history.

(56) References Cited

U.S. PATENT DOCUMENTS

| | | | |
|---|---|---|---|
| 4,394,448 A | 7/1983 | Szoka, Jr. et al. |
| 4,399,216 A | 8/1983 | Axel et al. |
| 4,510,245 A | 4/1985 | Cousens et al. |
| 4,526,938 A | 7/1985 | Churchill et al. |
| 4,554,101 A | 11/1985 | Hopp |
| 4,634,665 A | 1/1987 | Axel et al. |
| 4,704,692 A | 11/1987 | Ladner |
| 4,816,397 A | 3/1989 | Boss et al. |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,968,615 A | 11/1990 | Koszinowski et al. |
| 4,980,286 A | 12/1990 | Morgan et al. |
| 5,006,309 A | 4/1991 | Khalil et al. |
| 5,063,081 A | 11/1991 | Cozzette et al. |
| 5,089,424 A | 2/1992 | Khalil et al. |
| 5,128,326 A | 7/1992 | Balazs et al. |
| 5,135,875 A | 8/1992 | Meucci et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,241,070 A | 8/1993 | Law et al. |
| 5,258,498 A | 11/1993 | Huston et al. |
| 5,290,540 A | 3/1994 | Prince et al. |
| 5,294,404 A | 3/1994 | Grandone et al. |
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,490 A | 6/1996 | Erickson et al. |
| 5,525,524 A | 6/1996 | Buechler et al. |
| 5,530,101 A * | 6/1996 | Queen et al. ............... 530/387.3 |
| 5,541,109 A | 7/1996 | Searfoss, III et al. |
| 5,543,524 A | 8/1996 | Mattingly et al. |
| 5,545,806 A | 8/1996 | Lonberg et al. |
| 5,565,332 A | 10/1996 | Hoogenboom et al. |
| 5,565,352 A | 10/1996 | Hochstrasser et al. |
| 5,565,362 A | 10/1996 | Rosen |
| 5,569,825 A | 10/1996 | Lonberg et al. |
| 5,571,698 A | 11/1996 | Ladner et al. |
| 5,573,904 A | 11/1996 | Mattingly |
| 5,580,717 A | 12/1996 | Dower et al. |
| 5,580,859 A | 12/1996 | Felgner et al. |
| 5,585,089 A | 12/1996 | Queen et al. |
| 5,593,896 A | 1/1997 | Adamczyk et al. |
| 5,624,821 A | 4/1997 | Winter et al. |
| 5,625,126 A | 4/1997 | Lonberg et al. |

(Continued)

FOREIGN PATENT DOCUMENTS

| | | |
|---|---|---|
| DE | 102008014880 | 9/2009 |
| EP | 239400 | 9/1987 |

(Continued)

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*

(Continued)

Primary Examiner — Laura B Goddard
Assistant Examiner — Meera Natarajan
(74) Attorney, Agent, or Firm — Lisa V. Mueller; Michael Best & Friedrich LLP

(57) ABSTRACT

The subject invention relates to isolated proteins, particularly monoclonal antibodies, which bind and neutralize RGM A protein. Specifically, these antibodies have the ability to inhibit the binding of RGM A to its receptor and/or coreceptors. These antibodies or portions thereof of the invention are useful for detecting RGM A and for inhibiting RGM A activity, for example in a human suffering from a disorder including but nor limited to multiple sclerosis, mammalian brain trauma, spinal cord injury, stroke, neurodegenerative diseases, and schizophrenia.

69 Claims, 11 Drawing Sheets

(56) References Cited

U.S. PATENT DOCUMENTS

| | | |
|---|---|---|
| 5,627,052 A | 5/1997 | Schrader |
| 5,633,425 A | 5/1997 | Lonberg et al. |
| 5,648,260 A | 7/1997 | Winter et al. |
| 5,658,727 A | 8/1997 | Barbas et al. |
| 5,661,016 A | 8/1997 | Lonberg et al. |
| 5,679,377 A | 10/1997 | Bernstein et al. |
| 5,679,526 A | 10/1997 | Buechler et al. |
| 5,693,762 A | 12/1997 | Queen et al. |
| 5,698,426 A | 12/1997 | Huse |
| 5,714,350 A | 2/1998 | Co et al. |
| 5,714,352 A | 2/1998 | Jakobovits et al. |
| 5,723,323 A | 3/1998 | Kauffman et al. |
| 5,733,743 A | 3/1998 | Johnson et al. |
| 5,747,262 A | 5/1998 | Hinck et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,780,225 A | 7/1998 | Wigler et al. |
| 5,783,699 A | 7/1998 | Mattingly et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,837,500 A | 11/1998 | Ladner et al. |
| 5,849,992 A | 12/1998 | Meade et al. |
| 5,851,776 A | 12/1998 | Valkirs |
| 5,855,913 A | 1/1999 | Hanes et al. |
| 5,874,064 A | 2/1999 | Edwards et al. |
| 5,877,397 A | 3/1999 | Lonberg et al. |
| 5,885,527 A | 3/1999 | Buechler et al. |
| 5,885,793 A | 3/1999 | Griffiths et al. |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Lloyd et al. |
| 5,939,272 A | 8/1999 | Buechler et al. |
| 5,939,598 A | 8/1999 | Kucherlapati et al. |
| 5,947,124 A | 9/1999 | Buechler et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,994,619 A | 11/1999 | Stice et al. |
| 5,998,209 A | 12/1999 | Jokobovits et al. |
| 6,004,746 A | 12/1999 | Brent et al. |
| 6,017,517 A | 1/2000 | Park |
| 6,019,944 A | 2/2000 | Buechler et al. |
| 6,019,968 A | 2/2000 | Platz et al. |
| 6,075,181 A | 6/2000 | Kucherlapati et al. |
| 6,087,326 A | 7/2000 | Hinck et al. |
| 6,091,001 A | 7/2000 | Jakobovits et al. |
| 6,096,311 A | 8/2000 | Fanger et al. |
| 6,111,166 A | 8/2000 | van de Winkel |
| 6,113,855 A | 9/2000 | Buechler |
| 6,114,598 A | 9/2000 | Kucherlapati et al. |
| 6,130,364 A | 10/2000 | Jakobovits et al. |
| 6,143,576 A | 11/2000 | Buechler |
| 6,180,370 B1 | 1/2001 | Queen et al. |
| 6,204,023 B1 | 3/2001 | Robinson et al. |
| 6,270,765 B1 | 8/2001 | Deo et al. |
| 6,303,755 B1 | 10/2001 | Deo et al. |
| 6,350,861 B1 | 2/2002 | Co et al. |
| 6,365,116 B1 | 4/2002 | Barham et al. |
| 6,410,690 B1 | 6/2002 | Deo et al. |
| 6,632,926 B1 | 10/2003 | Chen et al. |
| 6,660,843 B1 | 12/2003 | Feige et al. |
| 6,682,928 B2 | 1/2004 | Keler et al. |
| 6,699,658 B1 | 3/2004 | Wittrup et al. |
| 6,864,239 B2 | 3/2005 | Peri et al. |
| 6,890,763 B2 | 5/2005 | Jackowski et al. |
| 6,914,128 B1 | 7/2005 | Salfeld et al. |
| 6,925,389 B2 | 8/2005 | Hitt et al. |
| 6,984,720 B1 | 1/2006 | Korman et al. |
| 6,989,100 B2 | 1/2006 | Norton |
| 7,094,761 B2 | 8/2006 | Peri et al. |
| 7,265,212 B2 | 9/2007 | Babcook et al. |
| 7,288,253 B2 | 10/2007 | Roskos et al. |
| 7,368,531 B2 | 5/2008 | Rosen et al. |
| 7,439,063 B2 | 10/2008 | Digicayloglu et al. |
| 7,498,034 B2 | 3/2009 | Bicknell et al. |
| 7,504,225 B2 | 3/2009 | Ring et al. |
| 7,524,492 B2 | 4/2009 | Sharma |
| 7,582,440 B2 | 9/2009 | Bicknell et al. |
| 7,612,181 B2 | 11/2009 | Wu et al. |
| 7,612,183 B2 | 11/2009 | Ellis et al. |
| 7,659,370 B2 | 2/2010 | Woolf et al. |
| 7,696,155 B2 | 4/2010 | Woolf et al. |
| 7,696,156 B2 | 4/2010 | Woolf et al. |
| 7,771,952 B2 | 8/2010 | Strittmatter et al. |
| 7,951,369 B2 | 5/2011 | Goldenberg et al. |
| 7,968,091 B2 | 6/2011 | Woolf et al. |
| 7,968,520 B2 | 6/2011 | Woolf et al. |
| 7,981,415 B2 | 7/2011 | Staunton et al. |
| 7,981,416 B2 | 7/2011 | Hardy et al. |
| 7,981,420 B2 | 7/2011 | Mueller et al. |
| 7,999,072 B2 | 8/2011 | PlouÉT et al. |
| 8,017,115 B2 | 9/2011 | Irving et al. |
| 2002/0110804 A1 | 8/2002 | Stanton et al. |
| 2002/0136725 A1 | 9/2002 | Blackburn et al. |
| 2002/0137134 A1 | 9/2002 | Gerngross |
| 2003/0087394 A1 | 5/2003 | Sharma |
| 2003/0170881 A1 | 9/2003 | Davis et al. |
| 2003/0186374 A1 | 10/2003 | Hufton et al. |
| 2003/0212001 A1 | 11/2003 | Peri et al. |
| 2003/0235584 A1 | 12/2003 | Kloetzer et al. |
| 2004/0009491 A1 | 1/2004 | Birse et al. |
| 2004/0018577 A1 | 1/2004 | Emerson Campbell et al. |
| 2004/0018590 A1 | 1/2004 | Gerngross et al. |
| 2004/0038292 A1 | 2/2004 | Burslem et al. |
| 2004/0071711 A1 | 4/2004 | Bicknell et al. |
| 2004/0092444 A1 | 5/2004 | Digicaylioglu et al. |
| 2004/0102376 A1 | 5/2004 | Mueller et al. |
| 2005/0013809 A1 | 1/2005 | Owens et al. |
| 2005/0042664 A1 | 2/2005 | Wu et al. |
| 2005/0054078 A1 | 3/2005 | Miller et al. |
| 2005/0058649 A1 | 3/2005 | Landes et al. |
| 2005/0059604 A1 | 3/2005 | Peri et al. |
| 2005/0142137 A1 | 6/2005 | Gallo et al. |
| 2005/0197284 A9 | 9/2005 | Digicaylioglu et al. |
| 2006/0003391 A1 | 1/2006 | Ring et al. |
| 2006/0063208 A1 | 3/2006 | Woolf et al. |
| 2006/0104968 A1 | 5/2006 | Bookbinder et al. |
| 2006/0160164 A1 | 7/2006 | Miller et al. |
| 2006/0252101 A1 | 11/2006 | Strittmatter et al. |
| 2006/0292613 A1 | 12/2006 | Peri et al. |
| 2007/0025913 A1 | 2/2007 | Bicknell et al. |
| 2007/0071675 A1 | 3/2007 | Wu et al. |
| 2007/0122491 A1 | 5/2007 | Lyons et al. |
| 2007/0155687 A1 | 7/2007 | Lyons et al. |
| 2007/0166711 A1 | 7/2007 | Samuels et al. |
| 2007/0253946 A1 | 11/2007 | Yamashita et al. |
| 2008/0004255 A1 | 1/2008 | Lyons et al. |
| 2008/0008692 A1 | 1/2008 | Lyons et al. |
| 2008/0020401 A1 | 1/2008 | Grenier et al. |
| 2008/0081337 A1 | 4/2008 | Sharma |
| 2008/0105705 A1 | 5/2008 | Schmidt |
| 2008/0135582 A1 | 6/2008 | Schmidt |
| 2008/0145359 A1 | 6/2008 | Bicknell et al. |
| 2008/0160034 A1 | 7/2008 | Brennan et al. |
| 2008/0181897 A1 | 7/2008 | Ni et al. |
| 2008/0213791 A1 | 9/2008 | Freije et al. |

(56) References Cited

U.S. PATENT DOCUMENTS

| | | |
|---|---|---|
| 2008/0219924 A1 | 9/2008 | Bicknell et al. |
| 2008/0248493 A1 | 10/2008 | Mattingly et al. |
| 2008/0274045 A9 | 11/2008 | Bicknell et al. |
| 2008/0279859 A1 | 11/2008 | Mezler et al. |
| 2009/0012628 A1 | 1/2009 | Shortkroff et al. |
| 2009/0017039 A1 | 1/2009 | Mi et al. |
| 2009/0028852 A1 | 1/2009 | Herrera et al. |
| 2009/0054984 A1 | 2/2009 | Shortkroff et al. |
| 2009/0069903 A1 | 3/2009 | Shortkroff et al. |
| 2009/0093409 A1 | 4/2009 | Digicaylioglu et al. |
| 2009/0123413 A1 | 5/2009 | Hardy et al. |
| 2009/0191118 A1 | 7/2009 | Young et al. |
| 2009/0191572 A1 | 7/2009 | Bicknell et al. |
| 2009/0220588 A1 | 9/2009 | Edelman et al. |
| 2009/0220589 A1 | 9/2009 | Trieu et al. |
| 2009/0227502 A1 | 9/2009 | Goldberg et al. |
| 2009/0252742 A1 | 10/2009 | Bergstein |
| 2009/0252748 A1 | 10/2009 | Mi et al. |
| 2009/0269356 A1 | 10/2009 | Epstein et al. |
| 2009/0280116 A1 | 11/2009 | Smith et al. |
| 2009/0297527 A1 | 12/2009 | Muller et al. |
| 2009/0304693 A1 | 12/2009 | Ghayur et al. |
| 2009/0311253 A1 | 12/2009 | Ghayur et al. |
| 2010/0004431 A1 | 1/2010 | Bernett et al. |
| 2010/0015665 A1 | 1/2010 | Latham et al. |
| 2010/0028340 A1 | 2/2010 | Mueller et al. |
| 2010/0036091 A1 | 2/2010 | Robinson et al. |
| 2010/0036502 A1 | 2/2010 | Svrluga et al. |
| 2010/0041139 A1 | 2/2010 | Goldberg |
| 2010/0047239 A1 | 2/2010 | Wu et al. |
| 2010/0068803 A1 | 3/2010 | Goldberg |
| 2010/0099103 A1 | 4/2010 | Hsieh et al. |
| 2010/0105569 A1 | 4/2010 | Hsieh et al. |
| 2010/0111967 A1 | 5/2010 | Baehner et al. |
| 2010/0150918 A1 | 6/2010 | Kufer et al. |
| 2010/0168393 A1 | 7/2010 | Clube et al. |
| 2010/0183588 A1 | 7/2010 | Plouet et al. |
| 2010/0183608 A1 | 7/2010 | Woolf et al. |
| 2010/0183631 A1 | 7/2010 | Rothe et al. |
| 2010/0184033 A1 | 7/2010 | West et al. |
| 2010/0249039 A1 | 9/2010 | Zangemeister-Wittke et al. |
| 2010/0254979 A1 | 10/2010 | Staunton et al. |
| 2010/0286048 A1 | 11/2010 | Rosen et al. |
| 2010/0297121 A1 | 11/2010 | Mi |
| 2010/0310573 A1 | 12/2010 | Nakagawa et al. |
| 2010/0322948 A1 | 12/2010 | Mueller et al. |
| 2010/0330076 A1 | 12/2010 | Georgiou et al. |
| 2011/0003971 A1 | 1/2011 | Strittmatter et al. |
| 2011/0020221 A1 | 1/2011 | Berman et al. |
| 2011/0070156 A1 | 3/2011 | Govindan et al. |
| 2011/0110852 A1 | 5/2011 | Miller et al. |
| 2011/0110936 A1 | 5/2011 | Nam et al. |
| 2011/0112280 A1 | 5/2011 | Mueller et al. |
| 2011/0117085 A1 | 5/2011 | Rotem-Yehudar et al. |
| 2011/0135657 A1 | 6/2011 | Hu et al. |
| 2011/0135664 A1 | 6/2011 | Mueller |
| 2011/0171126 A1 | 7/2011 | Burton et al. |
| 2011/0183924 A1 | 7/2011 | Mintz et al. |
| 2011/0195021 A1 | 8/2011 | Deckert et al. |
| 2011/0206671 A1 | 8/2011 | Yamashita et al. |
| 2011/0212107 A1 | 9/2011 | Goldberg et al. |
| 2011/0243841 A1 | 10/2011 | Chang et al. |
| 2011/0263827 A1 | 10/2011 | Ghayur et al. |
| 2011/0293526 A1 | 12/2011 | Plikus et al. |

FOREIGN PATENT DOCUMENTS

| | | |
|---|---|---|
| EP | 321201 A2 | 6/1989 |
| EP | 360257 A2 | 3/1990 |
| EP | 368684 | 5/1990 |
| EP | 404097 | 12/1990 |
| EP | 0471293 | 2/1992 |
| EP | 519596 | 12/1992 |
| EP | 229246 B1 | 8/1993 |
| EP | 592106 | 4/1994 |
| EP | 239400 B1 | 8/1994 |
| EP | 291533 B1 | 10/1995 |
| EP | 0963376 A1 | 12/1999 |
| EP | 1176195 A1 | 1/2002 |
| EP | 1347046 | 9/2003 |
| EP | 1396543 | 3/2004 |
| EP | 1440981 | 7/2004 |
| EP | 1677113 | 7/2006 |
| EP | 1733737 | 12/2006 |
| EP | 2033971 | 3/2009 |
| EP | 2260055 | 12/2010 |
| GB | 8901334 | 5/1990 |
| GB | 9101134 | 1/1992 |
| GB | 9201755 | 4/1993 |
| GB | 2456390 | 7/2009 |
| JP | 2010065045 | 3/2010 |
| JP | 2011512806 A | 4/2011 |
| JP | 4986370 | 7/2012 |
| KR | 20080058021 | 6/2008 |
| WO | 90/02809 | 3/1990 |
| WO | 90/05144 | 5/1990 |
| WO | 9005370 A1 | 5/1990 |
| WO | 9014424 A1 | 11/1990 |
| WO | 9014430 A1 | 11/1990 |
| WO | 9014443 A1 | 11/1990 |
| WO | 91/05548 | 5/1991 |
| WO | 9105939 A1 | 5/1991 |
| WO | 91/09967 | 7/1991 |
| WO | 91/10737 | 7/1991 |
| WO | 91/10741 | 7/1991 |
| WO | 9109630 A1 | 7/1991 |
| WO | 91/17271 | 11/1991 |
| WO | 92/01047 | 1/1992 |
| WO | 92/02551 | 2/1992 |
| WO | 92/09690 | 6/1992 |
| WO | 92/15679 | 9/1992 |
| WO | 92/18619 | 10/1992 |
| WO | 9218619 A1 | 10/1992 |
| WO | 92/19244 | 11/1992 |
| WO | 92/20791 | 11/1992 |
| WO | 92/22324 | 12/1992 |
| WO | 93/01288 | 1/1993 |
| WO | 9306213 A1 | 4/1993 |
| WO | 93/11236 | 6/1993 |
| WO | 9401234 A2 | 1/1994 |
| WO | 94/02602 | 2/1994 |
| WO | 94/29469 | 12/1994 |
| WO | 9429469 A2 | 12/1994 |
| WO | 95/15982 | 6/1995 |
| WO | 95/20401 | 8/1995 |
| WO | 96/13518 | 5/1996 |
| WO | 9618978 A1 | 6/1996 |
| WO | 96/20698 | 7/1996 |
| WO | 96/33735 | 10/1996 |
| WO | 96/34096 | 10/1996 |
| WO | 9633735 A1 | 10/1996 |
| WO | 9634096 A1 | 10/1996 |
| WO | 97/00957 | 1/1997 |
| WO | 9700957 A1 | 1/1997 |
| WO | 97/08320 | 3/1997 |
| WO | 9708320 A1 | 3/1997 |
| WO | 97/29131 | 8/1997 |
| WO | 9729131 A1 | 8/1997 |
| WO | 97/32572 | 9/1997 |
| WO | 9732572 A2 | 9/1997 |
| WO | 97/44013 | 11/1997 |
| WO | 9744013 A1 | 11/1997 |
| WO | 98/16654 | 4/1998 |
| WO | 9816280 A1 | 4/1998 |
| WO | 9816654 A1 | 4/1998 |
| WO | 98/24893 | 6/1998 |
| WO | 98/25947 | 6/1998 |
| WO | 9824893 A2 | 6/1998 |
| WO | 98/31346 | 7/1998 |
| WO | 98/31700 | 7/1998 |
| WO | 9831346 A1 | 7/1998 |
| WO | 9831700 A1 | 7/1998 |
| WO | 98/47343 | 10/1998 |

(56) References Cited

FOREIGN PATENT DOCUMENTS

| | | |
|---|---|---|
| WO | 9847343 A2 | 10/1998 |
| WO | 98/49286 | 11/1998 |
| WO | 98/50433 | 11/1998 |
| WO | 99/01047 | 1/1999 |
| WO | WO9911274 | 3/1999 |
| WO | 99/15154 | 4/1999 |
| WO | 99/20253 | 4/1999 |
| WO | 9920253 A1 | 4/1999 |
| WO | 99/25044 | 5/1999 |
| WO | 99/36569 | 7/1999 |
| WO | 99/45031 | 9/1999 |
| WO | 99/45962 | 9/1999 |
| WO | 99/51741 | 10/1999 |
| WO | 99/53049 | 10/1999 |
| WO | 9954342 A1 | 10/1999 |
| WO | 99/66903 | 12/1999 |
| WO | 00/02911 | 1/2000 |
| WO | 00/05410 | 2/2000 |
| WO | 00/09560 | 2/2000 |
| WO | 00/14271 | 3/2000 |
| WO | 00/17221 | 3/2000 |
| WO | 00/37504 | 6/2000 |
| WO | 0037504 A2 | 6/2000 |
| WO | 00/56772 | 9/2000 |
| WO | 00/73801 | 12/2000 |
| WO | 01/58956 | 8/2001 |
| WO | 0154708 A1 | 8/2001 |
| WO | 01/83525 | 11/2001 |
| WO | 0190304 | 11/2001 |
| WO | 02/02773 | 1/2002 |
| WO | 02/051438 | 7/2002 |
| WO | 02072636 A2 | 9/2002 |
| WO | 03004615 A2 | 1/2003 |
| WO | 03016466 A2 | 2/2003 |
| WO | 03/031462 | 4/2003 |
| WO | 03035835 A2 | 5/2003 |
| WO | 03/089608 | 10/2003 |
| WO | 2004/003150 | 1/2004 |
| WO | 2004005457 | 1/2004 |
| WO | WO 2004/067561 | 8/2004 |
| WO | 2004/078140 | 9/2004 |
| WO | 2004/092405 | 10/2004 |
| WO | WO2005016955 | 2/2005 |
| WO | WO2005061554 | 7/2005 |
| WO | 2005087268 | 9/2005 |
| WO | 2005100584 A2 | 10/2005 |
| WO | 2006054000 | 5/2006 |
| WO | 2006066171 A1 | 6/2006 |
| WO | 2006088972 | 8/2006 |
| WO | WO 2006/094724 | 9/2006 |
| WO | 2006127861 | 11/2006 |
| WO | 2007/024715 | 3/2007 |
| WO | 2007024715 A2 | 3/2007 |
| WO | 2007039256 | 4/2007 |
| WO | 2007058671 | 5/2007 |
| WO | WO 2007/062852 | 6/2007 |
| WO | WO2007062852 A2 | 6/2007 |
| WO | 2007106507 | 9/2007 |
| WO | 2007141258 | 12/2007 |
| WO | 2008013492 | 1/2008 |
| WO | 2008038599 | 4/2008 |
| WO | 2008073919 | 6/2008 |
| WO | 2008073923 | 6/2008 |
| WO | 2008082651 A2 | 7/2008 |
| WO | 2008085797 | 7/2008 |
| WO | 2008087224 | 7/2008 |
| WO | 2009002386 | 12/2008 |
| WO | 2009006543 | 1/2009 |
| WO | 2009026392 | 2/2009 |
| WO | 2009/030500 | 3/2009 |
| WO | 2009092032 | 7/2009 |
| WO | 2009094592 | 7/2009 |
| WO | 2009106356 | 9/2009 |
| WO | WO 2009/106356 | 9/2009 |
| WO | 2009140383 | 11/2009 |
| WO | 2009149185 | 12/2009 |
| WO | 2010006060 | 1/2010 |
| WO | 2010006184 | 1/2010 |
| WO | 2010006189 | 1/2010 |
| WO | 2010007144 | 1/2010 |
| WO | 2010017451 | 2/2010 |
| WO | 2010021696 | 2/2010 |
| WO | 2010044506 A2 | 4/2010 |
| WO | 2010062914 | 6/2010 |
| WO | 2010088688 | 8/2010 |
| WO | 2010105298 | 9/2010 |
| WO | 2010127284 | 11/2010 |
| WO | 2011039289 | 4/2011 |
| WO | 2011039734 | 4/2011 |
| WO | 2011068839 | 6/2011 |
| WO | 2011070045 | 6/2011 |
| WO | 2011071059 | 6/2011 |

OTHER PUBLICATIONS

Padlan et al. PNAS 1989, 86:5938-5942.*
Lamminmaki et al. JBC 2001, 276:36687-36694.*
Hata et al. (JCB, vol. 173, No. 1, pp. 47-58, Apr. 2006).*
Harel, N., et al., "Can Regenerating Axons Recapitulate Developmental Guidance During Recovery from Spinal Cord Injury?," Nature Reviews—Neuroscience, 2006, vol. 7 (8), pp. 603-616.
Schaffar, G., et al., "Lim-only Protein 4 Interacts Directly with the Repulsive Guidance Molecule a Receptor Neogenin," Journal of Neurochemistry, 2008, vol. 107 (2), pp. 418-431.
Suda, M., et al., "Peptides Derived from Repulsive Guidance Molecule Act As Antagonists," Biochemical and Biophysical Research Communications, 2008, vol. 371 (3), pp. 501-504.
Camus, L., et al., "Molecular Evolution of Hemojuvelin and the Repulsive Guidance Molecule Family," Journal of Molecular Evolution, 2007, vol. 107 (2), pp. 428-431.
Braisted, J., et al., Netrin-1 Promotes Thalamic Axon Growth and is Required for Proper Development of the Thalamocortical Projection, J. Neurosci, Aug. 1, 2000, 20(15):5792-5801.
Hata, K., et al., RGMa inhibition promotes axonal growth and recovery after spinal cord injury, J. Cell. Biol., vol. 173, No. 1, Apr. 10, 2006, 47-58.
Keino-Masu, K., et al., Deleted in Colorectal Cancer (DCC) Encodes a Netrin Receptor, Cell, vol. 87, 175-185, Oct. 18, 1996.
Kyoto, A., et al., Synapse formation of the cortico-spinal axons is enhanced by RGMa inhibition after spinal cord injury, Brain Res. (2007), doi: 10.1016/j.brainres.2007.10.038.
Monnier, P., et al., RGM is a repulsive guidance molecule for retinal axons, Nature, vol. 419, 392-395, Sep. 16, 2002.
Mueller, B., et al., The role of repulsive guidance molecules in the embryonic and adult vertebrate central nervous system, Phil. Trans. R. Soc. B 2006 361, 1513-1529, doi: 10.1098/rstb.2006.1888.
Rajagopalan, S., et al., Neogenin mediates the action of repulsive guidance molecule, Nat Cell Biol. vol. 6, No. 8, Aug. 2004, 756-762.
Schwab, J., et al., Central Nervous System Injury-Induced Repulsive Guidance Molecule Expression in the Adult Human Brain, Arch Neurol. vol. 62, Oct. 2005, 1561-1568.
Schwab, J., et al., Spinal cord injury-induced lesional expression of the repulsive guidance molecule (RGM), Eur. J. Neurosci. vol. 21, 1569-1576, 2005.
Yamashita, T. et al., Neogenin and repulsive guidance molecule signaling in the central nervous system, Curr. Opin. Neurobiol., 2006, doi: 10.1016/j.conb.2006.12.001.
Matsunaga, E., et al., "RGM and its receptor neogenin regulate neuronal survival", Nature Cell Biology, Aug. 2004, vol. 6, No. 8, pp. 749-755.
Matsunaga, E., et al., "Repulsive guidance molecule/neogenin: a novel ligand-receptor system playing multiple roles in neural development", Development, Growth & Differentiation, Dec. 2004, vol. 46, No. 6, pp. 481-486.
Rajagopalan, S., et al., "Neogenin mediates the action of repulsive guidance molecule", Nature Cell Biology, Aug. 2004, vol. 6, No. 8, pp. 756-762.
Oldekamp, J., et al., "Expression pattern of the repulsive guidance molecules RGM A, B and C during mouse development", Gene Expression Patters, Elsevier, vol. 4, No. 3, May 2004, pp. 283-288.

(56) References Cited

OTHER PUBLICATIONS

International Search Report from International Patent Application No. WO2007/039256 dated Apr. 3, 2007.
Kyoto, et al., "Synapase formation of the cortico-spinal axons is enhanced by RGMa inhibition after spinal cord injury," Brain Research (2007).
GenomeQuest—Sequence Search Report result Feb. 15 11:32 am dated Feb. 15, 2010.
GenomeQuest—Sequence Search Report result Feb. 15 11:32 am (redo 1) dated Feb. 15, 2010.
FTO RGM-A Sequence search dated Feb. 15, 2010.
RGM-A human isoform 1 NP_001159755 Blast search dated Feb. 15, 2010.
Mueller, B. et al., "RGM, a repulsive guidance molecule, is involved in retinal axon guidance in vitro." Taniguchi Symposia on Brain Sciences, vol. 20 Mol. Basis of Axor Growth & Nerve Pattern Form 1997, pp. 215-229.
Frisen, J. et al., "Ephrin-A5 (AL-1/RAGS) is essential for proper retinal axon guidance and topographic mapping in the mammalian visual system" Neuron, vol. 20, No. 2, Feb. 1998, pp. 235-243.
Tassew, N.G., et al. "Sustained in vivo inhibition of protein domains using single-chain Fv recombinant antibodies and its application to dissect RGMa activity on axonal outgrowth," The Journal of Neuroscience, Jan. 28, 2009, 29 (4): 1126-1131.
Matsunaga, E., et al., "Repulsive guidance molecule plays multiple roles in neuronal differentiation and axon guidance," The Journal of Neuroscience, May 31, 2006, 26(22): 6082-6088.
Fitzgerald, D.P., et al., Neogenin is expressed on neurogenic and gliogenic progenitors in gene expr. pattern (2007).
Fitzgerald, D.P., et al., "Characterization of neogenin-expressing neural progenitor populations and migrating neuroblasts in the embryonic mouse forebrain," Neuroscience (2006).
Muller, B.K., et al., "Chromophore-assisted laser inactivation of a repulsive axonal guidance molecule," Current Biology 1996, vol. 6, No. 11:1497-1502.
Muller, B.K., et al., "In vitro experiments on axonal guidance and growth-cone collapse," J. esp. Biol. 153, 29-46 (1990).
Kuby, 1997, Immunology, Third Edition, pp. 131-134.
Alberts, et al., 1994, Molecular Biology of the Cell, Third Edition, pp. 1216-1220.
Beaud M.L., et al., 2008, BMC Neurosci. 9:5.
Giger, R.J., et al., 2008, Restorative Neuroi. Neurosci. 26: 97-115.
Hunt, D., et al. 2002. J. Neurocytol. 31: 93-120.
Iseda, T., et al., 2008. J. Neurotrauma. 25: 334-349.
Muller, B.K., et al. Curr. Biol. 1996, 6(11): 1497-1502.
Steward, O., et al., 2008. Exp. Neurol. 209: 446-468.
Hata, et al., 2006, Journal of Cell Biology, 173(1): 47-58.
Stokes, et al., "Experimental modeling of human spinal cord injury: a model that crosses the species barrier and mimic the spectrum of human cytopathology," Spinal Cord 40: 101-109, 2002.
Talac, et al., "Animal models of spinal cord injury for evaluation of tissue engineering treatment strategies," Biomaterials 25: 1505-1510, 2004.
Mills, et al., "Strain and model differences in behavior outcomes after spinal cord injury in rat," J. Neurotrauma Aug.; 18(8): 743-756, 2001.
Mautes, et al., "Vascular events after spinal cord injury: contribution to secondary pathogenesis," Phys. Ther. Jul. 2000; 80(7): 673-687.
RGM and Retinal Neuronal Regeneration Search—Jan. 25, 2010.
RGM or RGMA or Neogenin Search—Feb. 16, 2010.
Colombian Opposition, Colombia Application No. 10 117825, dated Aug. 22, 2011, pp. 1-6.
U.S. Appl. No. 60/126,603, filed Mar. 25, 1999, Jochen Salfeld.
Bowie J.U., et al., "Deciphering the Message in Protein Sequences: Tolerance to Amino Acid Substitutions," Science, 1990, vol. 247 (4948), pp. 1306-1310.
Burgess W.H., et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, 1990, vol. 111 (5 Pt 1), pp. 2129-2138.
Frohman E.M., et al., "Modeling Axonal Degeneration within the Anterior Visual System: Implications for Demonstrating Neuroprotection in Multiple Sclerosis," Archives of neurology, 2008, vol. 65 (1), pp. 26-35.
Non-Final Office Action mailed Sep. 18, 2013 for U.S. Appl. No. 13/547,109 filed Jul. 12, 2012.
Non-Final Office Action mailed Aug. 21, 2013 for U.S. Appl. No. 12/963,461 filed Dec. 8, 2010.
Pawson T., et al., "Assembly of Cell Regulatory Systems through Protein Interaction Domains," Science, 2003, vol. 300 (5618), pp. 445-452.
A1L187-Human, Database UniProt; Feb. 6,2007.
Adamczyk et al., Anal. Chim. Acta 579(1): 61-67 (2006).
Adamczyk et al., Bioconjugate Chern. 11: 714-724 (2000).
Adamczyk et al., Bioorg. Med. Chern. Left. 14: 2313-2317 (2004).
Adamczyk et al., Bioorg. Med. Chern. Left. 16: 1324-1328 (2006).
Adamczyk et al., Biorg. Med. Chern. Lett. 14: 3917-3921 (2004).
Adamczyk et al., J. Drg. Chern. 63: 5636-5639 (1998).
Adamczyk et al., Org. Lett. 1: 779-781 (1999).
Adamczyk et al., Org. Left. 5: 3779-3782 (2003).
Adamczyk et al., Tetrahedron 55: 10899-10914 (1999).
Albert, S.E. et al. (1997) J. Immunol 159:1393-1403.
Amann et al., (1988) Gene 69:301-315.
Ames et al., J. Immunol Methods 184:177-186 (1995).
Anderson, Science 256 (1992), 808-813.
Ara et al., J. Neurosci.Res. 86: 125-35, 2008.
Arai, K. et al. (1998) J. Immunol Methods 217:79-85.
Atsushi Nagata et al., in Vivo Quantitative Evaluation of the Rat Retinal Nerve Fiber Layer with Optical Coherence Tomography, Investigative Ophthalmology & Visual Science, Jun. 2009, vol. 50, No. 6.
Ausubel et al. (eds.), Current Protocols in Molecular Biology, John Wiley & Sons, NY (1993).
Ausubel, "Short Protocols in Molecular Biology", Green Publishing Associates; and Wiley Interscience, N.Y. (1989).
Ausubel, F.M. et al., Current Protocols in Molecular Biology, Greene Publishing Assoc. And Wiley Interscience (1987).
Babcock, J.S. et al. (1996) Proc. Natl. Acad. Sci. USA 93:7843-7848.
Babitt, J.L., et al., "Bone morphogenetic protein signaling by hemojuvelin regulates hepcidin expression," Nature Genetics, vol. 38, No. 5, May 2006, pp. 531-539.
Babitt, J.L., et al., "Repulsive guidance molecule (RGMa), a Dragon homologue, is a bone morphogenetic protein co-receptor," Journal of Biological Chemistry, vol. 280, No. 33, Aug. 2005. pp. 29820-29827.
Babitt,J.L. et aI., The Journal of Clinical Investigation, 2007, vol. 117, 7, 1933-1939.
Bagnard, Development 125 (1998), 5043-5053.
Baldari et al., (1987) Embo J. 6:229-234.
Barbas et al. (1991) PNAS 88:7978-7982.
Barbas et al., Proc. Nat. Acad. Sci. USA, 91: 3809-3813 (1994).
Becker, D., et al., (1992) "New plant binary vectors with selectable markers located proximal to the left border", Plant Mol. Biol. 20: 1195-1197.
Berrar et al., J. Comput. Biol. (2005) 12 (5),534-544.
Beschorner, Acta Neuropathol. 100 (2000), 377-384.
Better et al., Science 240:1041-1043 (1988).
Bevan, M.W. (1984) "Binary Agrobacterium vectors for plant transformation", Nucl. Acids Res. 12:8711-8721.
Bird et al. (1988) Science 242:423-426.
Blomer, J. Virology 71 (1997) 6641-6649.
Bocher, W.O. et al. (1999) Immunology 96:634-641.
Bodonszky et al., Active esters and resins in peptide synthesis. Chem Ind. Sep. 17, 1966;38:1597-8.
Bombil, F. et al. (1996) Immunobiol. 195:360-375.
Bonhoeffer & Gierer, Trends Neurosci. 7 (1984) 378-381.
Boss, M.A. And Wood, C. R. (1985) Immunology Today 6:12-13.
Braisted et al. J. Neurosci. 20: 5792-5801, 2000.
Brinkman et al., J. Immunol Methods 182:41-50 (1995).
Brown et al. (1980) J Biol Chem 255:4980-83.
Brown et al. (1981) J. Immunol 127:539-46.
Brown, Cell 102 (2000), 77-88.
Buchwald et al., 1980, Surgery 88:507.
Burton et al., Advances in Immunology 57:191-280 (1994).

(56) References Cited

OTHER PUBLICATIONS

Camus, L.M., et al., "Molecular evolution of homojuvelin and the repulsive guidance molecule family," J. Mol. Evol. (2007),65, pp. 68-81.
Caroni and Schwab (Neuron 1, 85-96) 1988.
Caroni, J.Cell Biol. 106 (1988),1291-1288.
Carter et al., Proc. Natl. Acad. Sci. U.S.A. 89:4285 (1992).
Chamat, S. et al. (1999) J. Infect. Diseases 180:268-277.
Charron, J. Biol. Chem 270 (1995), 25739-25745.
Chen, Nature 403 (2000), 434-438.
Cheng et al., Clin. Exp. Med., 11:33-42 (2011).
Cheng, Cell 79 (1994), 157-168.
Chi H. E. Ma et al., The BMP Coreceptor RGMb Promotes While the Endogenous BMP Antagonist Noggin Reduces Neurite Outgrowth and Peripheral Nerve Regeneration by Modulating BMP Signaling, The Journal of Neuroscience, Dec. 14, 2011, 31(50):18391-18400.
Chothia & Lesk, J. Mol. Biol. 196:901-917 (1987).
Chothia et al., J. Mol. Biol. 227:799-817 (1992).
Chothia et al., Nature 342:877-883 (1989).
Christopher J. Severyn et al., Molecular biology, genetics and biochemistry of the repulsive guidance molecule family, Biochem. J. (2009) 422, 393-403.
Clarkson et al. (1991) Nature 352:624-628.
Cleek et al., 1997, "Biodegradable Polymeric Carriers for a bFGF Antibody for Cardiovascular Application," Pro. Int'l. Symp. Control. Rel. Bioact. Mater. 24:853-854.
Colombian Opposition, Colombia Application No. 1 0 117825, dated Aug. 22, 2011, pp. 1-6.
Conrad et al. (1998) Plant Mol. Biol. 38:101-109.
Conrad S. et al., J. Biol. Chem. 282: 16423-16433, 2007.
Corder et al., Science 261: 921 (1993).
Cox, Neuron 4 (1990), 31-7.
Cramer et al. (1999) Cuff. Top. Microbol. Immunol 240:95-118.
David, Science 214 (1981), 931-933.
Davis (1994), Science 266, 816-819.
Divry, P., J. Neurol. Psych. 27: 643-657 (1927).
Drescher, Cell 82 (1995), 359-70.
During et al., 1989, Ann. Neurol. 25:351.
Eduard Resch et al., Long signal peptides of RGMa and DCBLD2 are dissectible into subdomains according to the NtraC model, Mol. BioSyst., 2011, 7, 942-951.
Eren, R. et al. (1998) Immunology 93:154-161.
Famulok, Curro Op. Chem. Biol. 2 (1998), 320-327.
Fanger et al. Immunol Methods 4: 72-81 (1994).
Fazeli, a. et al. Phenotype of mice lacking functional Deleted in colorectal cancer (Dec) gene. Nature 386, 796-804 (1997).
Feldheim et al., Genetic analysis of ephrin-A2 and ephrin-A5 shows their requirement in multiple aspects of retinocollicular mapping. Neuron 25 (2000), 563-74.
Feldheim, Neuron 21 (1998), 1303-1313.
Feys et al., Haematologica 2007, vol. 92, 913-20.
Fishwild, D. M. et al. (1996) Nature Biotechnology 14:845-851.
Flanagan, Ann. Rev. Neurosc. 21 (1998), 309-345.
Foote and Winter 1992, J. Mol. Biol. 224:487-499.
Fournier, a. E., GrandPre, T. & Strittmatter, S. M. Identification of a receptor mediating Nogo-66 inhibition of axonal regeneration. Nature 409, 341-6 (2001).
Fuchs et al. (1991) Bio/Technology 9:1369-1372.
Funaro et al., BMC Biotechnology, 2008(8):85.
Gisin, Hely. Chim. Acta. 56: 1467 (1973).
Goodhill, Neuron 25 (2000), 501-503.
GrandPre, Nature 403 (2000), 439-444.
Gray et al. (1995) J. Imm. Meth. 182:155-163.
Green and Jakobovits, J. Exp. Med., 188: 483-495 (1998).
Green et al. Nature Genetics 7:13-21 (1994).
Heukeshoven et al., Electrophoresis 1988, 9, 60-61.
Ilan, E. et al. (1999) Hepatology 29:553-562.
Jin Li et al., Repulsive guidance molecule B (RGMB) plays negative roles in breast cancer by coordinating BMP signaling, Journal of Cellular Biochemistry, 2012.
Kalimo, Greenfield's Neuropathology 6th. Edn. Arnold, London Sydney Auckland (1996), pp. 315-381.
Kato, Brain Pathol., 10 (2000), 137-143.
Kaufman and Sharp, J. Mol. Biol., 159: 601-621 (1982).
Kenny et al. (1995) Bio/Technol. 13:787-790.
Kettleborough et al., Eur. J. Immunol 24:952-958 (1994).
Khachaturian, Arch. Neurol., supra (1985).
Kurjan and Herskowitz (1982) Cell 30:933-943.
Lah et al., Dual roles of the chemorepellent axon guidance molecule RGMa in establishing pioneering axon tracts and neural fate decisions in embryonic vertebrate forebrain, Developmental Neurobiology, 2012.
Logeart-Avramoglou D, et al., An assay for the determination of biologically active bone morphogenetic proteins using cells transfected with an inhibitor of differentiation promoter-luciferase construct. Anal Biochem 2006;349:78-86.
Lucklow and Summers (1989) Virology 170:31-39.
MacCallum J Mol Biol 262(5):732-45 (1996).
Mattingly et al., In Luminescence Biotechnology: Instruments and Applications; Dyke, K. V. Ed.; CRC Press: Boca Raton, pp. 77-105 (2002).
Mendez, M. J. et al. (1997) Nature Genetics 15:146-156.
Meyerhardt et al. reported in Oncogene (1997) 14, 1129-1136.
Mon et al., Journal of Biological Chemistry 267: 17082 (1992).
Mueller B.K in Molecular Basis of Axon Growth and Nerve Pattern Formation, Edited by H. Fujisawa, Japan Scientific Societies Press, 215-229, 1997.
Muhlhauser, Circ. Res. 77 (1995), 1077-1086.
Mullinax et al., BioTechniques 12(6):864-869 (1992).
Murphy, W.J. et al. (1996) Semin. Immunol 8.233-241.
Murphy, W.J. et al. (1999) Clin. Immunol 90:22-27.
Narang, S.A. (1983) Tetrahedron 39:3.
Nemeth, E. et. al. (2003) Blood:101:7,2461.
Persic et al., Gene 187: 9-18 (1997).
Postler, Glia 19 (1997), 27-34.
Powell et al. (1990) Biotechnol. 8:333-337.
Presta et al., J. Immunol 151:2623 (1993).
Reisner, Yand Dagan, S. (1998) Trends Biotechnol. 16:242-246.
Robinson, ed., Sustained and Controlled Release Drug Delivery Systems, Marcel Dekker, Inc., New York, 1978.
Roes, J. et al. (1995) J. Immunol Methods 183:231-237.
Sandhu et al. (1996) Crit. Rev. Biotechnol. 16:95-118.
Sawai et al., Am. J. Reprod. Immunol , 34:26-34 (1995).
Schultz et al. (1987) Gene 54:113-123.
Smolen and Ball (eds.), Controlled Drug Bioavailability, Drug Product Design and Performance, Wiley, New York (1984).
Sperry, Proc. Natl. Acad. Sci. USA 50 (1963), 703-710.
Sven Schnichels et al., RGMA and neogenin protein expression are influenced by lens injury following optic nerve crush in the rat retina, Graefes Arch Clin Exp Ophthalmol, 2011.
Takahide Itokazu et al., Identification of the Neogenin-Binding Site on the Repulsive Guidance Molecule A, PLoS One, Mar. 2012, vol. 7, Issue 3.
Takekazu Kubo et al., Crosstalk Between the Immune and Central Nervous Systems with Special Reference to Drug Development, 2011.
Tanelian, Nat. Med. 3 (1997), 1398-1401.
Terry et al., J. Neuropathol. Exp. Neurol 46: 262 (1987).
Urist et al., Prog. Clin. Biol. Res. 1985, vol. 187: 77-96.
Verma, Nature 389 (1997), 239-242.
Voet, Voet, Biochemistry, Second Edition, p. 1361, John Wiley & Sons, Inc., 1995.
Wahl, J. Cell Biol. 149(2) (2000), 263-70.
Weinstein, D. et. al. (2002) Blood:100:10, 3776.
Wen et al. (1987) J. Immunol 17:887-892.
Wilm & Mann, Anal. Chem. 68 (1996), 1-8.
Wisniewski et al., Zimmerman, H. M. (ed.): Progress in Neuropathology (Grune and Stratton, N.Y. 1973) vol. 2, pp. 1-26.
Wu, C., et al., Nature Biotechnology, 25(11): 1290-1297 (2007).
Yang, X.D. et al. (1999) J. Leukoc. Biol. 66:401-410.
Yelton et al., J. Immunol , 155: 1994-2004 (1995).

(56) References Cited

OTHER PUBLICATIONS

Yin Xia et al., Dragon (Repulsive Guidance Molecule b) Inhibits IL-6 Expression in Macrophages, J Immunol 2011;186;1369-1376; Prepublished online Dec. 27, 2010.
Zapata et al. (1995) Protein Eng. 8(10): 1057-1062.
PCT/US2003/20147 International Search Report dated Jun. 21, 2004 (1 page).
PCT/EP2006/009497 International Search Report dated May 14, 2007 (6 pages).
Non-Final Office Action mailed Nov. 22, 2013 for U.S. Appl. No. 14/033,707 filed Sep. 23, 2013.
Final Office Action mailed Jan. 16, 2014 for U.S. Appl. No. 12/677,054 filed Jan. 25, 2013.
Brinks H., et al., "The Repulsive Guidance Molecule RGMa is Involved in the Formation of Afferent Connections in the Dentate Gyrus," The Journal of Neuroscience, 2004, vol. 24 (15), pp. 3862-3869.
Casadevall A., et al., "Immunoglobulin Isotype Influences Affinity and Specificity," Proceedings of the National Academy of Sciences, 2012, vol. 109 (31), pp. 12272-12273.
Final Office Action mailed Mar. 12, 2014 for U.S. Appl. No. 12/963,461 filed Dec. 8, 2010.
Hermanson G.T., "Antibody Modification and Conjugation," in: Bioconjugate Techniques, 1996, Chapter 10, Academic Press, pp. 456-493.
Office Action mailed Feb. 13, 2014 for U.S. Appl. No. 11/992,720 filed May 16, 2009.
Singer M., et al. Genes and Genomes, A Changing Perspective, University science Books, California, 1991, pp. 68-69.
Genbank Accession No. CAK97872.1 Jun. 30, 2006.
Non-Final Office Action mailed Jul. 19, 2013 for U.S. Appl. No. 13/493,005 filed Jun. 11, 2012.
U.S. Appl. No. 61/142,048, filed Dec. 31, 2008, Collier et al.
U.S. Appl. No. 60/126,603, Jochen Salfeld, filed Mar. 25, 1999.
U.S. Appl. No. 61/142,048, Collier et al., filed Dec. 31, 2008.
Koeberle, P.D., et al., "The repulsive guidance molecule, RGMa, promotes retinal ganglion cell survival in vitro and in vivo," Neuroscience. 169 (2010), pp. 495-504.
Mattingly, J. Biolumin. Chemilumin. 6:107-114 (1991).
Yamashita et al., Current Opinion in Neurobiology (2007) 17: 1-6.
Hamilton R.G., "Molecular Engineering: Applications to the Clinical Laboratory," Clinical Chemistry, 1993, vol. 39 (9), pp. 1988-1997.
Notice of Allowance mailed Oct. 31, 2013 for U.S. Appl. No. 13/493,005, filed Jun. 11, 2012.
Osada N., et al., EMBL Accession No. AB046024, Oct. 1, 2000.
Winter G., et al., "Humanized Antibodies," Immunology Today, 1993, vol. 14 (6), pp. 243-246.
G. Galfre et al. (1977) Nature 266:550-52.
Gallo, M.L. et al.(2000) Eur. J. Immunol 30:534-540.
Ganz, T., Blood, 117:4425-33, 2011.
Garrad et al. (1991) Bio/Technology 9:1373-1377.
Gavilondo JV., and Larrick J.W. (2000) BioTechniques 29:128-145.
Geddes, Front Neuroendocrinol. 20 (1999), 296-316.
Geddes, Nat. Med. 3 (1997), 1402-1404.
Gefter et al. (1977) Somatic Cell Genet., 3:231-36.
Geisbrecht, B.V., et al. Netrin binds discrete subdomains of DCC and UNC5 and mediates interactions between DCC and heparin. J Biol Chem (2003).
GenBank NM_008684.
GenBank NM_020211.
GenBank NP_001012779.
GenBank NP_064596.1.
GenBank NP_998818.1.
GenBank NT_039474.
Gheith, M., et al., Managing refractory glaucoma with a fixed combination of bimatoprost (0.03%) and timolol (0.5%), Clinical Ophthalmology, 2008, 2(1), pp. 15-19.
Giege, R. et al., Crystallization of Nucleic Acids and Proteins, a Practical Approach, 2nd ed., pp. 20 1-16, Oxford University Press, New York, New York, (1999).
Gierer, Development 101 (1987),479-489.
Gillies et al., (1989) J. Immunol Methods 125:191-202.
Giordano, Nature Medicine 2 (1996), 534-539.
Glenner, G. N. Eng. J. Med. 302: 1283-1333 (1980).
Goeddel, Gene Expression Technology: Methods in Enzymology 185, Academic Press, San Diego, CA (1990).
Gold, Ann. Rev. Biochem. 64 (1995), 763-797.
Goldspiel et al., 1993, Clinical Pharmacy 12:488-505.
Goodman, Annu. Rev. Neurosci. 19 (1996),341-77.
Goodson, in Medical Applications of Controlled Release, supra, vol. 2, pp. 115-138 (1984).
Graham, "Greenfield's Neuropathology." D.I. Graham and P.L. Lantos (eds), 6th. Edn., Edward Arnold, London (1996), pp. 197-248.
Gram et al. (1992) PNAS 89:3576-3580.
Green, L.L. (1999) J. Immunol Methods 231:11-23.
Griffiths et al. (1993) EMBO J 12:725-734.
Guanghui Zhang et al., Electrical stimulation of olfactory bulb downregulates RGMa expression after ischemia/reperfusion injury in rats, Brain Research Bulletin 86 (2011) 254-261.
Halbrooks, P.J., et al. "Role of RGM coreceptors in bone morphogenetic protein signaling," Journal of Molecular Signaling, vol. 2, Jul. 5, 2007, pp. 1-10.
Hall and Miller, J. Neurosci. Res. 76 18, 2004.
Hammerling, et al., in: Monoclonal Antibodies and T-Cell Hybridomas 563-681 (Elsevier, NY., 1981).
Hanes et al. (1997) Proc. Natl. Acad. Sci. USA, 94:4937-4942.
Hanes et al. (1998) Proc. Natl. Acad. Sci. USA, 95:14130-14135.
Harding, F.A. And Lonberg, N. (1995) Ann. N.Y. Acad. Sci. 764:536-546.
Harlow and Lane "Antibodies, A Laboratory Manual", CSH Press, Cold Spring Harbor, 1988.
Haugland, Handbook of Fluorescent Probes and Research Chemicals (1996).
Hawkins et al. (1992) J Mol Biol 226:889-896.
Hay et al. (1992) Hum Antibod Hybridomas 3:81-85.
Heard, C. et al. (1999) Molec. Med. 5:35-45.
Hentze et. al. (2010) Cell 142:24-38.
Herz, U. et al. (1997) Int. Arch. 30 Allergy Immunol 113:150-152.
Heukeshoven et al., Electrophoresis 1988, 9, 28-32.
Higgins DG, Sharp PM. Fast and sensitive multiple sequence alignments on a microcomputer. Comput Appl. Biosci. 1989 Apr;5(2):151-1.
Highsmith W.E., (2002) Clin. Biochem. 35:425-445.
Holliger, P., et al. (1993) Proc. Natl. Acad. Sci. USA 90:6444-6448.
Hong, K. et al. A ligand-gated association between cytoplasmic domains of UNC5 and DCC family receptors converts netrin-induced growth cone attraction to repulsion. Cell 97, 927-41 (1999).
Hood et al., Adv. Exp. Med. Biol. (1999) 464:127-147.
Hoogenboom et al. (1991) Nuc Acid Res 19:4133-4137.
Hoogenboom H., and Chames P. (2000) Immunology Today 21 :371-378.
Hoogenboom HR., (1997) TIB Tech. 15:62-70.
Horsley, M.B., "Retinal nerve fiber layer thickness in patients receiving chronic anti-vascular endothelial growth factor therapy," American Journal of Ophthalmology, Oct. 2010, vol. 150, No. 4, pp. 558-561.
Howard et al., 1989, J. Neurosurg. 7 1:105.
Huang et al., The Journal of Clinical Investigation (2005), 115, 2087-2091.
Hue et al., Clinical Cancer Research (2001) 7, 2213-2221.
Hurrel, ed., "Monoclonal Hybridoma Antibodies: Techniques and Applications", CRC Press Inc., Boco Raron, FL (1982).
Huse et al. (1989) Science 246:1275-1281.
Huston et al. (1988) Proc. Natl. Acad. Sci. USA 85:5879-5883.
Huston et al., Methods in Enzymology 203:46-88 (1991).
Hutchins, W.A. et al. (1999) Hybridoma 18:121-129.
Ike et al. (1983) Nucleic Acids Res. 11:477.
Isner, Lancet 348 (1996), 370-374.
Itakura et al. (1984) Annu. Rev. Biochem. 53:323-356.
Itakura et al., (1984) Science 198:1056-1063.
Jackson et al., J. Immunol , 154(7): 3310-3319 (1995).
Jacobi, Oncogene 19 (2000), 2052-2059.

(56) References Cited

OTHER PUBLICATIONS

Jaya P. Gnana-Prakasam et al., Iron-mediated retinal degeneration in hemojuvelin knockout mice, Biochemical Journal Immediate Publication. Published on Sep. 26, 2011.
Jens Schmidtmer et al., Isolation and expression pattern of three mouse homologues of chick Rgm, Gene Expression Patterns 4 (2004) 105-110.
Jin Li et al., Potential Prognostic Value of Repulsive Guidance Molecules in Breast Cancer, Anticancer Research 31: 1703-1712 (2011).
Jin Li et al., Repulsive guidance molecules, novel bone morphogenetic protein co-receptors, are key regulators of the growth and aggressiveness of prostate cancer cells, International Journal of Oncology 40: 544-550, 2012.
Johnnson, B., et al. (1991) Anal. Biochem. 198:268-277.
Johnsson, B., et al. (1995) J. Mol. Recognit. 8:125-131.
Joliot et al., 1991, Proc. Natl. Acad. Sci. USA 88:1864-1868.
Jönsson, U. et al. (1991) Biotechniques 11:620-627.
Jönsson, U. et al. (1993) Ann. Biol. Clin. 51:19-26.
Judit Oldekamp et al., Expression pattern of the repulsive guidance molecules RGM A, B and C during mouse development, Gene Expression Patterns 4 (2004) 283-288.
Kabat et al. (1971) Ann. NY Acad, Sci. 190:382-391.
Kabat et al., Sequences of Proteins of Immunological Interest (National Institutes of Health, Bethesda, Md. (1987).
Kabat et al., Sequences of Proteins of Immunological Interest (National Institutes of Health, Bethesda, Md. (1991).
Kaufman et al. (1987) EMBO J. 6:187-193.
Keeling SL, et al., "Mouse Neogenin, a DCC-like molecule, has four splice variants and is expressed widely in the adult mouse and during embryogenesis." Oncogene. Aug. 7. 1997;15(6):691-700.
Kellermann S-A. et al., (2002) Current Opinion in Biotechnology 13:593-597.
Kenneth, in Monoclonal Antibodies: A New Dimension In Biological Analyses, Plenum Publishing Corp., New York, New York (1980).
Kipriyanov, S.M., et al. (1994) Mol. Immunol 31 :1047-1058.
Kipriyanov, S.M., et al. (1995) Human Antibodies and Hybridomas 6:93-101.
Kirschner et al., PNAS 83: 503 (1986).
Kitayama et al., PLoS One, (2011) Vol.6 (9), pp. 1-9.
Klemens Konig et al., The Axonal Guidance Receptor Neogenin Promotes Acute Inflammation, PLoS One, Mar. 2012, vol. 7, Issue 3.
Knappik et al. (2000) J. Mol. Biol. 296:57-86.
Kohler and Milstein, Nature 256 (1975), 494-497.
Kolodkin Cell 75 (1993) 1389-99.
Kontermann and Dubel eds., Antibody Engineering (2001) Springer-Verlag. New York. 790 pp. (ISBN 3-540-41354-5).
Korchynskyi and ten Dijke (1. Biol. Chem. 2002, 277:4883).
Kriegler, Gene Transfer and Expression, A Laboratory Manual, Stockton Press, NY (1990).
Kyte et al., J. Mol. Biol. 157: 105-132 (1982).
Lah et al., Novel roles of the chemorepellent axon guidance molecule RGMa in cell migration and adhesion, Mol. Cell. Biol., Jan. 3, 2012.
Lai et al., Neuroreport 8: 2691-94, 1997.
Lam et al., 1997, "Microencapsulation of Recombinant Humanized Monoclonal Antibody for Local Delivery," Proc. Int'l. Symp. Control Rel. Bioact. Mater. 24:759-760.
Langer 1990, Science 249:1527-1533.
Langer and Wise (eds.), CRC, Medical Applications of Controlled Release, Pres., Boca Raton, Fla. (1984).
Langer et al., Chemical and physical Structure of Polymer as Carriers for Controlled Release of Bioactive Agents: A Review, JMS-Rev. Macromol. Chem. Phys., C23(1), 61-126 (1983).
Leader, K.A. et al. (1992) Immunology 76:229-234.
Leonardo P. Capelli et al., Deletion of the RMGA and CHD2 genes in a child with epilepsy and mental deficiency, European Journal of Medical Genetics, 2012, 1-3.
Lerner (1981) Yale J. Biol. Med., 54:387-402.

Letter dated Dec. 23, 1998 from Bernhard Mueller to Dr. Thomas Hesse reporting on the results of research performed during a sabbatical relating to RGM during Jul. 29, 1998 to Sep. 6, 1998. (English translation).
Levy et al., 1985, Science 228:190.
Lingor et al. J. Neurochem, 2007.
Little M. et al. (2000) Immunology Today 21 :364-370.
Lonberg, N. And Huszar, D. (1995) Int. Rev. Immunol. 13:65-93.
Lonberg, N. et al. (1994) Nature 368:856-859.
Lorelei D. Shoemaker et al., Identification of Differentially Expressed Proteins in Murine Embryonic and Postnatal Cortical Neural Progenitors, PLoS ONE, Feb. 2010, vol. 5, Issue 2.
Lories and Luyten, Cytokine & Growth Factor Reviews 2005, vol. 16, 287-298.
Luciani, N. et. al. (2011) Obesity doi:10.1038/oby.2011.12 Article.
Lunn, M.P. et al. (2000) J. Neurochem. 75:404-412.
MacQuitty, J.J. And Kay, R.M. (1992) Science 257:1188.
Mann et al., J. Neurol. Sci. 89:169.
Mann, Mech. Ageing Dev. 31: 213 (1985).
Marchalonis et al., Adv Exp Med Biol. 484: 13-30 (2001).
Mari Kitayama et al., Activated Microglia Inhibit Axonal Growth through RGMa, PLoS ONE, Sep. 2011 vol. 6 Issue 9.
Marks et al., BioTechnology, 10: 779-783 (1992).
Martinez et al. Brain Res. 894: 1-11, 2001.
Matsuura et al. Biochem Biophys Res Commun., 360: 868-73, 2007.
McCafferty et al., Nature (1990) 348:552-554.
McCapra et al., Photochem. Photobiol. 4: 1111-21 (1965).
McNamara, Nat. Suppl. 399 (1999).
Meier (1999), J. NeuropathoJ. Exp. Neurol. 58, 1099-1110.
Merrifield, J. Am. Chem. Soc. 85: 2149 (1963).
Mey & Thanos, (1992); J. Hirnforschung 33, 673-702.
Milstein et al., Nature, 305(5934): 537-540 (1983).
Mimms et al., Virology 176 (1990), 604-619.
Ming, G. L. et al. cAMP-dependent growth cone guidance by netrin-1. Neuron 19, 1225-35 (1997).
Mirakaj et al., RGM A leukocyte migration inflammation supporting information, PNAS, 2011.
Monschau et al., The EMBO Journal vol. 16 No. 6 pp. 1258-1267, 1997.
Morgan and Anderson, Ann. Rev. Biochem. 62:191-217 (1993).
Morrison, Science 229:1202 (1985).
Mueller, Annu. Rev. Neurosci 22, (1999), 351-88.
Müller et al., Current Biology 1995, vol. 5 no. 11, 1255-1256.
Muller et al., Current Opinion in Genetics and Development 1996, 6:469-474.
Mulligan, Science 260:926- 932 (1993).
Muramatsu et al., Nat. Medicine (2011) 17:488-94.
Nakamoto, Cell 86 (1996), 755-66.
Neuberger et al., 1984, Nature 312:604-608.
Nguyen, H. et al. (1997) Microbiol. Immunol 41 :901-907.
Niederkofler V. et al., J. Neurosci. 24, 808-818, 2004.
Niederkofler, V. et. al. (2005) J. Clin Invest. 115:2180.
Nielsen, Science 254 (1991), 1497-1500.
Ning et al., 1996, "Intratumoral Radioimmunotherapy of a Human Colon Cancer Xenograft Using a Sustained Release Gel," Radiotherapy & Oncology 39:179-189.
Oi et al., BioTechniques 4:214 (1986).
Padlan FASEB J. 9:133-139 (1995).
Padlan, Molecular Immunology 28 (4/5) :489-498 (1991).
Papanikolaou, G. et. al (2005) Blood 105:10,4103-4105.
Papanikolaou, G. et. al. (2004) Nat. Genet. 36:77.
Pauwels, R. (1985). Pharmacokinetics of inhaled drugs. Aerosols in Medicine. Principles, diagnosis and therapy. eds. Moren, F., Newhouse, M. T. & Dolovich, M. B. Amsterdam, New York, Oxford: Elsevier.
Pearson and Lipman, Proc. Natl. Acad, Sci. (USA) 85(8), 1988, 2444-2448.
Picker, Development 126 (1999), 2967-78.
Pietrangelo, J. Hepatology, 54: 173-181 (2011).
Pietta and Marshall, Chem. Comm. 650 (1970).
Polak and Van Noorden, Introduction to Immunocytochemistry, 2nd ed., Springer Verlag, N. Y. (1997).
Poljak, R.J., et al. (1994) Structure 2:1121-1123.

(56) References Cited

OTHER PUBLICATIONS

Puchtler et al., J. Histochem. Cytochem. 10: 365 (1962).
Puschel, Neuron 14 (1995), 941-948.
Raper & Kapfhammer, Neuron 4 (1990), 21-29.
Razavi et al., Luminescence 15: 239-249 (2000).
Reifers, Development 125 (1998), 2381-95.
Remington's Pharmaceutical Sciences and Introduction to Pharmaceutical Dosage Forms, 19th ed., Mack Pub. Co., Easton, Pa. (1995).
Riechmann et al., Nature 332:323 (1988).
Rieko Muramatsu et al., RGMa modulates T cell responses and is involved in autoimmune encephalomyelitis, Nature Medicine, published online Mar. 20, 2011.
Roberts, R.W. And Szostak, J.W. (1997) Proc. Natl. Acad. Sci. USA 94:12297-12302.
Robinson, May 1993, Tibtech 11(5): 155.
Roguska. et al. PNAS 91: 969-973 (1994).
Rosen, C.A., et al., "Therapeutic protein HARMJ38—SEQ ID No. 1853", database EMBL/GENBANK/DDBJ; Jun. 15, 2006.
Routbort, Neuroscience 94 (1999), 755-765.
Ruoshlahti, Annu. Rev. Cell Dev. Biol. 12 (1996), 697-715.
Saeed et al., Arterioscler. Thromb. Vasco Biol., 32 (Feb. 2012), Accepted on Nov. 5, 2011.
Saltzman et al., Biophys. J. 55: 163 (1989).
Samad, T.A. et al., "DRAGON, a bone morphogenetic protein coreceptor," Journal of Biological Chemistry, vol. 280, No. 14, Apr. 2005, pp. 14122-14129.
Sambrook, et al., Molecular Cloning; A Laboratory Manual, 2nd Edition, Cold Spring Harbour Laboratory Press, Cold Spring Harbour, NY (1989).
Santoro, Proc. Natl. Acad. Sci. USA 94 (1997), 4262.
Saudek et al., 1989, N. Engl. J. Med. 321:574.
Schaper, Circ. Res. 79 (1996), 911-919.
Schaper, Current Opinion in Biotechnology 7 (1996), 635-640.
Schier et al., Gene, 169: 147-155 (1995).
Schmidtmer, J. And D. Engelkamp (2004) Gene Exp. Patterns 4:105.
Schnell, Nature 343 (1990) 269-272.
Schnichels, S., et al., "Gene expression of the repulsive guidance moleculeslneogenin in the developing and mature mouse visual system: C57BL16J vs. The glaucoma model DBA/2J," Gene Expression Patterns, 8, (2007), pp. 1-11.
Schwab, Acta Neuropathol. 99 (2000), 609-614.
Seed, B. (1987) Nature 329:840.
Sefton, 1987, CRC Crit. Ref. Biomed. Eng. 14:20.
Serafini, T. et al. Netrin-l is required for commissural axon guidance in the developing vertebrate nervous system. Cell 87, 1001-14 (1996).
Setoguchi et al., Exp. Neurol. 189: 33-44, 2004.
Severyn et al., Biochem. J., 422:393-403 (2009).
Shapiro et al., Crit. Rev. Immunol. 22(3): 183-200 (2002).
Sharp, Genes and Dev. 13 (1999),139-141.
Sherwood et al., Bio/Technology 10: 1446 (1992).
Shu et al., PNAS 90:7995-7999 (1993).
Silhavy, M.L. Berman and L.W. Enquist, Experiments with Gene Fusions, Cold Spring Harbor Laboratory, Cold Spring Harbor, NY (1984).
Skerra et al., Science 240:1038-1040 (1988).
Smith et al., (1983) Mol. Cell Biol. 3:2156-2165.
Smith, D.B. and Johnson, K.S. Pharmacia Biotech Inc (1988) Gene 67:31-40.
Smithson, S.L. et al. (1999) Mol. Immunol 36:113-124.
Song et al., 1995, "Antibody Mediated Lung Targeting of Long-Circulating Emulsions," PDA Journal of Pharmaceutical Science & Technology 50:372-397.
Staerz et al., Nature, 314(6012): 628631 (1985).
Stahl, et al., "Biochemical Characterization of a Putative Axonal Guidance Molecule of the Chick Visual System", Neuron, vol. 5, pp. 735-743 (1990).
Steenbakkers et al. (1994) Molec. Biol. Reports 19:125-134 (1994).
Steinecke, Ribozymes, Methods in Cell Biology 50, Galbraith, eds. Academic Press, Inc. (1995), 449-460.
Stewart and Young in Solid Phase Peptide Syntheses (2nd Ed., Pierce Chemical Company, 1984).
Stoll, Prog. Neurobiol. 56 (1998),149-171.
Streit, Prog. Neurobiol. 57 (1999), 563-581.
Studier et al. Gene Expression Technology: Methods in Enzymology 185, Academic Press, San Diego, California (1990) 60-89.
Studnicka et al., Protein Engineering 7 (6) : 805-814 (1994).
Takeda et al., 1985, Nature 314:452-454.
Tassew, N., et al., "Intraretinal RGMa is involved in retino-tectal mapping," Mol. Cell. Neurosci., 37 (2008), pp. 761-769.
Taylor, L.D. et al. (1992) Nucleic Acids Res. 20:6287-6295.
Tessier-Lavigne, M. & Goodman, C. S. The molecular biology of axon guidance. Science 274, 1123-1133. (1996).
Tolstoshev, Ann. Rev. Pharmacol. Toxicol. 32:573-596, (1993).
Urlaub and Chasin, (1980) Proc. Natl. Acad. Sci. USA 77:4216-4220.
Valbona Mirakaj et al., Repulsive guidance molecule-A (RGM-A) inhibits leukocyte migration and mitigates inflammation, PNAS, Apr. 19, 2011, vol. 108, No. 16, 6555-6560.
Valbona Mirakaj et al., the guidance receptor neogenin promotes pulmonary inflammation during lung injury, The FASEB Journal, Published online Dec. 23, 2011.
van den Hondel, C.A.M.J.J. & Punt, P.J. (1991) Gene transfer systems and vector development for filamentous fungi, in: Applied Molecular Genetics of Fungi, J.F. Peberdy et al., eds, pp. 1-28, Cambridge University Press: Cambridge.
Vielmetier, J., et al. Neogenin, an Avian cell Surface Polypeptide Expressed Terminal Neuronal Differentiation, Is Closely Related to the Human Tumor Suppressor Molecule Deleted in Colorectal Cancer. J. Cell. Bio. Dec. 1994, vol. 127, No. 6, 1-12, 15-17 pp. 2009-2020.
Vielmetter, J., et al., In vitro assay to test differential substrate affinities of growing axons and migratory cells. Exp Brain Res 81, 283-7 (1990).
Wallemacq et al., Evaluation of the New AxSYM Cyclosporine Assay: Comparison with TDx Monoclonal Whole Blood and EMIT Cyclosporine Assays, Clin. Chem. 45: 432-435 (1999).
Walter, Development 101, (1987), 685-96.
Walter, J. Physiol 84 (1990), 104-10.
Walter, J., Henke-Fable, S. & Bonhoeffer, F. Avoidance of posterior tectal membranes by temporal retinal axons. Development 101, 909-13 (1987).
Wang, H., et al., Netrin-3, a mouse homolog of human NTN2L, is highly expressed in sensory ganglia and shows differential binding to netrin receptors. J Neurosci 19,4938-47 (1999).
Wang, Nature Medicine 2 (1996), 714-716.
Ward et al., (1989) Nature 341 :544-546.
Weiss M.D. And Goodnough, L.T., New Engl. J. Med. 352: 1011-1022, 2005.
Wells, High Throughput Bioanalytical Sample Preparation. Methods and Automation Strategies, Elsevier (2003).
Wilbur, W. J. And Lipman, D. J. Proc. Natl. Acad. Sci. USA 80, 726-730 (1983).
Wilm, Nature 379 (1996), 466-9.
Winnaker, From Genes to Clones (Verlagsgesellschaft, Weinheim, Germany 1987).
Wu and Wu, Biotherapy 3:87-95, (1991).
Wu and Wu, J. Biol. Chem. 262:4429-4432 (1987).
Xia, Y., et al., "Localization and action of dragon (repulsive guidance molecule b), a novel bone morphogenetic protein coreceptor, throughout the reproduction axis," Endocrinology, vol. 146, No. 8, Aug. 2005, pp. 3614-3621.
Xia, Yin, et el., "Repulsive guidance molecule RGMa alters utilization of bone morphogenetic protein (BMP) type II receptors by BMP 2 and BMP 4," Journal of Biological Chemistry, vol. 282, No. 25, Jun. 2007, pp. 18129-18140.
Yamashita et al. Curr. Opin. Neurobiol. 17: 29-34, 2007.
Yatscoff et al., Abbott TDx Monoclonal Antibody Assay Evaluated for Measuring Cyclosporine in Whole Blood, Clin. Chem. 36: 1969-1973 (1990).
Yeh et al. (1976) PNAS 76:2927-31.
Yeh et al. (1982) Int. J. Cancer 29:269-75.
Yoshinari, K. And Arai, K. (1998) Hybridoma 17:41-45.

(56) References Cited

OTHER PUBLICATIONS

Yu, T. W. & Bargmann, C. I. Dynamic regulation of axon guidance. Nat Neurosci 4 Suppl, 1169-76 (2001).
PCT/EP2001/015289 International Search Report dated May 13, 2003 (5 pages).
International Search Report from International Patent Application Publication W02009/030500 dated Apr. 3, 2007.
International Search Report for Application No. PCT/EP2009/001437, mailed on Jun. 18, 2009, 3 pages.
Supplemental International Search Report for Application No. PCT/EP2009/001437, mailed on Apr. 8, 2010, 2 pages.
International Search Report and Written Opinion from International Patent Application No. PCT/EP2010/069120, dated Apr. 11, 2011.
International Search Report and Written Opinion from International Patent Application No. PCT/EP2008/007339 dated Sep. 2, 2009 (12 pages).
United States Patent Office Final Rejection for U.S. Appl. No. 12/939,823 dated Dec. 22, 2011 (16 pages).
United States Patent Office Action for U.S. Appl. No. 12/758,445 dated Jan. 13, 2012 (10 pages).
United States Patent Office Action for U.S. Appl. No. 12/992,720 dated Sep. 8, 2011 (11 pages).
United States Patent Office Notice of Allowance for U.S. Appl. No. 12/389,927 dated Jun. 18, 2012 (25 pages).
United States Patent Office Notice of Allowance for U.S. Appl. No. 12/389,927 dated Mar. 2, 2012 (8 pages).
United States Patent Office Final Rejection for U.S. Appl. No. 12/389,927 dated Oct. 28, 2011 (18 pages).
Israeli Patent Office Action for Application No. 207787 dated Aug. 17, 2012 (3 pages).
New Zealand Patent Office Examination Report for Application No. 587198 dated Mar. 11, 2011 (3 pages).
Hungarian Patent Office Written Opinion for Application No. 201005799-0 dated Jun. 8, 2012 (10 pages).
International Search Report and Written Opinion for Application No. PCT/US2013/023277, mailed on Jun. 5, 2013, 21 pages.
Abstracts of the XIIth International Symposium on Bioluminescence and Chemiluminescence to be Held at Robinson College, University of cambridge, England, Apr. 5-9, 2002, Luminescence, 2002, vol. 17, pp. 77-115.
Ausubel, et al., Current Protocols in Molecular Biology, 1993, 6.3.1-6.3.6, 2.10.1-2.10.1- 2.10.16.
Ausubel F.M., et al., eds., Current Protocols in Molecular Biology, 1994-1998, vol. 1, John Wiley & Sons Inc, Table of Contents.
Berzofsky J.A., "Intrinsic and Extrinsic Factors in Protein Antigenic Structure," Science, 1985, vol. 229 (4717), pp. 932-940.
Birse, Ce and Rosen, Ca.: "Humanpolypeptide SEQ ID No. 1934" XP002476351.
Bork P., et al., "Go Hunting in Sequence Databases but Watch out for the Traps," Trends in Genetics, 1996, vol. 12 (10), pp. 425-427.
Bork P., "Powers and Pitfalls in Sequence Analysis: The 70% Hurdle," Genome Research, 2000, vol. 10 (4), pp. 398-400.
Bossers K., et al., "Analysis of Gene Expression in Parkinson's Disease: Possible Involvement of Neurotrophic Support and Axon Guidance in Dopaminergic Cell Death," Brain Pathology, 2009, vol. 19 (1), pp. 91-107.
Brenner S.E., "Errors in Genome Annotation ," Trends in Genetics, 1999, vol. 15 (4), pp. 132-133.
Burtrum D., et al., "A Fully Human Monoclonal Antibody to the Insulin-Like Growth Factor I Receptor Blocks Ligand-Dependent Signaling and Inhibits Human Tumor Growth in Vivo," Cancer Research, 2003, vol. 63 (24), pp. 8912-8921.
Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.
Doerks T., et al., "Protein Annotation: Detective work for Function Prediction," Trends in Genetics, 1998, vol. 14 (6), pp. 248-250.

Elmer L.W., et al., "The Increasing Role of Monoamine Oxidase Type B Inhibitors in Parkinson's Disease Therapy," Expert Opinion on Pharmacotherapy, 2008, vol. 9 (16), pp. 2759-2772.
European Search Report for Application No. EP07115856, mailed on Apr. 15, 2008, 8 pages.
Fitzgerald D.P., et al., "Characterization of Neogenin-expressing Neural Progenitor Populations And Migrating Neuroblasts in the Embryonic Mouse Forebrain," Neuroscience, 2006, vol. 142 (3), pp. 703-716.
Fitzgerald D.P., et al., "Neogenin is Expressed on Neurogenic and Gliogenic Progenitors in the Embryonic and Adult Central Nervous System," Gene Expression Patterns, 2007, vol. 7 (7), pp. 784-792.
Genbank Accession No. AK080819, Mar. 3, 2004.
Genbank Accession No. BCO23870, Feb. 24, 2004.
Genbank Accession No. BCO22603, Jan. 3, 2005.
Genbank Accession No. B1769500, Sep. 25, 2001.
Genbank Accession No. BI818609, Oct. 4, 2001.
Gennaro A.R., ed., Remington: The Science and Practice of Pharmacy, 19th Edition, Mack Publishing, 1995, Table of Contents.
GenomeQuest—Sequence Search Report 'result Feb. 15 11:32 am (redo 1) dated Feb. 15, 2010.
Giege R., et al., "An Introduction to the Crystallogenesis of Biological Macromolecules" in: Crystallization of Nucleic Acids and Proteins, Chapter 1, 2nd Edition, Ducruix A., et al., Eds., Oxford University Press, 1999, pp. 1-16.
Gnana-Prakasam J.P., et al., "Iron-mediated Retinal Degeneration in Haemojuvelin-knockout Mice," The Biochemical Journal, 2012, vol. 441 (2), pp. 599-608.
Goeddel D.V., "Systems for Heterologous Gene Expression," Methods in Enzymology, 1990, vol. 185, pp. 3-7.
Graham D.I., et al., Trauma, Chapter 5, 1996, pp. 197-248.
Hanson L.R., et al., "Intranasal Delivery Bypasses the Blood-Brain Barrier to Target Therapeutic Agents to the Central Nervous System and Treat Neurodegenerative Disease," BMC Neuroscience, 2008, vol. 9 (Suppl 3), pp. S5.
Harlow, et al., "Production of Antibody-Producing Hybridomas in the Rodent Systems," Monoclonal Antibod. And T-Cell Hybrid., pp. 563-681, 1989.
Huang FW., et al., "A Mouse Model of Juvenile Hemochromatosis," The Journal of Clinical Investigation, 2005, vol. 115 (8), pp. 2187-2191.
Isogai, T. et al., "Novel protein sequence#944, XP002476349," .
Jefferis R., "Glycosylation of Recombinant Antibody Therapeutics," Biotechnology Program, 2005, vol. 21 (1), pp. 11-16.
Jones P.T., et al., "Replacing the Complementarity-Determining Regions in a Human Antibody with those from a Mouse," Nature, 1986, vol. 321 (6069), pp. 522-525.
Jost W.H., et al., "Initial Experience with Ropinirole PR (Prolonged Release)," Journal of Neurology, 2008, vol. 255 (Suppl 5), pp. 60-63.
Kabat E.A., et al., in: Sequence of Proteins of Immunological Interest, 4th Edition, 1987, Table of Contents.
Khor S.P., et al., "The Pharmacokinetics and Pharmacodynamics of Levodopa in the Treatment of Parkinson's Disease," Current Clinical Pharmacology, 2007, vol. 2 (3), pp. 234-243.
Knoll B., et al., "Stripe Assay to Examine Axonal Guidance and Cell Migration," Nature Protocols, 2007, vol. 2 (5), pp. 1216-1224.
Koeberle P.D., et al., "The Repulsive Guidance Molecule, RGMa, Promotes Retinal Ganglion Cell Survival in Vitro and in Vivo," Neuroscience, 2010, vol. 169 (1), pp. 495-504.
Liang B.A., et al., "Review of Tissue Plasminogen Activator, Ischemic Stroke, and Potential Legal Issues," Archives of Neurology, 2008, vol. 65 (11), pp. 1429-1433.
Lund J., et al., "Human Fc Gamma RI and Fc Gamma RII Interact with Distinct but Overlapping Sites on Human IgG," Journal of Immunology, 1991, vol. 147 (8), pp. 2657-2662.
Mattingly P.G., "Chemiluminescent 10-Methyl-Acridinium-9(N-Sulphonylcarboxamide) Salts. Synthesis and Kinetics of Light Emission," Journal of Bioluminescence and Chemiluminescence, 1991, vol. 6 (2), pp. 107-114.
Mirakaj et al., Supporting Information [online], Retrieved from the Internet< URL: http://www.pnas.org/cgi/content/short/1015605108>.

(56) References Cited

OTHER PUBLICATIONS

Monahan M.W., et al., "A Rapid Method for the Preparation of Amino Acid Resin Esters for Merrifield Solid-phase Peptide Synthesis," Biopolymers, 1973, vol. 12 (11), pp. 2513-2519.

Ngo J.T., et al., "Computational Complexity, Protein Structure Prediction, and the Levinthal Paradox," 1994, pp. 491-495.

Non-Final Office Action mailed May 27, 2011 for U.S. Appl. No. 11/992,720, filed May 16, 2009.

Office Action mailed Aug. 9, 2012 for Chinese Application No. 200880103451.

Office Action mailed Feb. 2, 2011 for European Application No. 08801915 filed Sep. 8, 2008.

Office Action mailed Feb. 7, 2011 for Canadian Application No. 2542171 filed Jun. 26, 2003.

Office Action mailed Mar. 7, 2012 for Japanese Application No. 2008532684 filed Sep. 29, 2006.

Office Action mailed Jan. 12, 2012 for Mexican Application No. MX2008020005 filed Sep. 29, 2006.

Office Action mailed Apr. 13, 2012 for Canadian Application No. 2542171 filed Jun. 26, 2003.

Office Action mailed Feb. 16, 2012 for Chinese Application No. 2006800363460.

Office Action mailed May 25, 2012 for Chinese Application No. 200880103451 filed Sep. 8, 2008.

Office Action mailed Feb. 28, 2012 for Japanese Application No. 2009250440 filed Oct. 30, 2009.

Opposition mailed Aug. 22, 2011 for Colombian Application No. 10117825 filed Sep. 23, 2010.

Ota, T. et al., "Human protein encoded by full length cDNA clone SEQ ID No. 3867,XP002476348,".

Remington, "The Science and Practice of Pharmacy," Table of Contents, 1995.

Sambrook J., "Expression of Cloned Genes in *Escherichia Coli*" in: Molecular Cloning, 2nd Edition, Cold Spring Harbor Laboratory Press, 1989, Chap. 17.2-17.9.

Samuels, Me., "Hemojuvelin variant(R326X),XP00247635,".

Schier R., et al., "Identification of Functional and Structural Amino-Acid Residues by Parsimonious Mutagenesis," Gene, 1996, vol. 169 (2), 147-155.

Shields R.L., et al., "Lack of Fucose on Human IgG1 N-Linked Oligosaccharide Improves Binding to Human Fcgamma RIII and Antibody-Dependent Cellular Toxicity," The Journal of Biological Chemistry, 2002, vol. 277 (30), pp. 26733-26740.

Sims M.J., et al., "A Humanized CD18 Antibody can Block Function without Cell Destruction," Journal of Immunology, 1993, vol. 151 (4), pp. 2296-2308.

Skolnick J., et al., "From Genes to Protein Structure and Function: Novel Applications of Computational Approaches In The Genomic Era," Trends in Biotechnology, 2000, vol. 18 (1), pp. 34-39.

Smith T.F., et al., "The Challenges of Genome Sequence Annotation or "The Devil Is In The Details"," Nature Biotechnology, 1997, vol. 15 (12), pp. 1222-1223.

Smolen V.F., et al., eds., Controlled Drug Bioavailability: Drug Product Design and Performance, vol. 1, John Wiley & Sons, 1984, Table of Contents.

Sutcliffe J.G., et al., "Antibodies that React with Predetermined Sites on Proteins," Science, 1983, vol. 219 (4585), pp. 660-666.

Umana P., et al., "Engineered Glycoforms of an Antineuroblastoma IgG1 with Optimized Antibody-dependent Cellular Cytotoxic Activity," Nature Biotechnology, 1999, vol. 17 (2), pp. 176-180.

Uniport, "A1L187_HUMAN", Accession No. A1L187, Feb. 6, 2007.

Verhoeyen M., et al., "Reshaping Human Antibodies: Grafting an Antilysozyme Activity," Science, 1988, vol. 239, pp. 1534-1536.

Viewing Sequence(s): 1853 of 2267 for Document # 20060084794, Publication Site for Issued and Published Sequences (PSIPS), SEQ ID No. 1853 [online], Jan. 2011 [Last Modified on Jan. 25, 2011]. Retrieved from the Internet.

Voet D., et al., Biochemistry, Second Edition, John Wiley & Sons, Inc, 1995, Table of Contents.

Wallick S.C., et al., "Glycosylation of a VH Residue of a Monoclonal Antibody against Alpha (1—6) Dextran Increases its Affinity for Antigen," Journal of Experimental Medicine, 1988, vol. 168 (3), pp. 1099-1109.

Wells J.A., "Additivity of Mutational Effects in Proteins," Biochemistry, 1990, vol. 29 (37), pp. 8509-8517.

Wells J.A., et al., "Additivity of Mutational Effects in Proteins," Biochemistry, 1990, vol. 29 (37), pp. 8508-8517.

Wright A., et al., "Antibody Variable Region Glycosylation: Position Effects on Antigen Binding and Carbohydrate Structure," The EMBO Journal, 1991, vol. 10 (10), pp. 2717-2723.

Yamashita T., RGMa Modulates T Cell Responses and is Involved in Autoimmune Encephalomyelitis, Supplementary Information Titles, Nature Medicine.

United States Patent Office Action for U.S. Appl. No. 14/033,707 dated Oct. 30, 2014 (10 pages).

International Written Opinion for Application No. PCT/EP2009/001437, issued Aug. 31, 2010, 7 pages.

\* cited by examiner

A

B

C

ANTIBODIES AGAINST THE RGM A PROTEIN AND USES THEREOF

CROSS-REFERENCE TO RELATED APPLICATIONS

The present application claims priority to U.S. Provisional Application Ser. No. 61/032,707, filed Feb. 29, 2008 and to U.S. Provisional Application Ser. No. 61/090,743, filed Aug. 21, 2008. These applications are hereby incorporated by reference in their entireties.

TECHNICAL FIELD

The present application describes RGM A-binding proteins, particularly monoclonal antibodies, and in particular CDR grafted, humanized versions thereof, which have the ability to bind to RGM A and prevent binding of RGM proteins to RGM A receptor and other RGM A binding proteins, and therefore neutralize the function of RGM A. These antibodies may have utility in the treatment of several states including but not limited to multiple sclerosis, mammalian brain trauma, spinal cord injury, stroke, neurodegenerative diseases, and schizophrenia.

BACKGROUND INFORMATION

Axonal regeneration after injury or after inflammatory attacks or after neurodegenerative diseases within the mammalian central nervous system (CNS) is almost always impossible; the outcome depends on the balance between the intrinsic ability of the nerve fibers in the CNS to re-grow, and the inhibitory factors within the CNS, localized in the microenvironment of the lesion or damage site, which actively prevent the re-growth, and thus the regeneration of the injured fiber tracts.

It has been established that CNS myelin, generated by oligodendrocytes, and the lesional scar are the most relevant non-permissive structures for axonal growth in the early phase of an injury, by causing growth cone collapse and neurite growth inhibition in vitro as well as in vivo, thereby resulting in direct inhibition of axon regrowth. RGM proteins, major inhibitory factors on CNS myelin and scar tissue have been identified (Monnier et al., Nature 419: 392-395, 2002; Schwab et al., Arch. Neurol. 62: 1561-8, 2005a; Schwab et al. Eur. J. Neurosci. 21:1569-76, 2005 b; Hata et al. J. Cell Biol. 173:47-58, 2006; for reviews see: Mueller et al., Philos. Trans. R. Soc. Lond. B Biol. Sci. 361: 1513-29, 2006; Yamashita et al. Curr. Opin. Neurobiol. 17: 29-34, 2007). RGM proteins are up-regulated at damage or lesion sites in humans dying from brain trauma or ischemic insult, (Schwab et al., Arch. Neurol. 62: 1561-8, 2005a) and are up-regulated at lesion sites in rats with spinal cord injury (Schwab et al. Eur. J. Neurosci. 21:1569-76, 2005 b; Hata et al. J. Cell Biol. 173:47-58, 2006 for review see: Mueller et al., Philos. Trans. R. Soc. Lond. B Biol. Sci. 361: 1513-29, 2006; Yamashita et al. Curr. Opin. Neurobiol. 17: 29-34, 2007). In addition first data using clinical samples from Multiple sclerosis patients and healthy persons suggested that human RGM A is up-regulated in cerebrospinal fluid of patients suffering from MS (data not shown).

To evaluate the regeneration-promoting potential of a RGM A-specific polyclonal antibody, the antibodies were administered in a moderate-to-severe model of spinal cord injury, where approximately 60% of the spinal cord at thoracal level 9/10 was transected. The histological examination revealed that such a lesion severed all dorsal and lateral fibers of the corticospinal tract. The RGM A-specific polyclonal antibody given locally via pump for two weeks induced long-distance regeneration of injured nerve fibers (Hata et al., J. Cell Biol. 173:47-58, 2006).

Hundreds of nerve fibers extended past the lesion site and the longest fibers regenerated for more than 10 mm beyond the lesion, whereas no regenerating fibers were found distal to the lesion in control antibody-treated animals. The functional recovery of the anti-RGM A treated rats was significantly improved in comparison with control-antibody treated, spinally injured rats, thereby proving that RGM A is a potent neuroregeneration inhibitor and a valuable target for stimulating recovery in indications characterized by axon damage or nerve fiber injury (Hata et al., J. Cell Biol. 173:47-58, 2006; Kyoto et al. Brain Res. 1186: 74-86, 2007). In addition neutralising the RGM A protein with a function-blocking polyclonal antibody stimulated not only regrowth of damaged nerve fibers in the spinally injured rats but enhanced their synapse formation thereby enabling the reformation or restoration damaged neuronal circuits (Kyoto et al. Brain Res. 1186: 74-86, 2007).

The rgm gene family encompasses three different genes, two of them, rgm a and b, are expressed in the mammalian CNS originating RGM A and RGM B proteins, whereas the third member, rgm c, is expressed in the periphery (Mueller et al., Philos. Trans. R. Soc. Lond. B Biol. Sci. 361: 1513-29, 2006), where RGM C plays an important role in iron metabolism. In vitro, RGM A inhibits neurite outgrowth by binding to Neogenin, which has been identified as an RGM receptor (Rajagopalan et al. Nat Cell Biol.: 6(8), 756-62, 2004). Neogenin had first been described as a netrin-binding protein (Keino-Masu et al. Cell, 87(2):175-85, 1996). This is an important finding because binding of Netrin-1 to Neogenin or to its closely related receptor DCC (deleted in colorectal cancer) has been reported to stimulate rather than to inhibit neurite growth (Braisted et al. J. Neurosci. 20: 5792-801, 2000). Blocking RGM A therefore releases the RGM-mediated growth inhibition by enabling Neogenin to bind its neurite growth-stimulating ligand Netrin. Based on these observations, neutralizing RGM A can be assumed to be superior to neutralizing neogenin in models of human spinal cord injury. Besides binding of RGM A to Neogenin and inducing neurite growth inhibition, the binding of RGM A or B to the bone morphogenetic proteins BMP-2 and BMP-4 could represent another obstacle to successful neuroregeneration and functional recovery (Mueller et al., Philos. Trans. R. Soc. Lond. B Biol. Sci. 361: 1513-29, 2006).

There is a need in the art for improved antibodies capable of binding RGM A, preferably a monoclonal antibody that blocks RGM A and prevents the interaction between RGM A and its receptor and/or binding proteins, i.e. Neogenin and BMP-2, BMP-4.

The present application provides (a) the generation of a neutralizing monoclonal antibody against RGM A, which selectively inhibits binding of RGM A to its receptor Neogenin and to bone morphogenetic proteins 2 and 4 (BMP-2, BMP-4), and (b) the generation of a neutralizing monoclonal antibody against RGM A, which selectively inhibits binding of RGM A to bone morphogenetic proteins 2 and 4 (BMP-2, BMP-4). The neutralizing monoclonal antibodies of the present invention are expected to stimulate regrowth of injured or damaged nerve fibers and formation of functional synapses of regenerating nerve fibers since one of the neutralizing monoclonal antibodies of the present invention appears to transform the inhibitory nature of RGM A in a condition in which neuronal cells prefer to migrate and grow on an RGM A substrate, and not on a permissive substrate like Collagen I. In addition this antibody is able to induce long-distance regeneration in an in vivo rat model of optic nerve injury and it also enhances remyelination of lesioned and regenerating nerve fibers.

Accordingly, the neutralizing monoclonal antibodies of the present invention are expected to promote neuronal regeneration and regrowth of damaged or broken neuronal connections in the injured and inflamed human CNS, for example in multiple sclerosis, after acute spinal cord injury, brain trauma, or in neurodegenerative diseases such as for example, Huntington's chorea, Parkinson's disease, Alzheimer's disease.

SUMMARY OF THE INVENTION

According to one aspect the present invention provides a binding protein that dissociates from human RGM A (hRGM A) with a $K_D$ Of $1 \times 10^{-7}$ M or less and a $k_{off}$ rate constant of $1 \times 10^{-2}$ s$^{-1}$ or less, both determined by surface plasmon resonance.

According to another aspect the invention relates to a binding protein, as for example a binding protein showing the above kinetic features, that binds to human RGM A and neutralizes the neurite outgrowth inhibitory activity of human RGM A as determined in a standard in vitro assay, as for example the Ntera neuronal outgrowth assay as exemplified in Example 3, below.

The invention also relates to binding protein as defined above, having at least one of the following additional functional characteristics:
  binding to rat RGM A,
  binding to human RGM C, and
  binding to rat RGM C.

In particular, the binding protein as described herein modulates the ability of RGM to bind to at least one of its receptors.

Such binding protein, in particular, binds to a receptor binding domain of human RGM A. For RGM A a N- and a C-terminal receptor binding domains have been identified. Particular embodiments of the binding proteins of the invention bind to the N-terminal receptor binding domain of RGM A, as illustrated by the inhibition of binding between an N-terminal hRGM A fragment, as for example 47-168 and receptor molecules, like Neogenin and BMP-4. Said N-terminal hRGM A fragment may have a total length of about 30 to about 150 or about 30 to about 122 amino acid residues. As a non-limiting example Fragment 0 (corresponding to the N-terminal residues 47-168) of hRGM A as described herein or any shorter receptor binding fragment may be mentioned.

In particular said binding protein modulates, preferably inhibits, at least one of the following interactions:
  binding of human RGM A to human BMP-4.
  binding of hRGM A to human Neogenin,
  binding of hRGM C to human Neogenin,
  binding of human RGM A to human BMP-2.

According to a particular embodiment, the binding protein as herein defined is a humanized antibody.

The binding protein as described above may have an antigen binding domain, said binding protein capable of binding an epitope of an RGM molecule, said antigen binding domain comprising at least one CDR comprising an amino acid sequence selected from the group consisting of

| | |
|---|---|
| GTTPDY, | (SEQ ID NO: 59) |
| FQATHDPLT, | (SEQ ID NO: 62) |
| ARRNEYYGSSFFDY, | (SEQ ID NO: 65) |
| LQGYIPPRT, and | (SEQ ID NO: 68) | modified CDR amino acid sequences having a sequence identity of at least 50% to one of said sequences. In another embodiment the present invention relates to a binding protein, comprising an antigen binding domain, said binding protein being capable of binding an epitope of an RGM molecule, said antigen binding domain comprising at least one CDR comprising an amino acid sequence selected from the group consisting of:

| | |
|---|---|
| GTTPDY, | (SEQ ID NO: 59) |
| FQATHDPLT, | (SEQ ID NO: 62) |
| ARRNEYYGSSFFDY, | (SEQ ID NO: 65) |
| LQGYIPPRT, and | (SEQ ID NO: 68) | modified CDR amino acid sequences having a sequence identity of at least 50%, as for example at least 55, 60, 65, 70, 75, 80, 85, 90, 95% identity to one of said sequences.

For example, said binding protein may comprise two of said CDRs, as for example SEQ ID NO: 59 and 62; or SEQ ID NO: 65 and 68; wherein at least one of said CDRs may be modified, having a sequence identity of at least 50%, as for example at least 55, 60, 65, 70, 75, 80, 85, 90, 95% identity to one of said sequences.

Said binding protein may further comprise at least one CDR comprise an amino acid sequence selected from the group consisting of SEQ ID NO: 57, 58, 60, 61, 63, 64, 66, 67 and modified CDR amino acid sequences having a sequence identity of at least 50%, as for example at least 55, 60, 65, 70, 75, 80, 85, 90, 95% identity, to one of said sequences.

In another embodiment, a binding protein is provided, wherein said at least one CDR comprises an amino acid sequence selected from the group consisting of:

| | |
|---|---|
| SEQ ID NO: 57 | Residues 31-35 of SEQ ID NO.: 34 |
| SEQ ID NO: 58 | Residues 50-66 of SEQ ID NO.: 34 |
| SEQ ID NO: 59 | Residues 99-104 of SEQ ID NO.: 34 |
| SEQ ID NO: 60 | Residues 24-39 of SEQ ID NO.: 10 |
| SEQ ID NO: 61 | Residues 55-61 of SEQ ID NO.: 10 |
| SEQ ID NO: 62 | Residues 94-102 of SEQ ID NO.: 10 |
| SEQ ID NO: 63 | Residues 31-35 of SEQ ID NO.: 55 |
| SEQ ID NO: 64 | Residues 50-66 of SEQ ID NO.: 55 |
| SEQ ID NO: 65 | Residues 97-110 of SEQ ID NO.: 55 |
| SEQ ID NO: 66 | Residues 24-34 of SEQ ID NO.: 56 |
| SEQ ID NO: 67 | Residues 50-56 of SEQ ID NO.: 56 |
| SEQ ID NO: 68 | Residues 89-97 of SEQ ID NO.: 56 |

In a particular embodiment, said binding protein comprises at least 3 CDRs which are selected from a variable domain CDR set consisting of:

| VH 5F9 set | | |
|---|---|---|
| VH 5F9 CDR-H1 | Residues 31-35 of SEQ ID NO.: 34 | SEQ ID NO: 57 |
| VH 5F9 CDR-H2 | Residues 50-66 of SEQ ID NO.: 34 | SEQ ID NO: 58 |
| VH 5F9 CDR-H3 | Residues 99-104 of SEQ ID NO.: 34 | SEQ ID NO: 59 |
| VL 5F9 set | | |
| VL 5F9 CDR-L1 | Residues 24-39 of SEQ ID NO.: 10 | SEQ ID NO: 60 |
| VL 5F9 CDR-L2 | Residues 55-61 of SEQ ID NO.: 10 | SEQ ID NO: 61 |
| VL 5F9 CDR-L3 | Residues 94-102 of SEQ ID NO.: 10 | SEQ ID NO: 62 |
| VH 8D1 set | | |
| VH 8D1 CDR-H1 | Residues 31-35 of SEQ ID NO.: 55 | SEQ ID NO: 63 |
| VH 8D1 CDR-H2 | Residues 50-66 of SEQ ID NO.: 55 | SEQ ID NO: 64 |
| VH 8D1 CDR-H3 | Residues 97-110 of SEQ ID NO.: 55 | SEQ ID NO: 65 |
| VL 8D1 set | | |
| VL 8D1 CDR-L1 | Residues 24-34 of SEQ ID NO.: 56 | SEQ ID NO: 66 |
| VL 8D1 CDR-L2 | Residues 50-56 of SEQ ID NO.: 56 | SEQ ID NO: 67 |
| VL 8D1 CDR-L3 | Residues 89-97 of SEQ ID NO.: 57 | SEQ ID NO: 68 | or a variable domain set wherein at least one of said 3 CDRs is a modified CDR amino acid sequence having a sequence identity of at least 50%, as for example at least 55, 60, 65, 70, 75, 80, 85, 90, 95% identity, to the parent sequence.

In particular, each of said above mentioned modifications may be generated by single or multiple amino acid addition, deletion, or, in particular, substitution, or combinations thereof.

In another embodiment, the binding protein comprises at least two variable domain CDR sets.

In particular, said at least two variable domain CDR sets are selected from a group consisting of:
VH 5F9 set & VL 5F9 set; and
VH 8D1 set & VL 8D1 set The binding protein according to the invention further comprising a human acceptor framework.

Said human acceptor framework may comprise at least one amino acid sequence selected from the group consisting of SEQ ID NO: 15, 16, 17, 18, 19, 20, 21, 22, 23, 24, 25, 26, 27, 28, 29, 30, 31, 32 and 33.

The binding protein of the invention may, in particular, comprise at least one set of framework sequences selected from the group consisting of the sets:
(1) VH3-48 set (Seq ID NO: 15, 16 and 17)
VH3-33 set (SEQ ID NO: 21, 22 and 23)
VH3-23 set (SEQ ID NO: 24, 25 and 26)
each of which sets being combined with a further framework sequence, selected from
JH3 (SEQ ID NO:18),
JH4 (SEQ ID NO:19),
JH6 (SEQ ID NO:20);
or
(2) selected from the group consisting of the sets
A18 set: (SEQ ID NO: 27, 28 and 29)
A17 set: (SEQ ID NO: 31, 32 and 33)
each of which sets being combined with a further framework sequence, selected from JK2 (SEQ ID NO:2)

According to particular embodiments, the binding protein of any one of the preceding claims comprising at least one CDR-grafted heavy chain variable domain selected from SEQ ID NO: 35, 36, 37, 38, 39, 40, 41, 42, and 43; and/or at least one CDR-grafted light chain variable domain selected from SEQ ID NO: 44, 45, and 46.

More particular, the binding protein of the invention comprises a combination of two variable domains, wherein said two variable domains have amino acid sequences selected from:

SEQ ID NOs: 35 & 44; 36 & 44; 37 & 44; 38 & 44; 39 & 44; 40 & 44; 41 & 44; 42 & 44; 43 & 44;
SEQ ID NOs: 35 & 45; 36 & 45; 37 & 45; 38 & 45; 39 & 45; 40 & 45; 41 & 45; 42 & 45; 43 & 45;
SEQ ID NOs: 35 & 46; 36 & 46; 37 & 46; 38 & 46; 39 & 46; 40 & 46; 41 & 46; 42 & 46; 43 & 46;

In another embodiment of the invention, said human acceptor framework of the binding protein comprises at least one framework region amino acid substitution at a key residue, said key residue selected from the group consisting of:
a residue adjacent to a CDR;
a glycosylation site residue;
a rare residue;
a residue capable of interacting with a RGM epitope;
a residue capable of interacting with a CDR;
a canonical residue;
a contact residue between heavy chain variable region and light chain variable region;
a residue within a Vernier zone;
an N-terminal residue capable of paraglutamate formation and
a residue in a region that overlaps between a Chothia-defined variable heavy chain CDR1 and a Kabat-defined first heavy chain framework.

In particular, said key residues are selected from the group consisting
(heavy chain sequence position): 1, 5, 37, 48, 49, 88, 98
(light chain sequence position): 2, 4, 41, 51

In a particular embodiment, the binding protein of the invention is or comprises a consensus human variable domain.

According to another embodiment of the binding protein of the invention, said human acceptor framework comprises at least one framework region amino acid substitution, wherein the amino acid sequence of the framework is at least 65%, as for example at least 70, 75, 80, 85, 90, 95, 96, 97, 98, or 99%, identical to the sequence of said human acceptor framework and comprises at least 70 amino acid residues, as for example at least 75, 80, or 85 residues, identical to said human acceptor framework.

According to particular embodiment, the binding protein of the invention comprises at least one framework mutated variable domain having an amino acid sequence selected from the group consisting of:
SEQ ID NO: 47, 48, 49, 50; (VH domain), and/or
selected from the group consisting of:

SEQ ID NO: 51, 52, 53, and 54 (VL domain)

In particular, said binding protein comprises two optionally framework mutated variable domains, wherein said two variable domains have amino acid sequences selected from the groups consisting of:

Binding proteins with different combinations of functional features, and consequently showing different functional profiles, as disclosed herein, are also within the scope of the invention. Non-limiting examples of such profiles are listed below:

| Feature | Profiles | | | | | | | | | | | | | | | | | | | | | |
|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
| Binding to human RGM A | + | + | + | + | + | + | + | + | + | + | + | + | + | + | + | + | + | + | + | + | + | + |
| Binding to rat RGM A | + | − | + | − | + | + | − | + | − | + | − | + | − | + | − | + | − | + | − | + | | + |
| Binding to human RGM C | + | − | − | − | + | − | − | + | + | − | − | + | + | − | − | + | + | − | − | + | + |
| Binding to rat RGM C | + | − | − | − | − | − | − | − | − | + | + | + | + | − | − | − | − | − | + | + | + | + |
| Inhibition of binding of hRGM A to human Neogenin | + | − | − | + | + | + | + | + | + | + | + | + | + | + | + | + | + | + | + | + | + | + |
| Inhibition of binding of hRGM C to human Neogenin | + | − | − | − | − | + | − | − | − | − | − | − | − | − | + | + | + | + | + | + | + | + |
| Inhibition of binding of human RGM A to human BMP-2 | + | + | + | + | + | + | − | − | − | − | − | − | − | − | − | − | − | − | − | − | − | − |
| Inhibition of binding of human RGM A to human BMP-4 | + | + | + | + | + | + | − | − | − | − | − | − | − | − | − | − | − | − | − | − | − | − |

SEQ ID NOs: 47 & 44; 47 & 45; 47 & 46; 47 & 51; 47 & 52; 47 & 53; 47 & 54;
SEQ ID NOs: 48 & 44; 48 & 45; 48 & 46; 48 & 51; 48 & 52; 48 & 53; 48 & 54;
SEQ ID NOs: 49 & 44; 49 & 45; 49 & 46; 49 & 51; 49 & 52; 49 & 53; 49 & 54;
SEQ ID NOs: 50 & 44; 50 & 45; 50 & 46; 50 & 51; 50 & 52; 50 & 53; 50 & 54;

The binding proteins of the invention as described herein are capable of binding at least one target, selected from RGM molecules.

In particular, they are capable of binding to human RGM A, and optionally at least one further RGM molecule of human origin or originating from cynomolgus monkeys, rat, chick, frog, and fish.

For example they may additionally bind to rat RGM A, human RGM C, and/or rat RGM C.

In particular, the binding protein of the invention is capable of modulating, in particular, capable of neutralizing or inhibiting a biological function of a target, selected from RGM molecules as defined above.

In particular, the binding protein of the invention modulates, in particular inhibits, the ability of RGM to bind to at least one of its receptors, as for example Neogenin, and BMP, like BMP-2 and BMP-4.

For example said binding protein modulates, in particular diminishes and preferably inhibits at least one of the following interactions:
binding of human RGM A to human BMP-4.
binding of hRGM A to human Neogenin,
binding of hRGM C to human Neogenin,
binding of human RGM A to human BMP-2.

For example, profile 1 is met by antibody 5F9 as provided by the present invention and its derivatives described herein.

For example, profile 2 is met by antibody 8D1 as provided by the present invention and its derivatives as disclosed herein.

In particular, a binding protein of the invention is capable of inhibiting at least one biological activity of RGM, in particular RGM A, wherein said RGM A is selected from human, cynomolgus monkeys, rat, chick, frog, and fish.

According to another embodiment the binding protein of the invention has one or more of the following kinetic features:

(a) an on rate constant ($k_{on}$) to said target selected from the group consisting of: at least about $10^2$ M$^{-1}$ s$^{-1}$; at least about $10^3$ M$^{-1}$ s$^{-1}$; at least about $10^4$ M$^{-1}$ s$^{-1}$; at least about $10^5$ M$^{-1}$ s$^{-1}$; at least about $10^6$ M$^{-1}$ s$^{-1}$, and at least about $10^7$ M$^{-1}$ s$^{-1}$, as measured by surface plasmon resonance;

(b) an off rate constant ($k_{off}$) to said target selected from the group consisting of: at most about $10^{-2}$ s$^{-1}$, at most about $10^{-3}$ s$^{-1}$; at most about $10^{-4}$ s$^{-1}$; at most about $10^{-5}$ s$^{-1}$; and at most about $10^{-6}$ s$^{-1}$, as measured by surface plasmon resonance; or (c) a dissociation constant ($K_D$) to said target selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

According to a further aspect, the present invention provides an antibody construct comprising a binding protein described above, said antibody construct further comprising a linker polypeptide or an immunoglobulin constant domain.

Said antibody construct or binding protein of the invention may be selected from the group consisting of: an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, a dual variable domain immunoglobulin, and a bispecific antibody.

In an antibody construct according to the invention said binding protein comprises a heavy chain immunoglobulin constant domain selected from the group consisting of;
a human IgM constant domain,
a human IgG1 constant domain,
a human IgG2 constant domain,
a human IgG3 constant domain,
a human IgG4 constant domain,
a human IgE constant domain,
a human IgD constant domain,
a human IgA1 constant domain
a human IgA2 constant domain
a human IgY constant domain and
corresponding mutated constant domains In particular, an antibody construct according to the invention comprises an immunoglobulin constant domain having an amino acid sequence selected from the group consisting of: SEQ ID NO: 11, 12, 13 and 14

According to another aspect, the present invention provides an antibody conjugate comprising an antibody construct described herein, said antibody conjugate further comprising an agent selected from the group consisting of; an immunoadhesion molecule, an imaging agent, a therapeutic agent, and a cytotoxic agent, each of which agent being conjugated, of example covalently bound to said binding protein.

For example, said agent is an imaging agent selected from the group consisting of a radiolabel, an enzyme, a fluorescent label, a luminescent label, a bioluminescent label, a magnetic label, and biotin. In particular, said imaging agent is a radiolabel selected from the group consisting of: $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$.

For example, said agent is a therapeutic or cytotoxic agent selected from the group consisting of; an anti-metabolite, an alkylating agent, an antibiotic, a growth factor, a cytokine, an anti-angiogenic agent, an anti-mitotic agent, an anthracycline, toxin, and an apoptotic agent.

According to another embodiment, said binding protein of the invention as described herein possesses a human glycosylation pattern.

Furthermore, the binding proteins, antibody constructs and antibody conjugate according to the invention may exist as a crystal (in crystalline form), preferably retaining biological activity.

In particular, said crystal is a carrier-free pharmaceutical controlled release crystal. In view of said crystalline form the binding protein, antibody construct or antibody conjugate may have a greater half life in vivo than the corresponding soluble counterpart In another aspect of the present invention provides an isolated nucleic acid encoding a binding protein amino acid sequence, antibody construct amino acid sequence, and antibody conjugate amino acid sequence as described herein.

The invention also relates to a vector comprising an isolated nucleic acid as described herein. In particular, the vector is selected from the group consisting of pcDNA, pTT, pTT3, PEFBOS, pBV, pJV, and pBJ.

The invention also relates to a host cell comprising such a vector. In particular, said host cell is a prokaryotic cell, as for example E. coli; or is a eukaryotic cell, and may be selected from the group consisting of protist cell, animal cell, plant cell and fungal cell. In particular, said eukaryotic cell is an animal cell selected from the group consisting of; a mammalian cell, an avian cell, and an insect cell. Preferably said host cell is selected from HEK cells, CHO cells, COS cells and yeast cells. The yeast cell may be Saccharomyces cerevisiae and said insect cell ay be a Sf9 cell.

The invention also provides a method of producing a protein capable of binding RGM, comprising culturing a host cell as defined herein in culture medium under conditions sufficient to produce a binding protein capable of binding RGM.

The invention also relates to a protein produced according to said method.

The invention also provides a composition for the release of a binding protein said composition comprising
(a) a formulation, wherein said formulation comprises a crystallized product protein as defined herein, and an ingredient; and
(b) at least one polymeric carrier.

Said polymeric carrier may be a polymer selected from one or more of the group consisting of: poly(acrylic acid), poly(cyanoacrylates), poly(amino acids), poly(anhydrides), poly(depsipeptide), poly(esters), poly(lactic acid), poly(lactic-co-glycolic acid) or PLGA, poly(b-hydroxybutryate), poly(caprolactone), poly(dioxanone); poly(ethylene glycol), poly((hydroxypropyl)methacrylamide), poly [(organo) phosphazene], poly(ortho esters), poly(vinyl alcohol), poly(vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polyeaccharides, blends and copolymers thereof.

Said ingredient may be selected from the group consisting of albumin, sucrose, trehalose, lactitol, gelatin, hydroxypropyl-β-cyclodextrin, methoxypolyethylene glycol and polyethylene glycol.

According to another aspect the present invention provides a method for treating a mammal comprising the step of administering to the mammal an effective amount of the composition as defined herein.

According to another aspect the present invention provides a pharmaceutical composition comprising the product (in particular, a binding protein, construct or conjugate as scribed herein above), and a pharmaceutically acceptable carrier.

Said pharmaceutically acceptable carrier may function as adjuvant useful to increase the absorption, or dispersion of said binding protein.

For example said adjuvant is hyaluronidase.

According to another embodiment said pharmaceutical further comprises at least one additional therapeutic agent for treating a disorder in which RGM activity is detrimental. For example said agent is selected from the group consisting of: therapeutic agent, imaging agent, cytotoxic agent, angiogenesis inhibitors; kinase inhibitors; co-stimulation molecule blockers; adhesion molecule blockers; anti-cytokine antibody or functional fragment thereof; methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

The present invention also relates to a method for reducing human RGM A activity comprising contacting human RGM A with at least one product (in particular, a binding protein, construct or conjugate as scribed herein above), such that at least one human RGM A activity is reduced.

The present invention also relates to a method for decreasing hRGM A binding to Neogenin receptor in a subject in need thereof, comprising the step of administering to the subject a product of the invention (in particular, a binding protein, construct or conjugate as scribed herein above).

The present invention also relates to a method for decreasing hRGM A binding to bone morphogenetic protein-2 and/or bone morphogenetic protein-4 (BMP-2 and BMP-4) in a subject in need thereof, comprising the step of administering to the subject a product of the invention (in particular, a binding protein, construct or conjugate as scribed herein above).

The present invention also relates to a method for treating a subject for a disorder associated with RGM A activity comprising the step of administering alone or in combination with other therapeutic agents a product of the invention (in particular, a binding protein, construct or conjugate as described herein above).

The present invention also relates to a method for reducing RGM A activity in a subject suffering from a disorder in which RGM A activity is detrimental, comprising administering to the subject a product of the invention (in particular, a binding protein, construct or conjugate as scribed herein above), alone or in combination with other therapeutic agents.

Said disorder preferably comprises neurological diseases selected from the group comprising Amyotrophic Lateral Sclerosis, Brachial Plexus Injury, Brain Injury, including traumatic brain injury, Cerebral Palsy, Guillain Barre, Leukodystrophies, Multiple Sclerosis, Post Polio, Spina Bifida, Spinal Cord Injury, Spinal Muscle Atrophy, Spinal Tumors, Stroke, Transverse Myelitis; dementia, senile dementia, mild cognitive impairment, Alzheimer-related dementia, Huntington's chorea, tardive dyskinesia, hyperkinesias, manias, Morbus Parkinson, steel-Richard syndrome, Down's syndrome, myasthenia gravis, nerve trauma, vascular amyloidosis, cerebral hemorrhage I with amyloidosis, brain inflammation, acute confusion disorder, amyotrophic lateral sclerosis, glaucoma and Alzheimer's disease.

Further particular aspects of the invention are described below:

An isolated binding protein that specifically interacts with at least one epitope of a hRGM A protein;

said isolated protein being a monoclonal neutralizing antibody or antigen binding fragment thereof;

said antigen binding fragment comprising a VH and a VL domain;

said neutralizing antibody diminishing the ability of hRGM A to bind to its receptor;

said neutralizing antibody being capable of inhibiting hRGM A biological activity;

said antibody recognizing a RGM A receptor selected from human, cynomolgus monkeys, rat, chick, frog, and fish;

said antibody recognizing a RGM A protein sharing 90% homology to the amino acid sequence SEQ ID NO:2;

said antibody wherein the RGM A protein is encoded by a nucleic acid that shares 90% homology to the nucleic acid sequence SEQ ID NO:1;

said antibody having at least 90% amino acid sequence identity with a sequence comprising a heavy chain variable region (VH region) comprising the sequence of SEQ ID NO:9 or 34 or a humanized, optionally further mutated version of said VH region;

said antibody having at least 90% amino acid sequence identity with a sequence comprising a light chain variable region (VL region) comprising the sequence of SEQ ID NO:10 or a humanized, optionally further mutated version of said VL region said antibody that binds to hRGM A wherein the antibody is glycosylated;

said antibody or antigen-binding fragment, wherein said antibody or antigen-binding fragment is a mouse antibody, a humanized antibody, a fully human, a chimeric antibody, an antigen-binding fragment of a humanized antibody, or an antigen-binding fragment of a chimeric antibody;

said antibody or antigen-binding fragment, wherein said antibody or antigen-binding fragment is an antigen-binding fragment selected from the group consisting of a Fab fragment, a Fab' fragment, a F(ab')$_2$ fragment and a Fv fragment;

said monoclonal antibody that specifically binds to at least one epitope of hRGM A, wherein said monoclonal antibody is the monoclonal antibody secreted by hybridoma cell line as described herein;

said monoclonal antibody, wherein the binding results in inactivation of the interaction of hRGM A with its receptor;

said hybridoma cell line that produces a monoclonal antibody, which specifically binds to at least one epitope of hRGM A;

said hybridoma cell line, wherein the hybridoma is selected from the group consisting of human, mouse, rat, sheep, pig, cattle, goat, and horse hybridoma;

said monoclonal antibody, wherein the binding results in inactivation of hRGM A;

said hybridoma cell line that produces a monoclonal antibody, which specifically binds to at least one epitope of hRGM A;

said hybridoma cell line, wherein the hybridoma is selected from the group consisting of human, mouse, rat, sheep, pig, cattle, goat, and horse hybridoma;

said monoclonal neutralizing antibody or antigen-binding fragment thereof, having at least one characteristic selected from the group consisting of:
a) binding to mammalian RGM A with affinity in the nM range or less;
b) functionally antagonizing in vitro RGM A activity in neurite outgrowth assay with μM, nM or less efficacy;
c) in vivo inducing sprouting in the optic nerve crush model;
d) in vivo inducing sprouting in a spinal cord injury model;
e) relieving in vivo experimental spinal cord injury by enhancing regenerative growth of injured nerve fibers; or
f) relieving in vivo experimental spinal cord injury by promoting synapse formation;

an isolated nucleic acid encoding said monoclonal neutralizing antibody or antigen-binding fragment;

a vector comprising said isolated nucleic acid;

said vector selected from the group consisting of pcDNA; pTT; pTT3; PEFBOS; pBV; pJV; pHybE and pBJ;

a host cell transformed with said vector according wherein the host cell is selected form the group consisting of protist cell, animal cell, plant cell and fungal cell;

said host cell, wherein the animal cell is a mammalian cell selected form the group comprising HEK293, CHO and COS;

A host cell transformed with the vector according to claim 24, wherein the host cell is a eukaryotic cell;

a method of producing the binding protein according that binds hRGM A, comprising culturing a host cell in a culture medium under conditions sufficient to produce a binding protein that binds hRGM A;

a pharmaceutical composition comprising said monoclonal antibody or antigen-binding portion and a pharmaceutically acceptable carrier;

a method for decreasing hRGM A binding to Neogenin receptor in a subject in need thereof, comprising the step of administering to the subject said antibody;

a method for decreasing hRGM A binding to bone morphogenetic protein-2 and bone morphogenetic protein-4 (BMP-2 and BMP-4) in a subject in need thereof, comprising the step of administering to the subject sad antibody;

a method of treating a subject for a disorder associated with RGM A activity comprising the step of administering alone or in combination with other therapeutic agents said antibody;

a method for reducing RGM A activity in a subject suffering from a disorder in which RGM A activity is detrimental, comprising administering to the subject said antibody alone or in combination with other therapeutic agents;

said antibody, comprising at least one VH region comprising an amino acid sequence selected from SEQ ID NO: 35, 36, 37, 38, 39, 40, 41, 42 and 43;

said antibody, comprising at least one VL region comprising an amino acid sequence selected from SEQ ID NO: 44, 45 and 46;

said antibody, additionally modified by 1 to 5 mutations in an VH or VL sequence;

said antibody, wherein the mutations are selected from framework back mutations and mutations of Vernier and VH/VL interfacing residues;

Any teaching or reference to SEQ ID NO: 34 as disclosed herein in analogy applies to SEQ ID NO:9.

DETAILED DESCRIPTION

Figure 1:
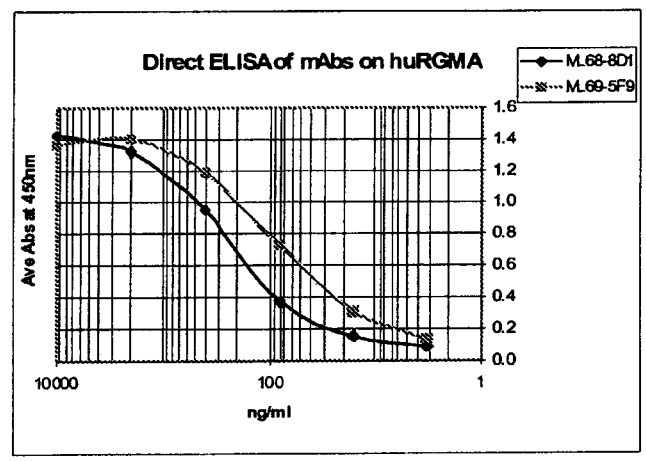
FIG. 1A shows the monoclonal antibodies binding to hRGM A in ELISA assay.
FIG. 1B depict the monoclonal antibodies binding to hRGM A expressed in HEK 293 cells.
FIG. 1C depict the monoclonal antibodies binding to rat RGM A expressed in HEK 293 cells.
Figure 1:
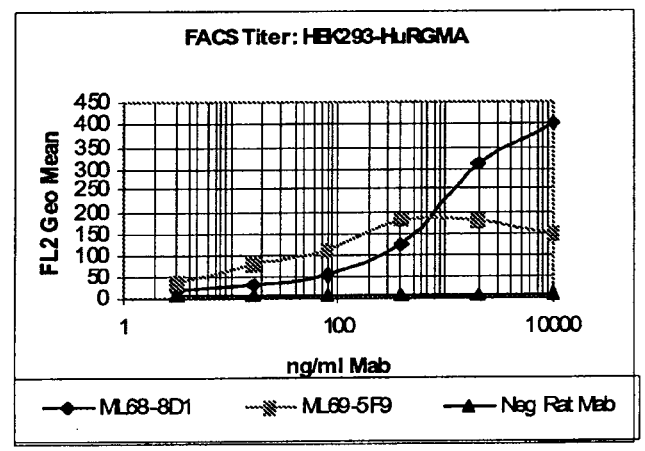
Figure 1:
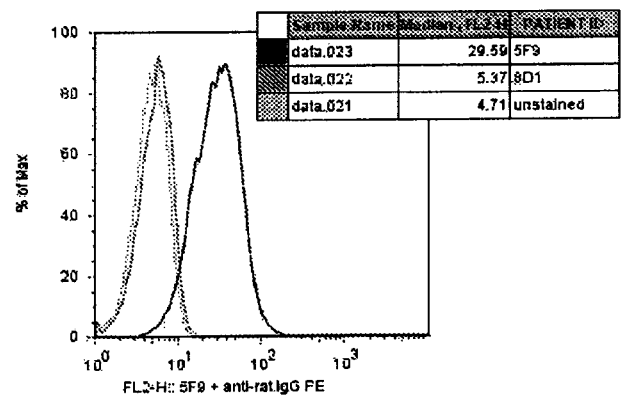

This invention describes RGM A binding proteins, more specifically monoclonal RGM A antibodies, especially humanized monoclonal RGM A antibodies, or antigen-binding portions thereof, that bind RGM A. Various aspects of this application relate to antibodies and antibody fragments, and pharmaceutical compositions thereof, as well as nucleic acids, recombinant expression vectors and host cells for making such antibodies and fragments. Methods of using the antibodies of this application to detect human RGM A; to neutralize human RGM and/or human RGM A activity, either in vivo or in vitro, and to regulate gene expression are also encompassed by the invention.

1. General Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, selected terms are defined below.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The term "human RGM A" (abbreviated herein as hRGM A), as used herein refers to a glycosylphosphatidyl-inositol (gpi)-anchored glycoprotein with 450 amino acids, was first described as a neurite growth repellent or neurite growth inhibitor during development of topographic projections (Stahl et al. Neuron 5: 735-43, 1990; Mueller, in Molecular Basis of Axon Growth and Nerve Pattern Formation, Edited by H. Fujisawa, Japan Scientific Societies Press, 215-229, 1997). The rgm gene family encompasses three different genes, two of them, rgm a and b, are expressed in the mammalian CNS, whereas the third member, rgm c, is expressed in the periphery (Mueller et al., Philos. Trans. R. Soc. Lond. B Biol. Sci. 361: 1513-29, 2006), where it plays an important role in iron metabolism. Human RGM proteins have a sequence identity of 43%-50%; the amino acid homology of human and rat RGM A is 89%. Human RGM proteins share no significant sequence homology with any other known protein. They are proline-rich proteins containing an RGDregion and have structural homology to the Von-Willebrand Factor domain and are cleaved at the N-terminal amino acid 168 by an unknown protease to yield the functionally active protein (Mueller et al., Philos. Trans. R. Soc. Lond. B Biol. Sci. 361: 1513-29, 2006).

In vitro, RGM A inhibits neurite outgrowth at picomolar concentrations by binding to Neogenin, which has been identified as an RGM receptor (Rajagopalan et al. Nat Cell Biol.: 6(8), 756-62, 2004). Neogenin had first been described as a netrin-binding protein (Keino-Masu et al. Cell, 87(2):175-85, 1996), but its affinity for Netrin ($K_d$ 2 nM) is an order of magnitude lower than that for RGM ($K_d$ 0.2 nM) (Rajagopalan et al. Nat Cell Biol.: 6(8), 756-62, 2004). This is an important finding because binding of Netrin-1 to Neogenin or to its closely related receptor DCC (deleted in colorectal cancer) has been reported to stimulate rather than to inhibit neurite growth (Braisted et al. J. Neurosci. 20: 5792-801, 2000).

Besides binding of RGM A to Neogenin and inducing neurite growth inhibition, the binding of RGM A or B to the bone morphogenetic proteins BMP-2 and BMP-4 could represent another obstacle to successful neuroregeneration and functional recovery (Mueller et al., Philos. Trans. R. Soc. Lond. B Biol. Sci. 361: 1513-29, 2006). Both classes of proteins (Neogenin and the BMPs) have been reported to transduce the neurite growth inhibitory signal of RGM A via two completely different and independent signal transduction pathways. Usually, expression of these BMP proteins is relatively low in most regions of the adult CNS, but rapid increases in expression and accumulation of some BMPs (e.g. BMP-2, BMP-6, BMP-7) have been reported in response to injury and insult (Lai et al., Neuroreport 8: 2691-94, 1997; Martinez et al. Brain Res. 894: 1-11, 2001; Hall and Miller, J. Neurosci. Res. 76: 1-8, 2004; Setoguchi et al., Exp. Neurol. 189: 33-44, 2004). In addition, in a model of multiple sclerosis, the experimental autoimmune encephalomyeltis (EAE) model, BMP-4, BMP-6 and BMP-7 were upregulated in mouse spinal cord (Ara et al., J. Neurosci. Res. 86: 125-35, 2008). BMP-2 has been reported to inhibit neurite growth by binding to cell surface RGM A, BMP-receptors I and II and by directly activating LIM-kinase (Matsuura et al. Biochem Biophys Res Commun., 360: 868-73, 2007) and it is therefore expected that blocking the RGM A-BMP-2 interaction will further increase functional recovery after CNS injury.

As mentioned above, spinally injured rats and humans with brain injury, show massive accumulations of cellular RGM at the injury site and the staining pattern of RGM A in rats at the spinal lesion site is very similar to the pan RGM antibody staining in humans, suggesting that most of the pan RGM staining in humans is related to RGM A localization but not to RGM B localization (Schwab et al., Arch. Neurol. 62: 1561-8, 2005a; Schwab et al. Eur. J. Neurosci. 21:1569-76, 2005 b; Hata et al. J. Cell Biol. 173:47-58, 2006). In healthy human brain, pan RGM staining (RGM A & B immunoreactivity) was detected on white matter fibers, oligodendrocytes, perikarya of few neurons, some vascular smooth muscle and few endothelial cells. No staining of astrocytes was observed. The RGM staining pattern in adult healthy human brain is very similar to the staining pattern observed in adult rat spinal cords (Schwab et al. Eur. J. Neurosci. 21:1569-76, 2005 b; Hata et al. J. Cell Biol. 173:47-58, 2006).

Based on the accumulation of RGM A at lesion sites in brain and spinal cord injury and due to its cellular neurite growth inhibitory activity, it is expected that the protein will exert neurite growth inhibitory activity and its neutralization by antibodies, or antigen-binding fragment thereof that bind to at least one epitope of the human RGM A might result in improved regrowth of injured nerve fibers and in an enhancement of functional recovery in indications characterized by nerve fiber injury and RGM accumulation.

Unless otherwise stated the term "RGM A" also encompasses RGM A molecules isolated or obtained from other species, as for example, rodents, like mice or rats; specifically, the rat derived molecule is designated herein as "rat RGM A".

TABLE 1

LIST OF SEQUENCES OF RGM A RELATED MOLECULES

| Protein | Sequence identifier | Description |
| --- | --- | --- |
| hRGM A | SEQ ID NO. 2 | Human RGM A protein sequence |
|  | SEQ ID NO. 1 | Human RGM A nucleotide sequence |
| hRGM A | SEQ ID NO. 4 | Human RGM A-fc protein sequence |
|  | SEQ ID NO. 3 | Human RGM A-fc nucleotide sequence |
| hRGM A | SEQ ID NO. 6 | Human RGM A light chain - fc protein sequence |
|  | SEQ ID NO. 5 | Human RGM A light chain - fc nucleotide sequence |
| rat RGM A | SEQ ID NO. 8 | Rat RGM A protein sequence |
|  | SEQ ID NO. 7 | Rat RGM A nucleotide sequence |

"Biological activity" as used herein, refers to all inherent biological properties of RGM A as defined herein.

The terms "specific binding" or "specifically binding", as used herein, in reference to the interaction of an antibody, a protein, or a peptide with a second chemical species, mean that the interaction is dependent upon the presence of a particular structure (e.g., an "antigenic determinant" or "epitope" as defined below) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below. An antibody is said to be "capable of binding" a molecule if it is capable of specifically reacting with the molecule to thereby bind the molecule to the antibody.

A "monoclonal antibody" as used herein is intended to refer to a preparation of antibody molecules, which share a common heavy chain and common light chain amino acid sequence, in contrast with "polyclonal" antibody preparations that contain a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497).

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen-binding portion" or "antigen-binding fragment" of an antibody (or simply "antibody portion" or "antibody fragment"), as used herein, refers to one or more fragments of an antibody that retain the ability to specifically bind to an antigen (e.g., hRGM A). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Human IgG heavy chain and light chain constant domain amino acid sequences are known in the art and represented in Table 2.

TABLE 2

SEQUENCE OF HUMAN IgG HEAVY CHAIN CONSTANT DOMAIN AND LIGHT CHAIN CONSTANT DOMAIN

| Protein | Sequence Identifier | Sequence 12345678901234567890123456789 0 |
|---|---|---|
| Ig gamma-1 constant region | SEQ ID NO.: 11 | ASTKGPSVFFLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig gamma-1 constant region mutant | SEQ ID NO.: 12 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig Kappa constant region | SEQ ID NO.: 13 | TVAAPSVFIFPPSDEQLKSGTASVVCLLNN FYPREAKVQWKVDNALQSGNSQESVTEQDS KDSTYSLSSTLTLSKADYEKHKVYACEVTH QGLSSPVTKSFNRGEC |
| Ig Lambda constant region | SEQ ID NO.: 14 | QPKAAPSVTLFPPSSEELQANKATLVCLIS DFYPGAVTVAWKADSSPVKAGVETTTPSKQ SNNKYAASSYLSLTPEQWKSHRSYSCQVTH EGSTVEKTVAPTECS |

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hRGM A is substantially free of antibodies that specifically bind antigens other than hRGM A). An isolated antibody that specifically binds hRGM A may, however, have cross-reactivity to other antigens, such as RGM A molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germine immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies which comprise heavy and light chain variable region sequences from one species and constant region sequences from another species, such as antibodies having murine heavy and light chain variable regions linked to human constant regions. The chimeric antibody can be produced through recombinant molecular biological techniques, or may be physically conjugated together.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad. Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, at least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227: 799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4. Different combinations for human framework sequences FR1 to FR4 are stated in said tables.

TABLE 3

HUMAN HEAVY CHAIN ACCEPTOR SEQUENCES

| SEQ ID No. | Protein region | Sequence 123456789012345678901234567890123456789012 |
|---|---|---|
| 15 | VH3-48/JH3 | FR1 EVQLVESGGGLVQPGGSLRLSCAASGFTFS |
| 16 | VH3-48/JH3 | FR2 WVRQAPGKGLEWVS |
| 17 | VH3-48/JH3 | FR3 RFTISRDNAKNSLYLQMNSLRDEDTAVYYCAR |
| 18 | VH3-48/JH3 | FR4 WGQGTMVTVSS |
| 15 | VH3-48/JH4 | FR1 EVQLVESGGGLVQPGGSLRLSCAASGFTFS |
| 16 | VH3-48/JH4 | FR2 WVRQAPGKGLEWVS |
| 17 | VH3-48/JH4 | FR3 RFTISRDNAKNSLYLQMNSLRDEDTAVYYCAR |
| 19 | VH3-48/JH4 | FR4 WGQGTLVTVSS |

TABLE 3-continued

HUMAN HEAVY CHAIN ACCEPTOR SEQUENCES

| SEQ ID No. | Protein region | Sequence 123456789012345678901234567890123456789012 |
|---|---|---|
| 15 | VH3-48/JH6 | FR1 EVQLVESGGGLVQPGGSLRLSCAASGFTFS |
| 16 | VH3-48/JH6 | FR2 WVRQAPGKGLEWVS |
| 17 | VH3-48/JH6 | FR3 RFTISRDNAKNSLYLQMNSLRDEDTAVYYCAR |
| 20 | VH3-48/JH6 | FR4 WGQGTTVTVSS |
| 21 | VH3-33/JH3 | FR1 QVQLVESGGGVVQPGRSLRLSCAASGFTFS |
| 22 | VH3-33/JH3 | FR2 WVRQAPGKGLEWVA |
| 23 | VH3-33/JH3 | FR3 RFTISRDNSKNTLYLQMNSLRAEDTAVYYCAR |
| 18 | VH3-33/JH3 | FR4 WGQGTMVTVSS |
| 21 | VH3-33/JH4 | FR1 QVQLVESGGGVVQPGRSLRLSCAASGFTFS |
| 22 | VH3-33/JH4 | FR2 WVRQAPGKGLEWVA |
| 23 | VH3-33/JH4 | FR3 RFTISRDNSKNTLYLQMNSLRAEDTAVYYCAR |
| 19 | VH3-33/JH4 | FR4 WGQGTLVTVSS |
| 21 | VH3-33/JH6 | FR1 QVQLVESGGGVVQPGRSLRLSCAASGFTFS |
| 22 | VH3-33/JH6 | FR2 WVRQAPGKGLEWVA |
| 23 | VH3-33/JH6 | FR3 RFTISRDNSKNTLYLQMNSLRAEDTAVYYCAR |
| 20 | VH3-33/JH6 | FR4 WGQGTTVTVSS |
| 24 | VH3-23/JH3 | FR1 EVQLLESGGGLVQPGGSLRLSCAASGFTFS |
| 25 | VH3-23/JH3 | FR2 WVRQAPGKGLEWVS |
| 26 | VH3-23/JH3 | FR3 RFTISRDNSKNTLYLQMNSLRAEDTAVYYCAK |
| 18 | VH3-23/JH3 | FR4 WGQGTMVTVSS |
| 24 | VH3-23/JH4 | FR1 EVQLLESGGGLVQPGGSLRLSCAASGFTFS |
| 25 | VH3-23/JH4 | FR2 WVRQAPGKGLEWVS |
| 26 | VH3-23/JH4 | FR3 RFTISRDNSKNTLYLQMNSLRAEDTAVYYCAK |
| 19 | VH3-23/JH4 | FR4 WGQGTLVTVSS |
| 24 | VH3-23/JH6 | FR1 EVQLLESGGGLVQPGGSLRLSCAASGFTFS |
| 25 | VH3-23/JH6 | FR2 WVRQAPGKGLEWVS |
| 26 | VH3-23/JH6 | FR3 RFTISRDNSKNTLYLQMNSLRAEDTAVYYCAK |
| 20 | VH3-23/JH6 | FR4 WGQGTTVTVSS |

TABLE 4

HUMAN LIGHT CHAIN ACCEPTOR SEQUENCES

| SEQ ID No. | Protein region | Sequence 123456789012345678901234567890123456789012 |
|---|---|---|
| 27 | A18/JK2 | FR1 DIVMTQTPLSLSVTPGQPASISC |
| 28 | A18/JK2 | FR2 WYLQKPGQSPQLLIY |
| 29 | A18/JK2 | FR3 GVPDRFSGSGSGTDFTLKISRVEAEDVGVYYC |
| 30 | A18/JK2 | FR4 FGQGTKLEIKR |

TABLE 4-continued

HUMAN LIGHT CHAIN ACCEPTOR SEQUENCES

| SEQ ID No. | Protein region | Sequence<br>123456789012345678901234567890012 |
|---|---|---|
| 31 | A17/JK2 FR1 | DVVMTQSPLSLPVTLGQPASISC |
| 32 | A17/JK2 FR2 | WFQQRPGQSPRRLIY |
| 33 | A17/JK2 FR3 | GVPDRFSGSGSGTDFTLKISRVEAEDVGVYYC |
| 30 | A17/JK2 FR4 | FGQGTKLEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

The term "humanized antibody" generally refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

In particular, the term "humanized antibody" as used herein, is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 50, 55, 60, 65, 70, 75 or 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgY, IgM, IgG, IgD, IgA and IgE, and any isotype, including without limitation IgA1, IgA2, IgG1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 50, 55, 60, 65, 70, 75 or 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "inhibition of binding" of RGM to one of his receptors as used herein encompasses partial (as for example by about 20%, 40%, 60%, 80%, 85%, 90%, 95% or more) or complete reduction of said receptor binding activity. Said "inhibition of binding" may be determined by any suitable method available in the art, preferably by any method as exemplified herein, as for example ELISA based binding assays.

As used herein, the term "neutralizing" refers to neutralization of biological activity of a target protein when a binding protein specifically binds the target protein. Neutralizing may be the result of different ways of binding of said binding protein to the target. For example, neutralizing may be caused by binding of the binding protein in a region of the target which does not affect receptor binding to the target molecule. Alternatively binding of a binding protein may result in a blockade of the receptor binding to the target, which blockade finally neutralizes the target protein activity. Each of said different mechanism may occur according to the invention. Preferably a neutralizing binding protein is a neutralizing antibody whose binding to hRGM A results in neutralization of a biological activity of hRGM A. Preferably the neutralizing binding protein binds hRGM A and decreases a biologically activity of hRGM A by at least about 20%, 40%, 60%, 80%, 85% or more. Neutralization of a biological activity of hRGM A by a neutralizing binding protein can be assessed by measuring one or more indicators of hRGM A biological activity well known in the art. For example neutralization of hRGM A reverses the inhibition in a Ntera neuronal outgrowth assay (see Example 3, below). The Ntera neurite growth assay addresses inhibition of neurite outgrowth. In the absence of an inhibitory RGM A protein or fragment and in the presence of the outgrowth-stimulating substrate laminin, neuronal NTera aggregates show an extensive and dense network of outgrowing neurites. RGM A or RGM A fragments inhibit neurite outgrowth, resulting in reduced length and numbers of neurites. Function-blocking RGM A antagonists or MABs like mAb 5F9 neutralized the neurite outgrowth inhibitory activity of the potent fc-conjugated hRGM A light chain fragment (amino acids 47-168) of the human RGM A protein in neurite growth assays with aggregates of differentiated human NTera neurons, resulting in a strong increase in neurite length and numbers.

A "neutralizing monoclonal antibody" as used herein is intended to refer to a preparation of antibody molecules, which upon binding to the specific antigen are able to compete and inhibit the binding of the natural ligand for said antigen. In a particular embodiment of the present application, the neutralizing antibodies of the present invention are capable of competing with RGM A for binding to Neogenin and/or to BMP-2 and/or BMP-4, and to prevent RGM A biological activity or function. In particular, the neutralizing antibodies of the present invention are capable of binding with RGM A and to prevent binding to Neogenin and/or to BMP-2 and/or BMP-4, and to prevent RGM A biological activity or function. The term "activity" includes activities such as the binding specificity/affinity of an antibody for an antigen, for example, an anti-hRGM A antibody that binds to an RGM A antigen and/or the neutralizing potency of an antibody, for example, an anti-hRGM A antibody whose binding to hRGM A inhibits the biological activity of hRGM A, e.g. as determined in a hRGM A-Neogenin binding assay, hRGM A-BMP-2 binding assay or hRGM A-BMP-4 binding assay as described below in the experimental section.

The biologic activity of RGM A can be described as regulating cellular migration. A special example of cellular migration is neurite growth, which is impeded or inhibited by RGM A proteins. In addition RGM proteins have been shown to modulate activity of BMP-proteins. Herein published examples describe a synergizing, potentiating activity of RGM proteins on the BMP-pathway on one side and an inhibitory activity of RGM proteins on the BMP-pathway, which is important for regulation of iron metabolism, bone and cartilage regeneration and in the CNS for remyelination and regeneration.

The term "epitope" or "antigenic determinant" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_d$", as used herein, is intended to refer to the dissociation constant of a particular antibody-antigen interaction as is known in the art.

The term "labelled binding protein" as used herein, refers to a protein with a label incorporated that provides for the identification of the binding protein. Preferably, the label is a detectable marker, e.g., incorporation of a radiolabelled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences, which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The terms "regulate" and "modulate" are used interchangeably, and, as used herein, refer to a change or an alteration in the activity of a molecule of interest (e.g., the biological activity of hRGM A). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hRGM A). For example, a modulator may cause an increase or decrease in the magnitude of a certain activity or function of a molecule compared to the magnitude of the activity or function observed in the absence of the modulator. The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, hRGM A polypeptides or polypeptides, nucleic acids, carbohydrates, or any other molecules that bind to hRGM A. The term "antagonist" as used herein, refer to a modulator that, when contacted with a molecule of interest causes a decrease in the magnitude of a certain activity or function of the molecule compared to the magnitude of the activity or function observed in the absence of the antagonist. Exemplary antagonists include, but are not limited to, proteins, peptides, antibodies, peptibodies, carbohydrates or small organic molecules. Peptibodies are described, e.g., in WO01/83525.

Particular antagonists of interest include those that block or modulate the biological or immunological activity of hRGM A. Antagonists of hRGM A may include, but are not limited to, proteins, nucleic acids, carbohydrates, or any other molecules, which bind to hRGM A, like monoclonal antibodies that interact with the RGM A molecule. It should be noted that the interaction with RGM A may result in binding and neutralization of other ligands/cell membrane components, and may be useful for additive or synergistic functioning against multiple diseases.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g. prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

2. Polypeptides that Bind hRGM A

The principal embodiment of the present application comprises isolated proteins or polypeptides that specifically bind to at least one epitope of a RGM A protein. The isolated proteins or polypeptides that specifically bind to at least one epitope of a RGM A protein are capable of inhibiting binding of RGM A to its receptor Neogenin and/or to bone morphogenetic proteins 2 and 4 (BMP-2, BMP-4).

The most preferred embodiment of the present application comprises antibodies that bind to RGM A or antigen-binding portions or fragments thereof.

Preferably, anti-RGM A antibodies of the present invention, exhibit a high capacity to reduce or to neutralize RGM A activity, e.g., as assessed by any one of several in vitro and in vivo assays known in the art or described below.

The present application most preferably comprises neutralizing monoclonal antibodies against RGM A, which selectively prevent binding of RGM A to its receptor Neogenin and to bone morphogenetic proteins 2 and 4 (BMP-2, BMP-4), and the generation of a neutralizing monoclonal antibody against RGM A, which selectively prevents binding of RGM A to its coreceptors bone morphogenetic proteins 2 and 4 (BMP-2, BMP-4).

Preferably, the monoclonal neutralizing antibody of the present application is a human antibody or humanized antibody. The term "human antibody" refers to antibodies having variable and constant regions corresponding to, or derived from, human germline immunoglobulin sequences (e.g., see Kabat et al. *Sequences of Proteins of Immunological Interest*, Fifth Edition, U.S. Department of Health and Human Services, NIH Publication No. 91-3242, 1991). The human antibodies of the present application, however, may include amino acid residues not encoded by human germline immunoglobulin sequences (e.g., mutations introduced by random or site-specific mutagenesis in vitro or by somatic mutation in vivo), for example, in the CDRs and, in particular, CDR3.

In various embodiments, the antibody is a recombinant antibody or a monoclonal antibody. The most preferred neutralizing antibodies of the present application are referred to herein as mAb5F9 and mAb8D1 and functional antibody fragments thereof, and other antibodies and functional antibody fragments with equivalent properties to mAb5F9 and mAb8D1, such as high affinity binding to RGM A with low dissociation kinetics and high neutralizing capacity, are intended as part of the present invention. The binding affinity and dissociation rate of an anti-RGM A antibody of the present application to an immunogenic RGM A polypeptide or fragment thereof, may be determined by any method known in the art. For example, the binding affinity can be measured by competitive ELISAs, c RIAs, BIAcore or KinExA technology. The dissociation rate also can be measured by BIAcore or KinExA technology. The binding affinity and dissociation rate are measured by surface plasmon resonance using, e.g., a BIAcore.

One of the preferred monoclonal antibodies of the present application, the mAb5F9 antibody, has at least 90% amino acid sequence identity with a sequence comprising a heavy chain variable region (VH region) comprising the sequence of SEQ ID NO: 9 or 34 and a light chain variable region (VL region) comprising the sequence of SEQ ID NO: 10.

It is also intended that the isolated monoclonal antibodies that interact with RGM A of the present application may be a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Protein glycosylation depends on the amino acid sequence of the protein of interest, as well as the host cell in which the protein is expressed. Different organisms may produce different glycosylation enzymes (eg., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

The antibodies of the present application comprise a heavy chain constant region, such as an IgG1, IgG2, IgG3, IgG4, IgA, IgE, IgM, IgY or IgD constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment. Replacements of amino acid residues in the Fc portion to alter antibody effector's function are known in the art (Winter, et al. U.S. Pat. Nos. 5,648,260; 5,624,821). The Fc portion of an antibody mediates several important effector's functions e.g. cytokine induction, ADCC, phagocytosis, complement dependent cytotoxicity (CDC) and half-life/clearance rate of antibody and antigen-antibody complexes. In some cases these effector's functions are desirable for therapeutic antibody but in other cases might be unnecessary or even deleterious, depending on the therapeutic objectives. Certain human IgG isotypes, particularly IgG1 and IgG3, mediate ADCC and CDC via binding to Fcγ R5 and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector's functions of the antibody are altered.

3. Generation of Anti-hRGM A Antibodies
3.1. General

Antibodies of the application can be generated by immunization of a suitable host (e.g., vertebrates, including humans, mice, rats, sheep, goats, pigs, cattle, horses, reptiles, fishes, amphibians, and in eggs of birds, reptiles and fish). To generate the antibodies of the present application, the host is immunized with an immunogenic RGM A polypeptide or fragment thereof of the invention. The term "immunization" refers herein to the process of presenting an antigen to an immune repertoire whether that repertoire exists in a natural genetically unaltered organism, or a transgenic organism, including those modified to display an artificial human immune repertoire. Similarly, an "immunogenic preparation" is a formulation of antigen that contains adjuvants or other additives that would enhance the immunogenicity of the antigen.

Immunization of animals may be done by any method known in the art. See, e.g., Harlow and Lane, Antibodies: A Laboratory Manual, New York: Cold Spring Harbor Press, 1990. Methods for immunizing non-human animals such as mice, rats, sheep, goats, pigs, cattle and horses are well known in the art. See, e.g., Harlow and Lane and U.S. Pat. No. 5,994,619. In a preferred embodiment, the RGM A antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

It is contemplated that the animal host is immunized with the antigen associated with the cell membrane of an intact or disrupted cell and antibodies of the present application are identified by binding to an immunogenic polypeptide of the invention. After immunization of the animal host with the antigen, antibodies may be obtained from the animal. The antibody-containing serum is obtained from the animal by bleeding or sacrificing the animal. The serum may be used as it is obtained from the animal, an immunoglobulin fraction may be obtained from the serum, or the antibodies may be purified from the serum. Serum or immunoglobulins obtained in this manner are polyclonal, thus having a heterogeneous array of properties.

3.2 Anti-RGM A Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention. Briefly, mice can be immunized with an RGM A antigen. In a preferred embodiment, the RGM A antigen is administered with a adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

Once an immune response is detected, e.g., antibodies specific for the antigen RGM A are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding RGM A. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using RGM A, or a portion thereof, or a cell expressing RGM A. In a preferred embodiment, the initial screening is performed using an enzyme-linked immunoassay (ELISA) or a radioimmunoassay (RIA), preferably an ELISA. An example of ELISA screening is provided in WO 00/37504, herein incorporated by reference.

Anti-RGM A antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-RGM A antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

3.3 Anti-RGM A Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627, 052, PCT Publication WO 92/02551 and Babcock, J. S. et al. (1996) *Proc. Natl. Acad. Sci. USA* 93:7843-7848. In this method, single cells secreting antibodies of interest, e.g., lymphocytes derived from any one of the immunized animals described above, are screened using an antigen-specific hemolytic plaque assay, wherein the antigen RGM A, a subunit of RGM A, or a fragment thereof, is coupled to sheep red blood cells using a linker, such as biotin, and used to identify single cells that secrete antibodies with specificity for RGM A. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to RGM A. The amplified immunoglobulin sequences further can be manipulated in vitro, such as by in vitro affinity maturation methods such as those described in PCT Publication WO 97/29131 and PCT Publication WO 00/56772.

3.4 Anti-RGM A Monoclonal Antibodies Using Transgenic Animals

In another embodiment of the instant invention, antibodies are produced by immunizing a non-human animal comprising some, or all, of the human immunoglobulin locus with an RGM A antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771, 5,939,598, 5,985,615, 5,998,209, 6,075,181, 6,091,001, 6,114,598 and 6,130,364. See also WO 91/10741, published Jul. 25, 1991, WO 94/02602, published Feb. 3, 1994, WO 96/34096 and WO 96/33735, both published Oct. 31, 1996, WO 98/16654, published Apr. 23, 1998, WO 98/24893, published Jun. 11, 1998, WO 98/50433, published Nov. 12, 1998, WO 99/45031, published Sep. 10, 1999, WO 99/53049, published Oct. 21, 1999, WO 00 09560, published Feb. 24, 2000 and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germine configuration YAC fragments of the human heavy chain loci and x light chain loci. See Mendez et al., *Nature Genetics* 15:146-156 (1997), Green and Jakobovits *J. Exp. Med.* 188:483-495 (1998), the disclosures of which are hereby incorporated by reference.

3.5 Anti-RGM A Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with RGM A, or a portion of RGM A. Alternatively, the recombinant antibody library may be from a naïve subject, i.e., one who has not been immunized with RGM A, such as a human antibody library from a human subject who has not been immunized with human RGM A. Antibodies of the invention are selected by screening the recombinant antibody library with the peptide comprising human RGM A to thereby select those antibodies that recognize RGM A. Methods for conducting such screening and selection are well known in the art, such as described in the references in the preceding paragraph. To select antibodies of the invention having particular binding affinities for hRGM A, such as those that dissociate from human RGM A with a particular $k_{off}$ rate constant, the art-known method of surface plasmon resonance can be used to select antibodies having the desired $k_{off}$ rate constant. To select antibodies of the invention having a particular neutralizing activity for hRGM A, such as those with a particular an $IC_{50}$, standard methods known in the art for assessing the inhibition of hRGM A activity may be used.

In one aspect, the invention pertains to an isolated antibody, or an antigen-binding portion thereof, that binds human RGM A. Preferably, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties). Examples of techniques, which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) Proc. Natl. Acad. Sci. USA 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup, et al. U.S. Pat. No. 6,699,658 incorporated herein by reference.

4. Production of Particular Recombinant Rgm A Antibodies of the Invention

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

4.1 Anti RGM A Antibodies

Table 5 is a list of amino acid sequences of VH and VL regions of preferred anti-hRGM A antibodies of the invention.

TABLE 5

LIST OF AMINO ACID SEQUENCES OF VH AND VL
REGIONS OF ANTI hRGM A ANTIBODIES 5F9 AND 8D1

| SEQ ID No. | Protein region | | Sequence 12345678901234567890123456789 0 |
|---|---|---|---|
| 34 | VH 5F9 | | EVQLVESGGGLVQPGSSLKLSCVASGFTFS NYGMNWIRQAPKKGLEWIGMIYYDSSEKHY ADSVKGRFTISRDNSKNTLYLEMNSLRSED TAIYYCAKGTTPDYWGQGVMVTVSS |
| 57 | VH 5F9 | CDR-H1 Residues 31-35 of SEQ ID NO.: 34 | NYGMN |
| 58 | VH 5F9 | CDR-H2 Residues 50-66 of SEQ ID NO.: 34 | MIYYDSSEKHYADSVKG |
| 59 | VH 5F9 | CDR-H3 Residues 99-104 of SEQ ID NO.: 34 | GTTPDY |
| 10 | VL 5F9 | | DVVLTQTPVSLSVTLGDQASMSCRSSQSLE YSDGYTFLEWFLQKPGQSPQLLIYEVSNRF SGVPDRFIGSGSGTDFTLKISRVEPEDLGV YYCFQATHDPLTFGSGTKLEIKR |
| 60 | VL 5F9 | CDR-L1 Residues 24-39 of SEQ ID NO.: 10 | RSSQSLEYSDGYTFLE |
| 61 | VL 5F9 | CDR-L2 Residues 55-61 of SEQ ID NO.: 10 | EVSNRFS |
| 62 | VL 5F9 | CDR-L3 Residues 94-102 of SEQ ID NO.: 10 | FQATHDPLT |
| 55 | VH 8D1 | | EVQLQQSGPELVKPGTSVKMSCKTSGYTFT SYVMHWVKQKPGQGLEWIGYIIPYNDNTKY NEKFKGKATLTSDKSSSTAYMELSSLTSED |

TABLE 5-continued

LIST OF AMINO ACID SEQUENCES OF VH AND VL
REGIONS OF ANTI hRGM A ANTIBODIES 5F9 AND 8D1

| SEQ ID No. | Protein region | | Sequence<br>123456789012345678901234567890 |
|---|---|---|---|
| | | | SAVYYCARRNEYYGSSFFDYWGQGTTLTVSS |
| 63 | VH 8D1 | CDR-H1 Residues 31-35 of SEQ ID NO.: 55 | SYVMH |
| 64 | VH 8D1 | CDR-H2 Residues 50-66 of SEQ ID NO.: 55 | YIIPYNDNTKYNEKFKG |
| 65 | VH 8D1 | CDR-H3 Residues 97-110 of SEQ ID NO.: 55 | ARRNEYYGSSFFDY |
| 56 | VL 8D1 | | DIQMTQSPASLSASLEEIVTITCQASQDIDNYLAWYHQKPGKSPRLLIYGATNLADGVPSRFSGSRSGTQFSLKINRLQIEDLGIYYCLQGYIPPRTFGGGTKLELKR |
| 66 | VL 8D1 | CDR-L1 Residues 24-34 of SEQ ID NO.: 56 | QASQDIDNYLA |
| 67 | VL 8D1 | CDR-L2 Residues 50-56 of SEQ ID NO.: 56 | GATNLAD |
| 68 | VL 8D1 | CDR-L3 Residues 89-97 of SEQ ID NO.: 56 | LQGYIPPRT |

The foregoing isolated anti-RGM A antibody CDR sequences establish a novel family of RGM A binding proteins, isolated in accordance with this invention. To generate and to select CDR's of the invention having preferred RGM A binding and/or neutralizing activity with respect to hRGM A, standard methods known in the art for generating binding proteins of the present invention and assessing the RGM A binding and/or neutralizing characteristics of those binding protein may be used, including but not limited to those specifically described herein.

4.2 Anti RGM A Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454 which are incorporated herein by reference in their entireties) by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the murine monoclonal anti human RGM A antibodies described herein with a human IgG1 constant region.

4.3 Anti RGM A CDR Grafted Antibodies

CDR-grafted antibodies of the invention comprise heavy and light chain variable region sequences from a human antibody wherein one or more of the CDR regions of $V_H$ and/or $V_L$ are replaced with CDR sequences of non-human, as for example murine antibodies of the invention. A framework sequence from any human antibody may serve as the template for CDR grafting. However, straight chain replacement onto such a framework often leads to some loss of binding affinity to the antigen. The more homologous a human antibody is to the original murine antibody, the less likely the possibility that combining the murine CDRs with the human framework will introduce distortions in the CDRs that could reduce affinity. Therefore, it is preferable that the human variable framework that is chosen to replace the murine variable framework apart from the CDRs have at least a 65% sequence identity with the murine antibody variable region framework. It is more preferable that the human and murine variable regions apart from the CDRs have at least 70% sequence identify. It is even more preferable that the human and murine variable regions apart from the CDRs have at least 75% sequence identity. It is most preferable that the human and murine variable regions apart from the CDRs have at least 80% sequence identity. Methods for producing CDR-grafted antibodies are known in the art (Jones et al., Nature 321:522-525 (1986); U.S. Pat. Nos. 5,225,539). In a specific embodiment the invention provides CDR grafted antibodies with $V_H$ and/or $V_L$ chains as described in Table 6.

TABLE 6

CDR GRAFTED ANTIBODIES

| SEQ ID No. | Protein region | Sequence 123456789012345678901234567890 |
|---|---|---|
| 35 | VH 5F9.1-GL | |
| (15) | (VH3-48/ JH3 FR1) | EVQLVESGGGLVQPGGSLRLSCAASGFTFS |
| (16) | (VH3-48/ JH3 FR2) | NYGMNWVRQAPGKGLEWVSMIYYDSSEKHY |
| (17) | (VH3-48/ JH3 FR3) | ADSVKGRFTISRDNAKNSLYLQMNSLRDED |
| (18) | (VH3-48/ JH3 FR4) | TAVYYCARGTTPDYWGQGTMVTVSS |
| 36 | VH 5F9.2-GL | |
| (15) | (VH3-48/ JH4 FR1) | EVQLVESGGGLVQPGGSLRLSCAASGFTFS |
| (16) | (VH3-48/ JH4 FR2) | NYGMNWVRQAPGKGLEWVSMIYYDSSEKHY |
| (17) | (VH3-48/ JH4 FR3) | ADSVKGRFTISRDNAKNSLYLQMNSLRDED |
| (19) | (VH3-48/ JH4 FR4) | TAVYYCARGTTPDYWGQGTLVTVSS |
| 37 | VH 5F9.3-GL | |
| (15) | (VH3-48/ JH6 FR1) | EVQLVESGGGLVQPGGSLRLSCAASGFTFS |
| (16) | (VH3-48/ JH6 FR2) | NYGMNWVRQAPGKGLEWVSMIYYDSSEKHY |
| (17) | (VH3-48/ JH6 FR3) | ADSVKGRFTISRDNAKNSLYLQMNSLRDED |
| (20) | (VH3-48/ JH6 FR4) | TAVYYCARGTTPDYWGQGTTVTVSS |
| 38 | VH 5F9.4-GL | |
| (21) | (VH3-33/ JH3 FR1) | QVQLVESGGGVVQPGRSLRLSCAASGFTFS |
| (22) | (VH3-33/ JH3 FR2) | NYGMNWVRQAPGKGLEWVAMIYYDSSEKHY |
| (23) | (VH3-33/ JH3 FR3) | ADSVKGRFTISRDNSKNTLYLQMNSLRAED |
| (18) | (VH3-33/ JH3 FR4) | TAVYYCARGTTPDYWGQGTMVTVSS |
| 39 | VH 5F9.5-GL | |
| (21) | (VH3-33/ JH4 FR1) | QVQLVESGGGVVQPGRSLRLSCAASGFTFS |
| (22) | (VH3-33/ JH4 FR2) | NYGMNWVRQAPGKGLEWVAMIYYDSSEKHY |
| (23) | (VH3-33/ JH4 FR3) | ADSVKGRFTISRDNSKNTLYLQMNSLRAED |
| (19) | (VH3-33/ JH4 FR4) | TAVYYCARGTTPDYWGQGTLVTVSS |
| 40 | VH 5F9.6-GL | |
| (21) | (VH3-33/ JH6 FR1) | QVQLVESGGGVVQPGRSLRLSCAASGFTFS |
| (22) | (VH3-33/ JH6 FR2) | NYGMNWVRQAPGKGLEWVAMIYYDSSEKHY |
| (23) | (VH3-33/ JH6 FR3) | ADSVKGRFTISRDNSKNTLYLQMNSLRAED |
| (20) | (VH3-33/ JH6 FR4) | TAVYYCARGTTPDYWGQGTTVTVSS |
| 41 | VH 5F9.7-GL | |
| (24) | (VH3-23/ JH3 FR1) | EVQLLESGGGLVQPGGSLRLSCAASGFTFS |
| (25) | (VH3-23/ JH3 FR2) | NYGMNWVRQAPGKGLEWVSMIYYDSSEKHY |
| (26) | (VH3-23/ JH3 FR3) | ADSVKGRFTISRDNSKNTLYLQMNSLRAED |
| (18) | (VH3-23/ JH3 FR4) | TAVYYCAKGTTPDYWGQGTMVTVSS |
| 42 | VH 5F9.8-GL | |
| (24) | (VH3-23/ JH4 FR1) | EVQLLESGGGLVQPGGSLRLSCAASGFTFS |
| (25) | (VH3-23/ JH4 FR2) | NYGMNWVRQAPGKGLEWVSMIYYDSSEKHY |
| (26) | (VH3-23/ JH4 FR3) | ADSVKGRFTISRDNSKNTLYLQMNSLRAED |
| (19) | (VH3-23/ JH4 FR4) | TAVYYCAKGTTPDYWGQGTLVTVSS |
| 43 | VH 5F9.9-GL | |
| (24) | (VH3-23/ JH6 FR1) | EVQLLESGGGLVQPGGSLRLSCAASGFTFS |
| (25) | (VH3-23/ JH6 FR2) | NYGMNWVRQAPGKGLEWVSMIYYDSSEKHY |
| (26) | (VH3-23/ JH6 FR3) | ADSVKGRFTISRDNSKNTLYLQMNSLRAED |
| (20) | (VH3-23/ JH6 FR4) | TAVYYCAKGTTPDYWGQGTTVTVSS |
| 44 | VL 5F9.1-GL | |
| (27) | (A18/JK2 FR1) | DIVMTQTPLSLSVTPGQPASISCRSSQSLE |
| (28) | (A18/JK2 FR2) | YSDGYTFLEWYLQKPGQSPQLLIYEVSNRF |
| (29) | (A18/JK2 FR3) | SGVPDRFSGSGSGTDFTLKISRVEAEDVGV |
| (30) | (A18/JK2 FR4) | YYCFQATHDPLTFGQGTKLEIKR |
| 45 | VL 5F9.2-GL | |
| (31) | (A17/JK2 FR1) | DVVMTQSPLSLPVTLGQPASISCRSSQSLE |
| (32) | (A17/JK2 FR2) | YSDGYTFLEWFQQRPGQSPRRLIYEVSNRF |
| (33) | (A17/JK2 FR3) | SGVPDRFSGSGSGTDFTLKISRVEAEDVGV |
| (30) | (A17/JK2 FR4) | YYCFQATHDPLTFGQGTKLEIKR |
| 46 | VL 5F9.3-GL | |
| (31) | (A17/JK2 FR1) | DVVMTQSPLSLPVTLGQPASISCRSSQSLE |
| (28) | (A18/JK2 FR2) | YSDGYTFLEWYLQKPGQSPQLLIYEVSNRF |
| (29) | (A18/JK2 FR3) | SGVPDRFSGSGSGTDFTLKISRVEAEDVGV |
| (30) | (A18/JK2 FR4) | YYCFQATHDPLTFGQGTKLEIKR |

CDR sequences derived from mAb 5F9 are stated in bold letters. reference is also made to the specific framework sequences (FR1 to FR4) by stating the corresponding SEQ ID Nos (see also Tables 3 and 4)

4.4 Anti RGM A Humanized Antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., Kabat et al., Sequences of Proteins of Immunological Interest, U.S. Dept. Health (1983), entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766886, 5,714,352, 6,204,023, 6,180,370, 5,693,762, 5,530,101, 5,585,089, 5,225,539; 4,816,567, each entirely incorporated herein by reference, included references cited therein.

5. Further Embodiments of Antibodies of the Invention
5.1 Fusion Antibodies and Immunoadhesins The present application also describes a fusion antibody or immunoadhesin that may be made which comprises all or a portion of a RGM A antibody of the present application linked to another polypeptide. In some embodiments, only the variable region of the RGM A antibody is linked to the polypeptide. In other embodiments, the VH domain of a RGM A antibody of this application is linked to a first polypeptide, while the VL domain of the antibody is linked to a second polypeptide that associates with the first polypeptide in a manner that permits the VH and VL domains to interact with one another to form an antibody binding site. In other embodiments, the VH domain is separated from the VL domain by a linker that permits the VH and VL domains to interact with one another (see below under Single Chain Antibodies). The VH-linker-VL antibody is then linked to a polypeptide of interest. The fusion antibody is useful to directing a polypeptide to a cell or tissue that expresses a RGM A. The polypeptide of interest may be a therapeutic agent, such as a toxin, or may be a diagnostic agent, such as an enzyme; that may be easily visualized, such as horseradish peroxidase. In addition, fusion antibodies can be created in which two (or more) single-chain antibodies are linked to one another. This is useful if one wants to create a divalent or polyvalent antibody on a single polypeptide chain, or if one wants to create a bispecific antibody.

One embodiment provides a labelled binding protein wherein an antibody or antibody portion of the present application is derivatized or linked to another functional molecule (e.g., another peptide or protein). For example, a labelled binding protein of the present application can be derived by functionally linking an antibody or antibody portion of the present application (by chemical coupling, genetic fusion, noncovalent association or otherwise) to one or more other molecular entities, such as a nucleic acid, another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

Useful detectable agents with which an antibody or antibody portion of the present application may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with a nucleic acid, biotin, and detected through indirect measurement of avidin or streptavidin binding.

5.2 Single Chain Antibodies

The present application includes a single chain antibody (scFv) that binds an immunogenic RGM A of the invention. To produce the scFv, VH- and V-encoding DNA is operatively linked to DNA encoding a flexible linker, e.g., encoding the amino acid sequence (Gly-4-Ser), such that the VH and VL sequences can be expressed as a contiguous single-chain protein, with the VL and VH regions joined by the flexible linker (see e.g., Bird et al. (1988) Science 242:423-42 6; Huston et al. (1988) Proc. Natl. Acad. Sci. USA 85: 5879-5883; McCafferty et al., 30 Nature (1990) 34 8: 552-554). The single chain antibody may be monovalent, if only a single VH and VL are used, bivalent, if two VH and VL are used, or polyvalent, if more than two VH and VL are used. Two of said scFv fragments coupled via a linker are called "diabody" which form is also encompassed by the invention.

5.3 Bispecific Antibodies

The present application further includes a bispecific antibody or antigen-binding fragment thereof in which one specificity is for an immunogenic RGM A polypeptide of the present application. For example, a bispecific antibody can be generated that specifically binds to an immunogenic RGM A polypeptide of the invention through one binding domain and to a second molecule through a second binding domainIn addition, a single chain antibody containing more than one VH and VL may be generated that binds specifically to an immunogenic polypeptide of the invention and to another molecule that is associated with attenuating myelin mediated growth cone collapse and inhibition of neurite outgrowth and sprouting. Such bispecific antibodies can be generated using techniques that are well known for example, Fanger et al. Immunol Methods 4: 72-81 (1994) and Wright and Harris, (supra).

In some embodiments, the bispecific antibodies are prepared using one or more of the variable regions from an antibody of the invention. In another embodiment, the bispecific antibody is prepared using one or more CDR regions from said antibody.

5.4 Derivatized and Labeled Antibodies

An antibody or an antigen-binding fragment of the present application can be derivatized or linked to another molecule (e.g., another peptide or protein). In general, the antibody or antigen-binding fragment is derivatized such that binding to an immunogenic polypeptide of the invention is not affected adversely by the derivatization or labeling.

For example, an antibody or antibody portion of the present application can be functionally linked (by chemical coupling, genetic fusion, noncovalent association or otherwise) to one or more other molecular entities, such as another antibody (e.g., a bispecific antibody or a diabody), a detection reagent, a cytotoxic agent, a pharmaceutical agent, and/or a protein or peptide that can mediate association of the antibody or antigen-binding fragment with another molecule (such as a streptavidin core region or a polyhistidine tag). Still further, an antibody or antigen-binding portion thereof may be part of a larger immunoadhesion molecule, formed by covalent or non-covalent association of the antibody or antibody portion with one or more other or different proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Molecular Immunology 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques.

A derivatized antibody may be produced by crosslinking two or more antibodies (of the same type or of different types, e.g., to create bispecific antibodies). Suitable crosslinkers include those that are heterobifunctional, having two distinctly reactive groups separated by an appropriate spacer (e.g. m-maleimidobenzoyl-N-hydroxysuccinimide ester) or homobifunctional (e.g., disuccinimidyl suberate). Such linkers are available from Pierce Chemical Company, Rockford, Ill.

A derivatized antibody may also be a labeled antibody. For instance, detection agents with which an antibody or antibody portion of the invention may be derivatized are fluorescent compounds, including fluorescein, fluorescein isothiocyanate, rhodamine, 5-dimethylamine-1-naphthalenesulfonyl chloride, phycoerythrin, lanthanide phosphors and the like. An antibody also may be labeled with enzymes that are useful for detection, such as horseradish peroxidase, galactosidase, luciferase, alkaline phosphatase, glucoseoxidase and the like. In embodiments that are labeled with a detectable enzyme, the antibody is detected by adding additional reagents that the enzyme uses to produce a detectable reaction product. For example, horseradish peroxidase with hydrogen peroxide and diaminobenzidine. An antibody also may be labeled with biotin, and detected through indirect measurement of avidin or streptavidin binding. An antibody may also be labeled with a predetermined polypeptide epitope recognized by a secondary reporter (e.g., leucine zipper pair sequences, binding sites for secondary antibodies, metal binding domains, epitope: tags). An RGM A antibody or an antigen fragment thereof also may be labeled with a radio-labeled amino acid. The radiolabel may be used for both diagnostic and therapeutic purposes. The radio-labeled RGM A antibody may be used diagnostically, for example, for determining RGM A receptor levels in a subject. Further, the radio-labeled RGM A antibody may be used therapeutically for treating spinal cord injury.

Examples of labels for polypeptides include, but are not limited to, the following radioisotopes or radionucleotides $^{15}$N, $^{35}$S, $^{90}$Y, $^{99}$Tc, $^{111}$In, $^{125}$I, $^{131}$I, $^{177}$Lu, $^{166}$Ho, $^{153}$Sm. A RGM A antibody or an antigen fragment thereof may also be derivatized with a chemical group such as polyethylene glycol (PEG), a methyl or ethyl group, or a carbohydrate group. These groups may be useful to improve the biological characteristics of the antibody, e.g., to increase serum half-life or to increase tissue binding. Also, a label for polypeptides can include a nucleic acid, for example DNA for detection by PCR, or enhancing gene expression, or siRNA to suppress gene expression in RGM A-bearing cells or tissues.

The class and subclass of RGM A antibodies may be determined by any method known in the art. In general, the class and subclass of an antibody may be determined using antibodies that are specific for a particular class and subclass of antibody. Such antibodies are available commercially. The class and subclass can be determined by ELISA, Western Blot as well as other techniques. Alternatively, the class and subclass may be determined by sequencing all or a portion of the constant domains of the heavy and/or light chains of the antibodies, comparing their amino acid sequences to the known amino acid sequences of various classes and subclasses of immunoglobulins, and determining the class and subclass of the antibodies.

5.5 Dual Variable Domain Immunoglobulins

Dual variable domain (DVD) binding proteins or immunoglobulins as used herein, are binding proteins that comprise two or more antigen binding sites and are multivalent binding proteins, as for example divalent and tetravalent. The term "multivalent binding protein" is used in this specification to denote a binding protein comprising two or more antigen binding sites. The multivalent binding protein is preferably engineered to have the two or more antigen binding sites, and is generally not a naturally occurring antibody. The term "multispecific binding protein" refers to a binding protein capable of binding two or more related or unrelated targets. Such DVDs may be monospecific, i.e capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. DVD binding proteins and methods of making DVD binding proteins are disclosed in U.S. patent application Ser. No. 11/507,050 and incorporated herein by reference. It is intended that the present invention comprises a DVD binding protein comprising binding proteins capable of binding RGM A. Preferably the DVD binding protein is capable of binding RGM A and a second target. The second target is selected from the group consisting of anti inflammatory MAB activities (IL-1, IL-6, IL-8, IL-11, IL-12, IL-17, IL-18, IL-23,TNF alpha/beta, IFN-beta, gamma, LIF, OSM, CNTF, PF-4, Platelet basic protein (PBP), NAP-2, beta-TG, MIP-1, MCP2/3, RANTES, lymphotactin), of transport-mediating proteins (insulin receptor, transferrin receptor, thrombin receptor, leptin receptor, LDL receptor), of other neuroregenerative MABs (NgR, Lingo, p75, CSPG (e.g. NG-2, neurocan, brevican, versican, aggrecan) hyaluronic acid, mAG, tenascin, NI-35, NI-250, IMP, perlecan, neurocan, phosphacan, nogo-A, OMGP, Sema4D, Sema 3A, ephrin B3, ephrin A2, ephrin A5, MAG, EphA4,plexin B1, TROY, wnts, ryk rec., BMP-2, BMP-4, BMP-7), of neuroprotective MAB activities (EGF, EGFR, Sema 3), of anti-amyloid beta MABs (e.g. m266, 3D6 (bapineuzumab), anti-globulomer MABs 7C6), of CNS located receptors and transporters (serotonin receptors, dopamine receptors, DAT, Asc-1, GlyT1).

5.6 Dual-Specific Antibodies

The present application also describes "dual-specific antibody" technology. Dual-specific antibodies may serve as agonists, antagonists, or both in different combinations. Dual-specific antibodies are antibodies in which the VH chain binds to a first antigen and the VL chain binds to another antigen as exemplified in WO2008082651.

5.7 Crystallized Antibodies

Another embodiment of the present application provides a crystallized binding protein. The term "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, $2^{nd}$ ed., pp. 201-16, Oxford University Press, New York, N.Y., (1999).

Preferably the present application describes crystals of whole RGM A antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in WO 02072636, incorporated herein by reference.

5.8 Glycosylated Antibodies

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., Mol. Immunol. (1993) 30:1361-1367), or result in increased affinity for the antigen (Wallick, S. C., et al., Exp. Med. (1988) 168:1099-1109; Wright, A., et al., EMBO J. (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity but have increased or decreased binding activity are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (eg., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S patent applications 20040018590 and 20020137134 and PCT publication WO2005100584 A2).

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties

5.9 Anti-Idiotypic Antibodies

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

6. Uses of the Antibodies

Given their ability to bind to human RGM A, the neutralizing antibodies of the present application, or portions thereof, can be used to detect human RGM A (e.g., in a biological sample, such as serum or plasma), using a conventional immunoassay, such as an enzyme linked immunosorbent assays (ELISA), a radioimmunoassay (RIA) or tissue immunohistochemistry. The present application provides a method for detecting human RGM A in a biological sample comprising contacting a biological sample with an antibody, or antibody portion, of the invention and detecting either the antibody (or antibody portion) bound to human RGM A or unbound antibody (or antibody portion), to thereby detect human RGM A in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, $^{153}Sm$.

The antibodies and antibody portions of the present application preferably are capable of neutralizing human RGM A activity both in vitro and in vivo. Accordingly, such antibodies and antibody portions of the invention can be used to inhibit RGM A binding to its receptor Neogenin, to BMP-2, and or BM-4, and therefore inhibit the resulting activity.

In another embodiment, the present application provides a method for reducing RMG A activity in a subject, advantageously from a subject suffering from a disease or disorder in which RGM A resulting activity is detrimental. The present application provides methods for reducing RGM A activity in a subject suffering from such a disease or disorder, by preventing RGM A binding to Neogenin, and/or BMP-2, and/or BMP-4, through the use of the monoclonal antibodies of the present application. The antibodies of the present application, in particular the humanized antibodies disclosed herein, can be administered to a human subject for therapeutic purposes. Moreover, the antibodies of the present application can be administered to a non-human mammal expressing an RGM A with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which RGM A activity is detrimental" is intended to include diseases and other disorders in which the presence of RGM A or its resulting activity in a subject suffering from the disorder has been shown to be or is suspected of being either responsible for the pathophysiology of the disorder or a factor that contributes to a worsening of the disorder. Accordingly, a disorder in which RGM A activity is detrimental is a disorder in which reduction of RGM A activity is expected to alleviate the symptoms and/or progression of the disorder. Non-limiting examples of disorders that can be treated with the antibodies of the invention include those disorders discussed in the section below pertaining to pharmaceutical compositions of the antibodies of the invention.

It is recognized that RGM A plays an important role in the pathology associated with a variety of diseases involving neurological diseases associated with neurodegeneration or inhibition of neuroregenerative processes, resulting in paralysis. This includes dementia, senile dementia, mild cognitive impairment, Alzheimer-related dementia, Huntington's chorea, tardive dyskinesia, hyperkinesias, manias, Morbus Parkinson, Steel-Richard syndrome, Down's syndrome, myasthenia gravis, nerve trauma, vascular amyloidosis, cerebral hemorrhage I with amyloidosis, brain inflammation, Friedrich's ataxia, acute confusion disorder, glaucoma, Alzheimer's disease, Amyotrophic Lateral Sclerosis, Brachial Plexus Injury, Brain Injury, including traumatic brain injury, Cerebral Palsy, Guillain Barre, Leukodystrophies, Multiple Sclerosis, Post Polio, Spina Bifida, Spinal Cord Injury, Spinal Muscle Atrophy, Spinal Tumors, Stroke, and Transverse Myelitis.

Also, as previously discussed, DVD immunoglobulins, or dual-specific antibodies between any one of the partners described above may be of use. Such antibody preparations as described above may be useful for the treatment of Alzheimer's disease, Parkinson's disease, spinal cord injury, traumatic brain injury, multiple sclerosis, peripheral nerve injury, schizophrenia, depression, anxiety, as well as any plasticity and neurite growth and neurotoxicity related disease cited above.

The antibodies of the present application may also be combined with peptides allowing the trans-membrane transfer to include targeting of intracellular target proteins. Such peptide sequences may include, but are not limited to, tat, antennapedia, poly-arginins, some anti-microbial peptides. Such peptides may allow transfer through membranes, including cellular plasma membranes, but also epithelia and endothelial membranes, including the blood-brain-barrier, gut mucosa, meninges, and others.

An antibody, or antibody portion, of the present application also can be administered with one or more additional small molecule therapeutic agents useful in the treatment of disorders in which RGM A activity is involved as discussed in the foregoing paragraphs. It should be understood that the antibodies of the present application or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent that affects the viscosity of the composition.

7. Pharmaceutical Compositions

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which RGM A activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tisseel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912, 015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotheraphy of a Human Colon Cancer Xenograft Using a Sustained-Release Gel," Radiotherapy &Oncology 39:179-189, Song et al., 1995, "Antibody Mediated Lung Targeting of Long-Circulating Emulsions," PDA Journal of Pharmaceutical Science &Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, US2006104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which RGM A activity is detrimental. For example, an anti-RGM A antibody or antibody portion of the invention may be coformulated and/or coadministered with one or more additional antibodies that bind other targets (e.g., antibodies that bind cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to RGM A or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley &Sons, NY (1993); and Kriegler, Gene Transfer and Expression, A Laboratory Manual, Stockton Press, NY (1990). Detailed description of various methods of gene therapy are disclosed in US20050042664 A1 which is incorporated herein by reference.

RGM A plays a critical role in the pathology associated with a variety of diseases as defined herein above. RGM A and RGM proteins have been described to be up-regulated at lesion sites in humans suffering from traumatic brain injury (Schwab et al., Arch. Neurol. 62: 1561-8, 2005a) in infarcted penumbra and core areas of the stroke-damaged human brain (Schwab et al., Arch. Neurol. 62: 1561-8, 2005a), in the substantia nigra of patients suffering from Parkinson's disease (Bossers et al. Brain Pathology vol. 19: 91-107, 2008). Therefore RGM A antibodies are suitable agents for combinatorial therapy of cerebral stroke, traumatic brain injury, Parkinson's disease, Alzheimer's disease and other neurodegenerative disorders of the human nervous system. In stroke patients current treatment within the first three hours consists of delivery of tissue plasminogen activator for lysis of blood clots (Liang et al. Arch. Neurol. 65: 1429-33, 2008) and such a treatment could in principle be combined with an RGM A antibody delivery which offers a different treatment approach and a far more extended therapeutic window. In Alzheimer's disease, drug combination with RGMA antibodies is possible with the approved cognition enhancers, Donepezil, Memantine and such an approach might significantly slow down the progressive neuropathology. Intranasal delivery of insulin has positive effects on attention and memory (Hanson and Frey, BMC Neurosci. 9: S5, 2008) and is a possible administration route for RGM A antibodies thereby bypassing the blood-brain-barrier. In Parkinson disease (PD) patients, current treatment is based mainly on dopaminergic agents like levodopa, a dopamine prodrug (Khor and Hsu, Curr. Clin. Pharmacol. 2: 234-43, 2007), ropinirole, a non-ergolinic dopamine agonist (Jost et al. J. Neurol. 255 Suppl. 5: 60-63, 2008), the monoamine oxidase B inhibitors Rasagiline and Selegiline (Elmer and Bertoni, Expert Opin. Pharmacother. 9: 2759-72, 2008). Despite their beneficial effects in early and mild PD none of these drugs is able to prevent the progressive degeneration of the substantia nigra and associated subcortical and cortical brain areas and a combination therapy with regeneration-stimulating RGM A antibodies could therefore slow down the disease process.

Any neuroprotective agent being it an antioxidant, a radical scavengers, an anti-convulsive drug like Phenyloin or the anemia drug Erythropoietin is suitable for a combinatorial therapy with pro-regenerative RGM A antibodies thereby extending the usually very short therapeutic treatment window of the neuroprotectants.

The antibodies, and antibody portions of the invention can be used to treat humans suffering from such diseases.

It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent, which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

Non-limiting examples of therapeutic agents for multiple sclerosis with which an antibody, or antibody portion, of the invention can be combined include the following: corticosteroids; prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE; Teva Pharmaceutical Industries, Inc.); hyperbaric oxygen; intravenous immunoglobulin; cladribine; antibodies to or antagonists of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD19, CD20, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signalling by proinflammatory cytokines such as TNFα or IL-1 (e.g. IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sIL-1RI, sIL-1RII, sIL-6R) and antiinflammatory cytokines (e.g. IL-4, IL-10, IL-13 and TGFβ).

Preferred examples of therapeutic agents for multiple sclerosis in which the antibody or antigen binding portion thereof can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

The antibodies of the invention, or antigen binding portions thereof, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Methods

The following methods describe in detail the experimental procedures used in the Examples section.

(i) Direct binding ELISA plates were coated with hRGM A (R&D) at a concentration of 2 µg/mL in Carbonate buffer. The wells were then blocked with 2% Blocking solution (Bio-Rad) for 1 hour at room temperature. Biotinylated antibodies were serially diluted with a 1:5 dilution factor in 0.1% BSA/PBS down the plate and incubated for 1 hour at room temperature. The detection reagent was a 1:10,000 dilution of streptavidin-HRP in 0.1% BSA/PBS. Detection was done with a TMB reagent, which was stopped with 2N $H_2SO_4$ and OD was read at 450 nM.

(ii) FACS analysis. Stable transfectants of HEK293 cells overexpressing hRGM A or BAF3 cells overexpressing ratRGM A were subjected to staining with unlabelled 5F9 or 8D1 MABs for more than 15 minutes at 4° in 0.1% BSA/PBS buffer. Detection was carried out with a mouse anti-rat IgG PE antibody.

(iii) Solid phase ELISA assays for evaluating MAB 5F9 in hRGM A-neogenin binding assays.

ELISA plates (Immuno Plate Cert. Maxi Sorb. F96 NUNC, 439-454) were coated for 1 h at 37° C. with a concentration of 2.5 µg/ml of the extracellular domain of the His-tagged human Neogenin protein (concentration of stock solution: 30 µg/ml). After the incubation, unbound Neogenin was removed in 3 separate wash steps with PBS containing 0.02% Tween 20. Blocking of the Neogenin-coated plates was done by adding 200 µl per well of a 3% Bovine serum albumin (BSA), PBS, Tween 20 (0.02%) blocking solution. After incubation for 1 h at 37° C., the blocking solution was removed and RGM A fragments or full length protein, conjugated with a human fc tag, with or without antibody, was added. In some experiments antibodies were preincubated with the fc-conjugated hRGM A proteins for 1 h at room temperature. The Neogenin-coated plates were incubated with hRGM A with or without antibodies for 1 h at 37° C. After 3 wash steps with PBS-Tween 20 (0.02%), plates were incubated with a Biotin-labeled anti-human fc antibody (1 mg/ml, diluted 1:200 in PBS containing 0.6% BSA, 0.02% Tween 20), Jackson ImmunoResearch catalog no: 709-065-149, for 1 h at 37° C. Unbound antibody was removed by 3 wash steps with PBS-Tween 20 (0.02%). To visualize binding of the Biotin-labeled anti-fc antibody, a complex consisting of Streptavidin-Peroxidase (Roche, cat. # 11089153001), diluted 1:5000 with PBS containing 0.6% BSA, 0.02% Tween 20 was added, followed by incubation at 37° C. for 1 h. Unbound Peroxidase-complex was removed in 3 subsequent wash steps (PBS-Tween 20 (0.02%) before adding the Peroxidase substrate (Immuno Pure TMB, Pierce # 34021). The substrate reaction was stopped 1-30 min after its addition to the wells by 2.5 M $H_2SO_4$. Plates were analysed (OD determination) at a wave length of 450 nm using an Anthos photometer.

(iv) Solid phase ELISA assays for evaluating MAB 5F9 in hRGM A-BMP-4 binding assays.

ELISA plates (Immuno Plate Cert. Maxi Sorb. F96 NUNC, 439454) were coated for 1 h at 37° C. with a solution containing a concentration of 2.5 µg/ml of recombinant human BMP-4 protein (R&D Systems, # 314-BP, Lot # BEM316061). After the incubation, unbound BMP-4 was removed in 3 separate wash steps with PBS containing 0.02% Tween 20. Blocking of the BMP-4 coated plates was done by adding 200 µl per well of a 3% Bovine serum albumin (BSA), PBS, Tween 20(0.02%) blocking solution. After incubation for 1 h at 37° C., the blocking solution was removed and RGM A fragments or full length protein, conjugated with a human fc tag, with or without antibody, was added. In some experiments antibodies were preincubated with the fc-conjugated hRGM A proteins for 1 h at room temperature. The BMP-4 coated plates were incubated with hRGM A with or without antibodies for 1 h at 37° C. After 3 wash steps with PBS-Tween 20 (0.02%), plates were incubated with a Biotin-labeled anti-human fc antibody (1 mg/ml, diluted 1:200 in PBS containing 0.6% BSA, 0.02% Tween 20), Jackson ImmunoResearch catalog no: 709-065-149, for 1 h at 37° C. Unbound antibody was removed by 3 wash steps with PBS-Tween 20 (0.02%). To visualize binding of the Biotin-labeled anti-fc antibody, a complex consisting of Streptavidin-Peroxidase (Roche, cat. # 11089153001), diluted 1:5000 with PBS containing 0.6% BSA, 0.02% Tween 20 was added, followed by incubation at 37° C. for 1 h. Unbound Peroxidase-complex was removed in 3 subsequent wash steps (PBS-Tween 20 (0.02%) before adding the Peroxidase substrate (Immuno Pure TMB, Pierce # 34021). The substrate reaction was stopped 1-30 min after its addition to the wells by 2.5 M $H_2SO_4$. Plates were analysed (OD determination) at a wave length of 450 nm using an Anthos photometer.

(v) Solid phase ELISA assays for evaluating MAB 5F9 in hRGM A-BMP-2 binding assays.

ELISA plates (Immuno Plate Cert. Maxi Sorb. F96 NUNC, 439454) were coated for 1 h at 37° C. with a solution containing a concentration of 2.5 µg/ml of recombinant human BMP-2 protein (R&D Systems, # 355-BM, Lot # MSA04). After the incubation, unbound BMP-2 was removed in 3 separate wash steps with PBS containing 0.02% Tween 20. Blocking of the BMP-2 coated plates was done by adding 200 µl per well of a 3% Bovine serum albumin (BSA), PBS, Tween 20(0.02%) blocking solution. After incubation for 1 h at 37° C., the blocking solution was removed and RGM A fragments or full length protein, conjugated with a human fc tag, with or without antibody, was added. In some experiments antibodies were preincubated with the fc-conjugated hRGM A proteins for 1 h at room temperature. The BMP-2 coated plates were incubated with hRGM A with or without antibodies for 1 h at 37° C. After 3 wash steps with PBS-Tween 20 (0.02%), plates were incubated with a Biotin-labeled anti-human fc antibody (1 mg/ml, diluted 1:200 in PBS containing 0.6% BSA, 0.02% Tween 20), Jackson ImmunoResearch catalog no: 709-065-149, for 1 h at 37° C. Unbound antibody was removed by 3 wash steps with PBS-Tween 20 (0.02%). To visualize binding of the Biotin-labeled anti-fc antibody, a complex consisting of Streptavidin-Peroxidase (Roche, cat. # 11089153001), diluted 1:5000 with PBS containing 0.6% BSA, 0.02% Tween 20 was added, followed by incubation at 37° C. for 1 h. Unbound Peroxidase-complex was removed in 3 subsequent wash steps (PBS-Tween 20 (0.02%) before adding the Peroxidase substrate (Immuno Pure TMB, Pierce # 34021). The substrate reaction was stopped 1-30 min after its addition to the wells by 2.5 M $H_2SO_4$. Plates were analysed (OD determination) at a wave length of 450 nm using an Anthos photometer.

(vi) Ntera-2 cell culture

Human Ntera-2 cells were obtained from the German Collection of Microorganisms and Cell Cultures (DMSZ, Braunschweig). Frozen stocks of undifferentiated Ntera-2 cells were thawed in DMEM medium containing 10% fetal bovine serum (FBS; JRH Bioscience, Kansas, USA) and 5% horse serum (HS; Sigma, Germany). Cells were grown in culture flasks (Greiner, Germany) until they reached confluence of 80%.

For neuronal differentiation, Ntera-2 cells were seeded at a density of $2.5 \times 10^6$ cells/175 cm² in differentiation medium (DMEM medium containing 10% FBS, 5% HS, 1% penicillin-streptomycin, retinoic acid 10 µM). Cells were differentiated for 3 weeks and the medium was exchanged twice a week.

After differentiation, cells were detached with trypsin-EDTA and split at a ratio of 1:6. 48 h later neuronal cells were separated by tapping from the underlying cells. Dislodged cells were transferred for aggregation in new medium into new shaking culture flasks (Corning, USA). Differentiated Ntera-2 cells were allowed to aggregate under smooth horizontal shaking conditions at 37° C., for 24 h in Neurobasal medium (Gibco) supplemented with B27 (Gibco), glutamine (Gibco) and penicillin-streptomycin. Ntera-2 aggregates were seeded at a density of approximately 20-30 aggregates per cover slip in 24-well plates. The poly-lysine precoated cover slips were coated with laminin (20 µg/ml, Sigma) and with the recombinant fc-coupled human RGM A fragment #786 (amino acids 47-168) at a concentration of 10 µg/ml. After seeding, cultures were treated with the 5F9 MAB, added at three different concentrations (0.1 µg/ml; 1 µg/ml; 10 µg/ml) to the culture medium and were further incubated for 24 h at 37° C. in Neurobasal medium. Aggregates were then fixed in 4% paraformaldehyde (2 h, room temperature) and permeabilized by addition of 0.1% Triton X-100 in PBS (20 min. room temperature). For fluorescent staining cultures were blocked with PBS containing 1% BSA for 1 h at room temperature. After blocking Ntera cells were incubated with a mouse monoclonal antibody against β-tubulin isotype 3 (clone SDL3D10, Sigma # T8660) for 2 h at room temperature. Unbound antibody was removed by 3 different wash steps (5-15 min each) and Ntera cells were incubated with a Cy-3 conjugated Donkey anti-mouse antibody (Jackson ImmunoResearch Lot 62597), diluted 1:350 fold in PBS/ 0.5% BSA and 0.5 µg/ml bisbenzimide. Ater a 1 hour incubation, cultures were washed 3 times to remove unbound secondary antibody. For fluorescence microscopy, coverslips were embedded in Fluoromount G (Southern Biotech, Eching).

Images of Ntera-2 aggregates were acquired using a Zeiss Axiovert 200 fluorescence microscope and the outgrowth of the cultures was automatically analysed using an in-house image acquisition and analysis system. Automatic analysis of outgrowth was done with Image Pro Plus 4.5 and the statistical analysis of the data was performed with Graph Pad Prism 4. Outgrowth was normalized to control cultures grown in the absence of the human RGM A fragment #786.

(vii) SH-SY5Y culture.

SH-SY5Y cells (ATCC, CRL-2266) are human neuroblastoma cells derived from a metastatic brain tumor. These cells were grown in a medium consisting of 50% Earle's Balanced Salt Solution (Invitrogen Life Technologies, Cat. # 24010-043) and 50% F12 (Ham) Nutrient Mix+GlutaMAX-1 (Invitrogen Life Technologies, Cat. # 31765-027). This medium is further supplemented with heat-inactivated 10% fetal calf serum (FCS, JRH Biosciences, Kansas Cat. # 12107-100M), 1% NEAA (MEM Non essential Amino Acid solution (Sigma-Aldrich Cat. # M1745), and 1% Penicillin (10.000 U/ml)/Streptomycin (10.000 µg/ml) (Invitrogen Life Technologies, Cat. # 15140-122). To stimulate neuronal differentiation and growth of neuronal processes, SH-SY5Y cells were cultured in medium supplemented with 10 µM retinoic acid (RA, Sigma-Aldrich Cat. # R2625-050MG)) for several days. Differentiated SH-SY5Y cells were grown in tissue culture flasks and were removed by careful trypsination and were plated on glass coverslips coated with a striped pattern of RGM A protein or fragment of it and Collagen I.

(viii) Preparation of striped glass coverslips

The modified version of the stripe assay on glass coverslips was performed in a slightly different way as described previously (Knoell et al. Nature Protocols 2: 1216-1224, 2007) and is summarized below.

Sterile silicon matrices for production of stripes consisting of purified proteins were pressed on the surface of a petri dish with the rough face of the matrix pointing upwards. Ethanol washed, clean coverslips were laid down onto the matrix and the corners of the matrix are marked with an ink ball point pen at the backside of the coverslip. The matrix carrying the coverslip was carefully turned upside down with the coverslip facing the bottom of the petri dish. Fc-conjugated full length inhibitory RGM A or fc-fragments or recombinant human RGM A (R&D Systems Cat. # 2459 RM) of it were mixed with 10 µl of an FITC-labeled anti-mouse antibody (Fab-specific goat anti-mouse IgG, Sigma-Aldrich Cat. # F-4018) to visualize the RGM A stripes. Using a Hamilton syringe, 50 µl of the RGM A-FITC antibody solution is carefully injected through the inlet channel. Excess fluid left the matrix through the outlet channel and is removed with a Kleenex cloth. After incubation of the matrix-coverslip at 37° C. for 2 hours, the first coating solution (containing RGM A) was washed away with 100 µl of PBS. In the next step, the coverslip with the RGM A stripes was transferred to a 24 well plate, coated with 500 µl Collagen I (rat tail Collagen I, Becton Dickinson Biosciences Cat. # 354236) to fill the empty spaces between the RGM A stripes and was incubated at 37° C. for 2 hours. In the end a pattern of alternating stripes of RGM A and Collagen I was produced on the coverslip. After incubation, non-bound Collagen I was washed away by three separate wash steps with PBS and differentiated SH-SY5Y cells were plated onto the coverslips. Incubation of the SH-SY5Y cells on the patterned substrate was continued at 37° C. for 20-24 hours in the presence or absence of monoclonal antibodies directed against human RGM A.

For immunofluorescence analysis cells were fixed in 4% paraformaldehyde for 2 h at room temperature or overnight at 4° C. and permeabilized by incubation with PBS containing 0.1% Triton X-100 for 10-20 min at room temperature. After blocking with 3% BSA for 60 minutes, cells were incubated with the primary antibody (monoclonal anti-β-tubulin isotype 3 clone SDL 3D10, Sigma-Aldrich Cat. # T8660) for 2 hours at room temperature and after several wash steps with the secondary antibody (Cy-3 donkey anti-mouse Jackson-Immuno Research Lot:62597), diluted in PBS with 0.1% BSA for 1 h. Nuclei were counterstained using bisbenzimide H33258 (Riedel-De-Haen, Cat. # A-0207). Cells were finally embedded in Fluoromount G (Southern Biotechnology Associates Inc.: Cat. # 010001). Cells were analysed using an Axioplan2 fluorescence microscope (Zeiss).

(ix) Construction and expression of recombinant anti RGMA antibodies

The DNA encoding the cDNA fragments of the heavy chain variable region of rat anti-human RGMA monoclonal antibodies 5F9 and 8D1 was cloned into a pHybE expression vector containing the human IgG1 constant region, which contains 2 hinge-region amino acid mutations, by homologous recombination in bacteria. These mutations are a leucine to alanine change at positions 234 and 235 (EU numbering, Lund et al., 1991, J. Immunol., 147:2657). The light chain variable region of the 5F9 and 8D1 monoclonal antibodies were cloned into pHybE vector containing a human kappa constant region. Exemplary pHyb-E vectors include the pHybE-hCk, and pHybE-hCg1, z, non-a (see U.S. Patent Application Ser. No. 61/021,282). Full-length antibodies were transiently expressed in 293E cells by co-transfection of chimeric heavy and light chain cDNAs ligated into the pHybE expression plasmid. Cell supernatants containing recombinant antibody were purified by Protein A Sepharose chromatography and bound antibody was eluted by addition of acid buffer. Antibodies were neutralized and dialyzed into PBS. The purified anti-human RGMA monoclonal antibodies were then tested for their ability to bind RGMA by ELISA as described in Example 1 and competition ELISA as described in Example 7.

Example 1

Generation of Anti Human RGMA Monoclonal Antibodies

Anti human RGMA rat monoclonal antibodies were obtained as follows:

Example 1A

Immunization of Rats with Human RGMA Antigen

Twenty-five micrograms of recombinant purified human RGMA (R&D Systems Cat#2459-RM lot MRHO2511A) mixed with complete Freund's adjuvant (Sigma,) was injected subcutaneously into four 6-8 week-old Harlan Sprague Dawley rats on day 1. On days 21, 42, and 63, twenty-five micrograms of recombinant purified human RGMA mixed with Incomplete Freunds adjuvant (Sigma) was injected subcutaneously into the same 4 Harlan Sprague Dawley rats. On day 144, or day 165 rats were injected intravenously with 10 μg recombinant purified human RGMA Example 1B Generation of Hybridoma Splenocytes obtained from the immunized rats described in Example 1.2.A were fused with SP2/O-cells at a ratio of 2:1 according to the established method described in Kohler, G. and Milstein 1975, Nature, 256:495 to generate hybridomas. Fusion products were plated in selection media containing azaserine and hypoxanthine in 96-well plates at a density of $1.5 \times 10^5$ spleen cells per well. Seven to ten days post fusion, macroscopic hybridoma colonies were observed. Supernatant from each well containing hybridoma colonies was tested by direct ELISA (see Example 2) for the presence of antibody to human RGMA. ELISA positive cell lines were tested in FACS against stable transfected HEK293 cells expressing human and/or rat RGMA. These rat hybridoma cell lines were subsequently tested in Direct ELISA for crossreactivity with rat RGMA, and ELISA binding to HuRGMA 47-168 fusion protein.

TABLE 7

Binding of anti RGMA Rat Monoclonal Antibodies

| Name | Direct ELISA rHuRGMA | FACS HEK293-rhRGMA | Direct ELISA rRatRGMA | Direct ELISA hRGMA 47-168/HuIgGFc |
|---|---|---|---|---|
| ML68-8D1 | Yes | Yes | No | Yes |
| ML69-5F9 | Yes | Yes | Yes | Yes |

Example 2

Direct ELISA Binding of mABs 5F9 and 8D1

As shown in FIG. 1A, MABs 5F9 and 8D1 bind to hRGM A with similar titers, as described in above section (i). MAB 5F9 was also shown to bind to ratRGM A in ELISA, while 8D1 is not capable of binding to ratRGM A (data not shown). FIG. 1B shows that MABs 5F9 and 8D1 bind to HEK293 cells overexpressing hRGM A in FACS. FIG. 1C shows that 5F9 but not 8D1 is capable of binding BAF3 cells overexpressing ratRGM A in FACS. FACS was carried out as described in section (ii).

Figure 2:
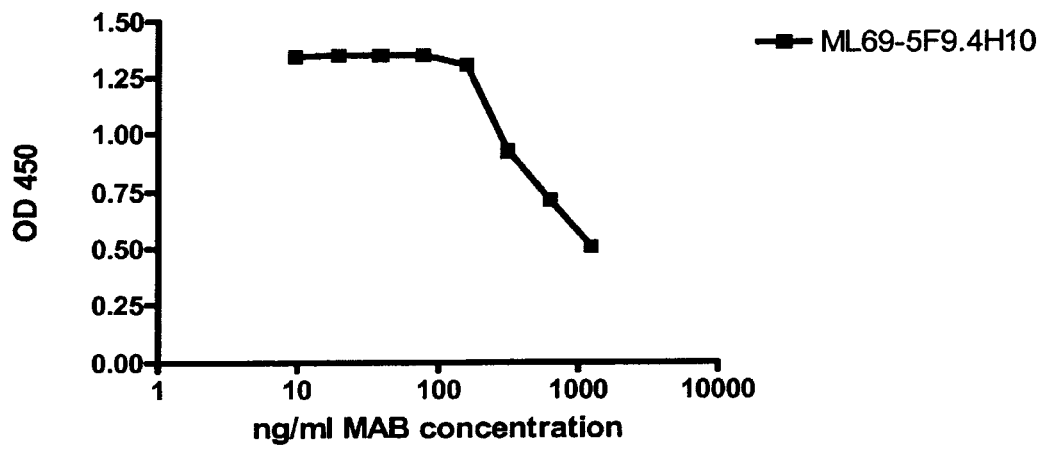
FIG. 2 shows the full length RGM A binding to Neogenin. MAB 5F9 inhibits binding of full length, fc-coupled hRGM A to Neogenin.

Solid phase ELISA assays were used to evaluate MAB 5F9 binding in competitive hRGM A-neogenin binging assays. ELISA plates were prepared and used as described in section (iii) of the present application. hRGM A was added at a concentration of 0.5 μg/ml with 5F9 antibodies for 1 h at 37° C. MAB 5F9 was used at the following concentrations: 1.25 μg/ml; 0.63 μg/ml; 0.32 μg/ml; 0.16 μg/ml; 0.08 μg/ml; 0.04 μg/ml; 0.02 μg/ml; 0.01 μg/ml. Binding of hRGM A was visualized using a Biotin-labeled anti-fc antibody and a Streptavidin-Peroxidase complex. Plates were analysed (OD determination) at a wave length of 450 nm using an Anthos photometer. As shown in FIG. 2, the three highest antibody concentrations, dose-dependently inhibited binding of full length human RGM A to Neogenin.

Figure 3:
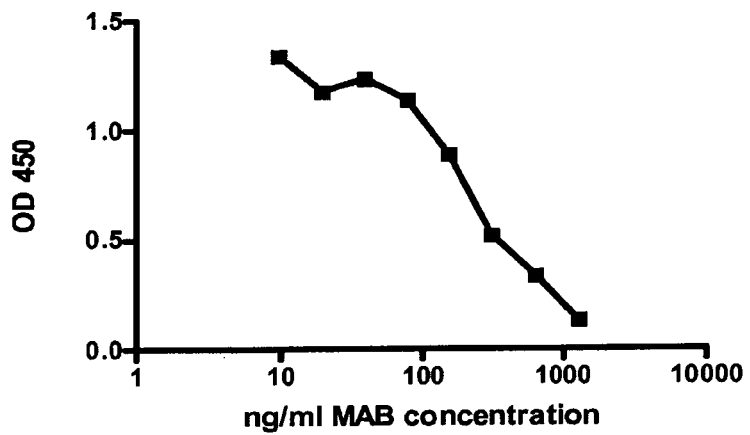
FIG. 3 depicts the full length RGM A binding to BMP-4. MAB 5F9 inhibits binding of fc-coupled full length hRGM A fragment (47-422) to BMP-4.

Solid phase ELISA assays were used also for evaluating MAB 5F9 in competitive hRGM A-BMP-4 binding assays. ELISA plates were prepared and used as described in section (iv) of the present application. hRGM A was added at a concentration of 0.5 μg/ml with 5F9 antibodies for 1 h at 37° C. MAB 5F9 was used at the following concentrations: 1.25 μg/ml; 0.63 μg/ml; 0.32 μg/ml; 0.16 μg/ml; 0.08 μg/ml; 0.04 μg/ml; 0.02 μg/ml; 0.01 μg/ml. Binding of hRGM A was visualized using a Biotin-labeled anti-fc antibody and a Streptavidin-Peroxidase complex. Plates were analysed (OD determination) at a wave length of 450 nm using an Anthos photometer. As shown in FIG. 3, the four highest antibody concentrations, dose-dependently inhibited binding of full length human RGM A to BMP-4.

Figure 4:
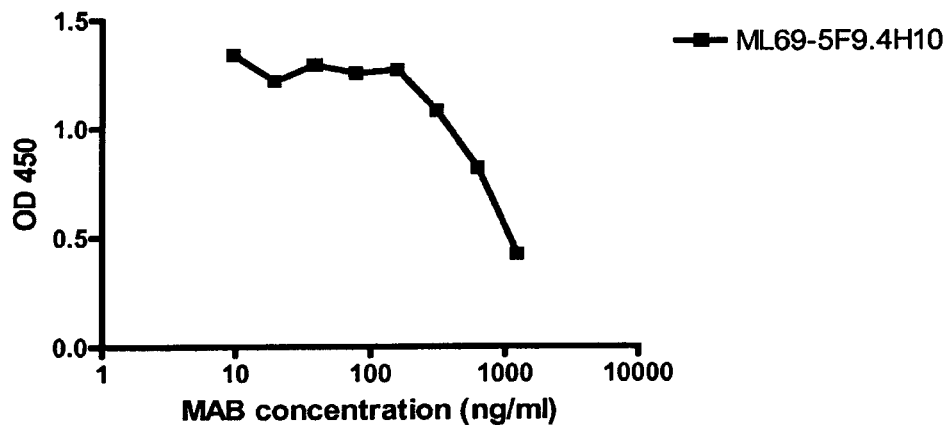
FIG. 4 depicts RGM A fragment 0 binding to BMP-4. MAB 5F9 inhibits binding of fc-coupled hRGM A fragment 0 (47-168) to BMP-4.

Solid phase ELISA assays were also used for evaluating MAB 5F9 binding inhibition of fragment 0 (47-168) hRGM A to BMP-4. ELISA plates were coated for 1 h at 37° C. with a concentration of 2.5 µg/ml of the human recombinant BMP-4 protein. hRGM A light chain (fragment 0, 47-168) was added at a concentration of 0.5 µg/ml with 5F9 antibodies for 1 h at 37° C. MAB 5F9 was used at the following concentrations: 1.25 µg/ml; 0.63 µg/ml; 0.32 µg/ml; 0.16 µg/ml; 0.08 µg/ml; 0.04 µg/ml; 0.02 µg/ml; 0.01 µg/ml. Binding of hRGM A was visualized using a Biotin-labeled anti-fc antibody and a Streptavidin-Peroxidase complex. Plates were analysed (OD determination) at a wave length of 450 nm using an Anthos photometer. FIG. 4 depicts the antibody concentrations of 1.25 µg/ml, 0.63 µg/ml and 0.32 µg/ml dose-dependently inhibiting binding of the human RGM A light chain to BMP-4.

Figure 5:
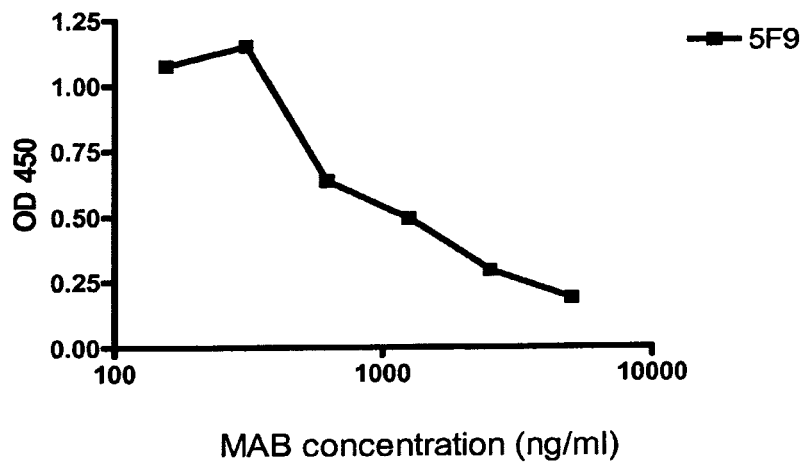
FIG. 5 shows full length RGM A binding to BMP-2. MAB 5F9 inhibits binding of fc-coupled full length hRGM A fragment (47-422) to BMP-2.

Solid phase ELISA assays were also used for evaluating MAB 5F9 binding in competitive hRGM A-BMP-2 binding assays. ELISA plates were prepared and used as described in section (v) of the present application. Full length hRGM A was added at a concentration of 0.5 µg/ml with 5F9 antibodies for 1 h at 37° C. MAB 5F9 was used at the following concentrations: 5 µg/ml; 2.5 µg/ml; 1.25 µg/ml; 0.63 µg/ml; 0.32 µg/ml; 0.16 µg/ml. Binding of hRGM A was visualized using a Biotin-labeled anti-fc antibody and a Streptavidin-Peroxidase complex. Plates were analysed (OD determination) at a wave length of 450 nm using an Anthos photometer. FIG. 5 depicts antibody concentrations 5 µg/ml, 2.5 µg/ml, 1.25 µg/ml, 0.63 µg/ml, inhibiting the binding of full length human RGM A to BMP-2.

Figure 9:
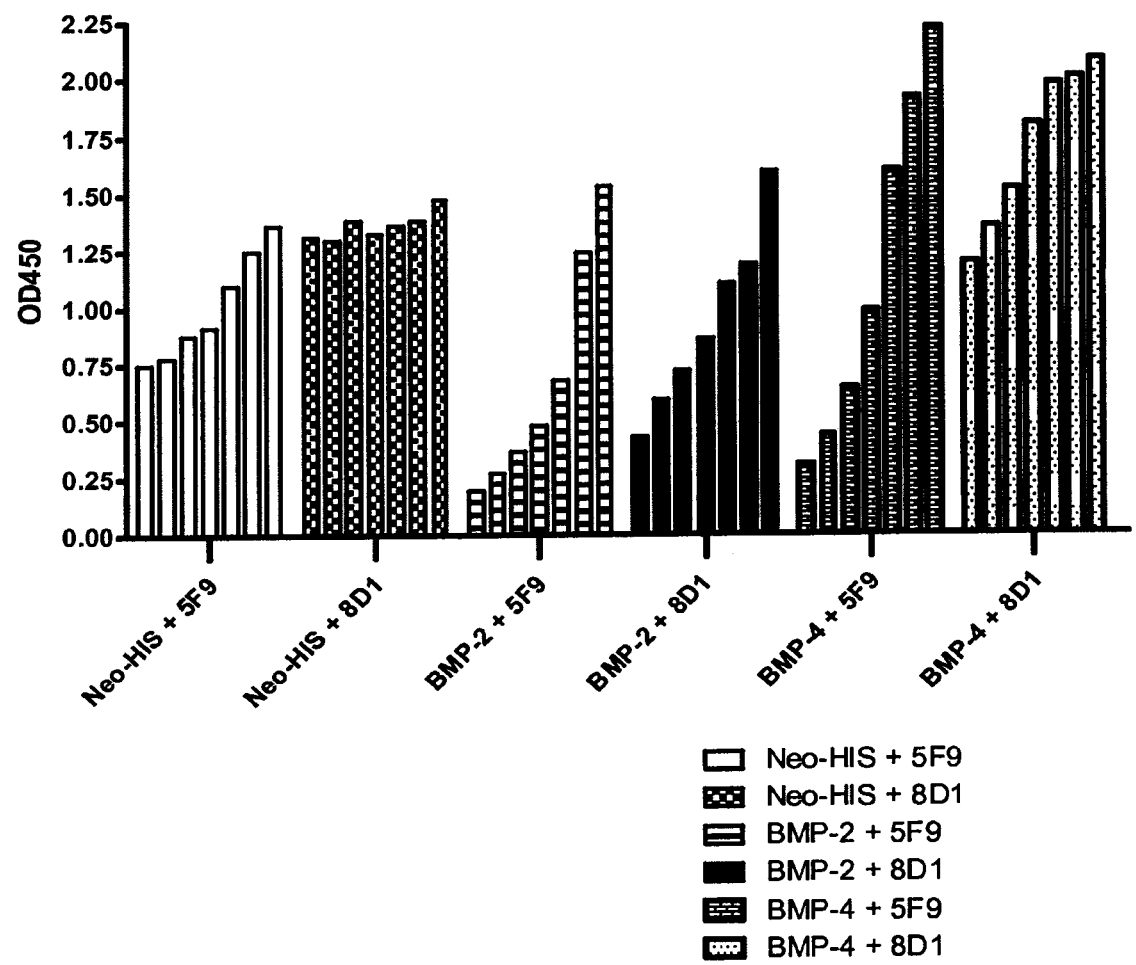
FIG. 9 summarizes the quantitative analysis of mABs 5F9 and 8D1 binding characteristics. MABs 5F9 and 8D1 are evaluated in hRGM A-neogenin, hRGM A-BMP-2 and hRGM A-BMP-4 binding assays at different concentrations.

Solid phase ELISA assays were also used to evaluate MABs 5F9 and 8D1 in hRGM A-neogenin, hRGM A-BMP-2 and hRGM A-BMP-4 binding assays. (FIG. 9) As described, ELISA plates were coated for 1 h at 37° C. with a concentration of 2.5 µg/ml of the extracellular domain of the His-tagged human Neogenin protein or with 2.5 µg/ml Bmp-2 or BMP-4. Full length fc-conjugated hRGM A was added at a concentration of 0.5 µg/ml with antibodies for 1 h at 37° C. MABs 5F9 and 8D1 were used at the following concentrations: 5 µg/ml; 2.5 µg/ml; 1.25 µg/ml; 0.63 µg/ml; 0.32 µg/ml; 0.16 µg/ml; 0.08 µg/ml. Binding of hRGM A was visualized using a Biotin-labeled anti-fc antibody and a Streptavidin-Peroxidase complex. Plates were analysed (OD determination) at a wave length of 450 nm using an Anthos photometer. As shown in FIG. 9, the rat monoclonal antibody 8D1 inhibits or reduces binding of human RGM A to BMP-2 and to BMP-4 but is not able to inhibit its binding to Neogenin.

Figure 6:
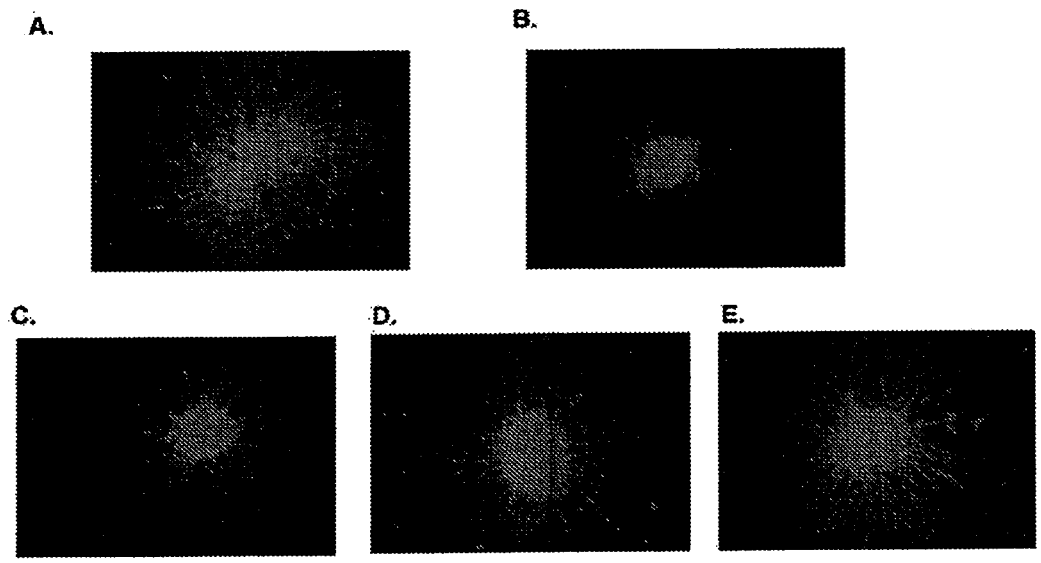
FIG. 6 is a combination of microphotographs showing mAb5F9 neutralization of RGM A fragment in NTera cell neurite outgrowth assay. MAB 5F9 neutralizes the outgrowth inhibitory activity of an fc-conjugated, potent hRGM A inhibitor fragment in neurite growth assays with human Ntera aggregates. A. Control culture, growth of Ntera neurons on laminin, B. on a laminin-hRGM A fragment (47-168) substrate, C.-E. on a laminin-hRGM A fragment (47-168) substrate in the presence of 0.1 µg/ml MAB 5F9 (C.), 1 µg/ml MAB 5F9 (D.), 10 µg/ml MAB 5F9 (E.).

Example 3 mAb 5F9 Activity in Neurite Growth Assays with Aggregates of Differentiated Human NTera Neurons Ntera cells were obtained and cultured as described in Method section (vi) of the present application. mAb 5F9 neutralized the neurite outgrowth inhibitory activity of the potent fc-conjugated light chain (amino acids 47-168) of the human RGM A protein in neurite growth assays with aggregates of differentiated human NTera neurons. As shown in FIG. 6, in the absence of an inhibitory RGM A protein or fragment and in the presence of the outgrowth-stimulating substrate laminin, neuronal NTera aggregates show an extensive and dense network of outgrowing neurites (A). Also shown in FIG. 6, the presence of the hRGM A light chain, dramatically reduces number, density and length of NTera neurites, proving the potent inhibitory activity of the hRGM A fragment. The few neurites leaving the aggregate are short and tightly bundled (B). Parts C-E of FIG. 6 show increasing concentrations of the MAB 5F9, added to the cultures does-dependently neutralised or derepressed the neurite-growth inhibitory activity of the hRGM A light chain fragment. With increasing MAB concentrations, outgrowth of NTera neuronal aggregates is completely restored, despite the presence of the RGM A inhibitor (C, 0.1 µg/ml MAB 5F9; D: 1 µg/ml MAB 5F9; E: 10 µg/ml MAB 5F9).

Figure 7:
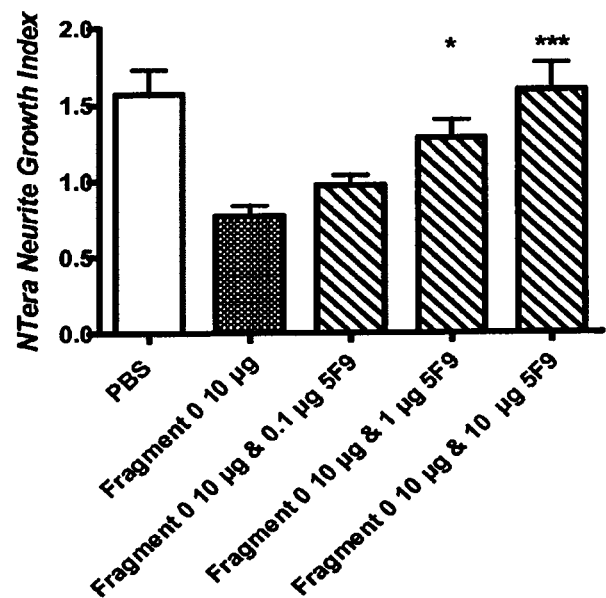
FIG. 7 shows the quantitative analysis of NTera 2 assay results. MAB 5F9 neutralizes dose-dependently the outgrowth inhibitory activity of an fc-conjugated, potent hRGM A inhibitor fragment (fragment 0, 47-168) in neurite growth assays with human Ntera aggregates.

Quantitative analysis of the neutralising activity of MAB 5F9 in neurite growth assays with human NTera aggregates was performed to test the potent fc-conjugated light chain inhibitory fragment (amino acids 47-168) of the human RGM A protein. Outgrowth of the cultures was automatically analysed by having aggregates stained with bisbenzimide and subsequently photographed. The staining only marked the aggregate not the outgrowing neurites. These were however stained with an antibody to β3-tubulin and a fluorophor-labeled secondary antibody. Neurite outgrowth was automatically determined by calculating the neurite outgrowth index, an index determined by subtracting the area of the cell bodies from the β3-tubulin stained area of the aggregate and its processes. This factor was then divided by the area of the cell bodies as described in Lingor et al. J. Neurochem. 103: 181-189, 2007. FIG. 7, shows that MAB 5F9 dose-dependently (0.1-10.0 µg) neutralized the outgrowth inhibitory activity of an fc-conjugated, potent hRGM A inhibitor fragment (fragment 0, 47-168; 10 µg) in neurite growth assays with human Ntera aggregates.

Example 4 mAb 5F9 Activity in hRGM A/Collagen I Stripes

Figure 8:
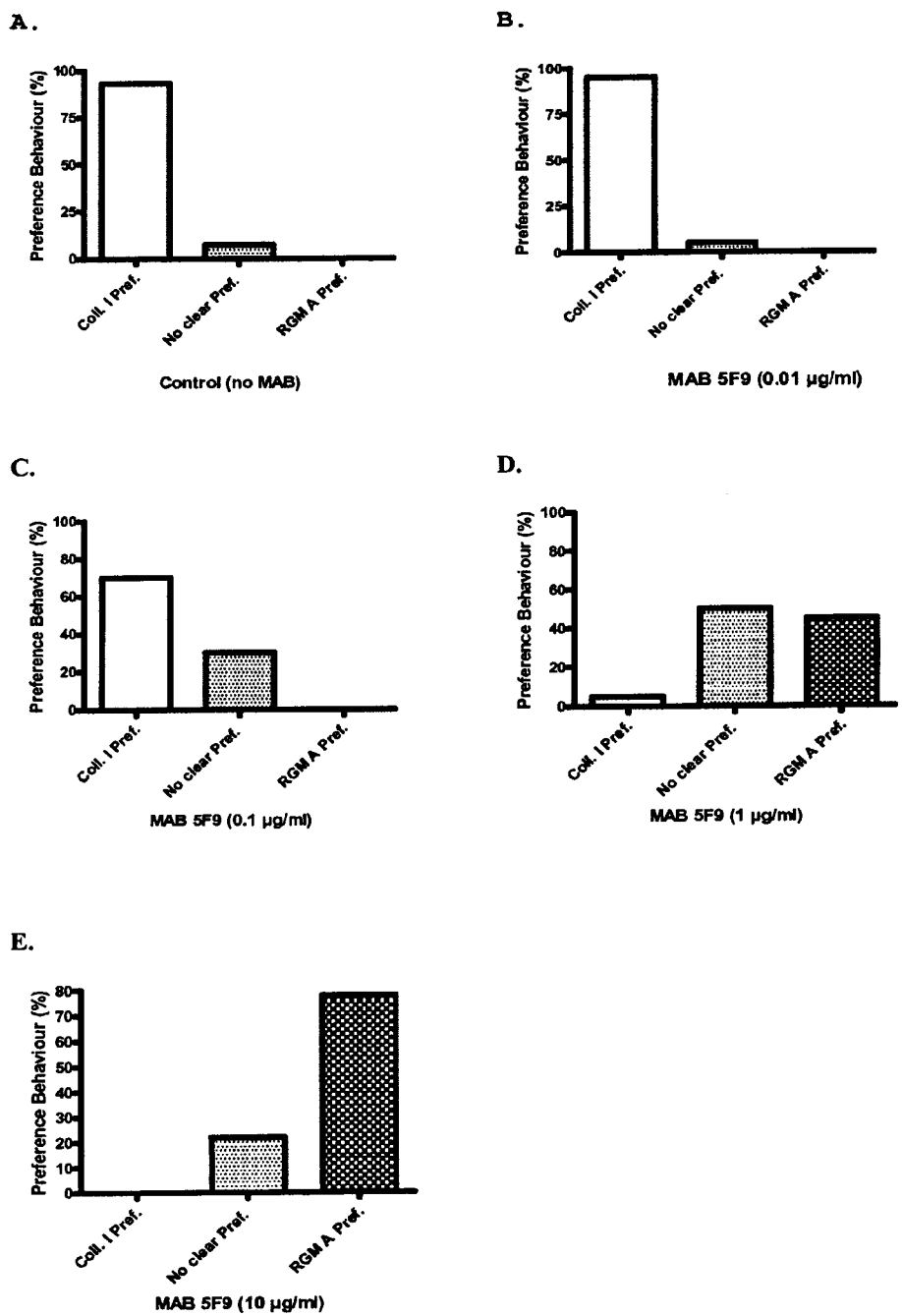
FIG. 8 shows the quantitative analysis of SH-SY5Y stripe assay. MAB 5F9 neutralizes repulsion, induced by stripes consisting of full length human RGM A of human SH-SY5Y neuronal cells in stripe membrane carpets. In the absence of MAB 5F9 (A) or in the presence of low MAB concentrations SH-SY5Y neurons prefer to avoid the RGM A stripes. This behaviour is reversed by increasing concentrations of the MAB 5F9. (B to D) At the highest MAB concentration (10 µg/ml) (E), SH-SY5Y neurons show a strong preference for the RGM A stripes in comparison with the Collagen I stripes.

SH-SY5Y cells were cultured and used as described in section (vii) of the present application. Striped glass coverslips with RGM A and Collagen I were prepared as described in section (viii) of the present application. A carpet with alternating stripes of hRGM A/Collagen I and Collagen I was produced for the experiments according to a protocol described in the literature (Knoell et al. Nature Protocols 2: 1216-1224, 2007). In the absence of the 5F9 MAB (A), neuronal SH-SY5Y cells show a clear preference for the Collagen I stripe with more than 90% of the cells preferring Collagen I stripes over hRGM A stripes. With increasing concentrations of MAB 5F9 neuronal SH-SY5Y cells prefer hRGM A stripes over Collagen I stripes (B-E). At the highest MAB concentration used (E)), SH-SY5Y neurons show a strong preference for hRGM A stripes in comparison with the Collagen I stripes (see FIG. 8). This can be interpreted as a unique characteristic of the 5F9 MAB since it transformed the inhibitory nature of RGM A in an attractive activity. In the presence of increasing concentrations of 5F9, neuronal cells prefer to migrate and grow on an RGM A substrate, and not on a permissive substrate like Collagen I. Such a unique feature has never been described before for a monoclonal antibody.

Example 5

Construction of CDR-Grafted Antibodies

By applying standard methods well known in the art, the CDR sequences of VH and VL chains of monoclonal antibody 5F9 (see Table 5 above) are grafted into different human heavy and light chain acceptor sequences. Based on sequence VH and VL alignments with the VH and VL sequences of monoclonal antibody 5F9 of the present invention the following known human sequences are selected:

a) VH3-48, VH3-33 and VH3-23 as well as the joining sequences hJH3, hJH4 and hJH6 for constructing heavy chain acceptor sequences (according to Table 3 above);
b) A17 and A18 as well as hJK2 for constructing light chain acceptor sequences (according to Table 4 above).

By grafting the corresponding VH and VL CDRs of 5F9 into said acceptor sequences the following CDR grafted, humanized, modified VH and VL sequences were prepared (see also Table 6, above): VH 5F9.1-GL, VH 5F9.2-GL, VH 5F9.3-GL, VH 5F9.4-GL, VH 5F9.5-GL, VH 5F9.6-GL, VH 5F9.7-GL, and VH 5F9.8-GL; VL 5F9.1-GL, VL 5F9.2-GL, and VL 5F9.3-GL.

Example 6

Construction of Framework Back Mutations in CDR-Grafted Antibodies

To generate humanized antibody framework back mutations, mutations are introduced into the CDR-grafted antibody sequences as prepared according to Example 5, by de novo synthesis of the variable domain and/or using mutagenic primers and PCR, and methods well known in the art. Different combinations of back mutations and other mutations are constructed for each of the CDR-grafts as follows.

For heavy chains VH 5F9.1-GL, VH 5F9.2-GL, and VH 5F9.3-GL one or more of the following Vernier and VH/VL interfacing residues are back mutated as follows: V37→I, V48→I, S491→G, and/or R981→K For heavy chains VH 5F9.4-GL, VH 5F9.5-GL, and VH 5F9.6-GL one or more of the following Vernier and VH/VL interfacing residues are back mutated as follows: V37→I, V48→I, A491→G, R981→K.

For heavy chains VH 5F9.7-GL, VH 5F9.8-GL, and VH 5F9.9-GL one or more of the following Vernier and VH/VL interfacing residues are back mutated as follows: V37→I, V48→I, S491→G.

Additional mutations include the following:
for heavy chains VH 5F9.1-GL, VH 5F9.2-GL, and VH 5F9.3-GL: D88→A,
for heavy chains VH 5F9.4-GL, VH 5F9.5-GL, and VH 5F9.6-GL: Q1→E and
for heavy chains VH 5F9.7-GL, VH 5F9.8-GL, and VH 5F9.9-GL: L5→V.

For light chain VL 5F9.1-GL one or more of the following Vernier and VH/VL interfacing residues are back mutated as follows: I2→V, M4→L, Y4→F.

For light chain VL 5F9.2-GL one or more of the following Vernier and VH/VL interfacing residues are back mutated as follows: M4→L, R51→L.

For light chain VL 5F9.3-GL one or more of the following Vernier and VH/VL interfacing residues are back mutated as follows: M4→L, Y41→F.

Example 7

Construction and Expression of Recombinant Humanized Anti RGMA Antibodies pHybE expression vectors harboring heavy and light chains containing framework back mutations were co-transfected into 293-6E cells to transiently produce full-length humanized antibodies as described in section ix above. Mutations were introduced into the CDR-grafted antibody sequences as prepared according to Example 5, by de novo synthesis of the variable domain and/or using mutagenic primers and PCR, and methods well known in the art. The amino acid sequences of the VH and VL regions of the humanized antibodies are disclosed in Table 8.

Specifically, for the heavy chains:
VH 5F9.1, VH 5F9.5, and VH 5F9.9 contain VH 5F9.4-GL with a Q1→E mutation.
VH 5F9.2, VH 5F9.6, VH 5F9.10, VH 5F9.19, VH 5F9.20, VH 5F9.21, and VH 5F9.22 contain VH 5F9.4-GL with a Q1→E mutation and the following Vernier and VH/VL interfacing residue back mutations: V37→I, V48→I, A49→G, R98→K.
VH 5F9.3, VH 5F9.7, and VH 5F9.11 contain VH 5F9.7-GL with a L5→V mutation. VH 5F9.4, VH 5F9.8, VH 5F9.12, VH 5F9.23, VH 5F9.24, VH 5F9.25, and VH 5F9.26 contain VH 5F9.7-GL with a L5→V mutation and the following Vernier and VH/VL interfacing residue back mutations: V37→I, V48→I, S49→G.

For the light chains:
VL 5F9.1, VL 5F9.2, VL 5F9.3, and VL 5F9.4 are identical to VL 5F9.1-GL.
VL 5F9.5, VL 5F9.6, VL 5F9.7, and VL 5F9.8 are identical to VL 5F9.2-GL.
VL 5F9.9, VL 5F9.10, VL 5F9.11, and VL 5F9.12 are identical to VL 5F9.3-GL.
VL 5F9.19 and VL 5F9.23 contain VL 5F9.2-GL with the following Vernier and VH/VL interfacing residue back mutations: M4→L, R5→L. VL 5F9.20 and VL 5F9.24 contain VL 5F9.2-GL with the following Vernier and VH/VL interfacing residue back mutation: M4→L.
VL 5F9.21 and VL 5F9.25 contain VL 5F9.3-GL with the following Vernier and VH/VL interfacing residue back mutations: M4→L, Y41→F. VL 5F9.22 and VL 5F9.26 contain VL 5F9.3-GL with the following Vernier and VH/VL interfacing residue back mutation: M4→L.

TABLE 8

Expression of humanized antibodies

| SEQ ID No. | Protein region | Sequence 12345678901234567890123456789 0 |
|---|---|---|
| 47 | VH h5F9.1 | EVQLVESGGGVVQPGRSLRLSCAASGFTFS NYGMNWVRQAPGKGLEWVAMIYYDSSEKHY ADSVKGRFTISRDNSKNTLYLQMNSLRAED TAVYYCARGTTPDYWGQGTMVTVSS |
| 44 | VL h5F9.1 | DIVMTQTPLSLSVTPGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 48 | VH h5F9.2 | EVQLVESGGGVVQPGRSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 44 | VL h5F9.2 | DIVMTQTPLSLSVTPGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 49 | VH h5F9.3 | EVQLVESGGGLVQPGGSLRLSCAASGFTFS NYGMNWVRQAPGKGLEWVSMIYYDSSEKHY ADSVKGRFTISRDNSKNTLYLQMNSLRAED TAVYYCAKGTTPDYWGQGTMVTVSS |
| 44 | VL h5F9.3 | DIVMTQTPLSLSVTPGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 50 | VH h5F9.4 | EVQLVESGGGLVQPGGSLRLSCAASGFTFS NYGMNWIRQAPGKGLEWIG**MIYYDSSEKHY |

TABLE 8-continued

Expression of humanized antibodies

| SEQ ID No. | Protein region | Sequence 12345678901234567890123456789 |
|---|---|---|
|  |  | ADSVKGRFTISRDNSKNTLYLQMNSLRAED TAVYYCAKGTTPDYWGQGTMVTVSS |
| 44 | VL h5F9.4 | DIVMTQTPLSLSVTPGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 47 | VH h5F9.5 | EVQLVESGGGVVQPGRSLRLSCAASGFTFS NYGMNWVRQAPGKGLEWVAMIYYDSSEKHY ADSVKGRFTISRDNSKNTLYLQMNSLRAED TAVYYCARGTTPDYWGQGTMVTVSS |
| 45 | VL h5F9.5 | DVVMTQSPLSLPVTLGQPASISCRSSQSLE YSDGYTFLEWFQQRPGQSPRRLIYEVSNRF SGVPDRFSGSGSGTDFTLKISRVEAEDVGV YYCFQATHDPLTFGQGTKLEIKR |
| 48 | VH h5F9.6 | EVQLVESGGGVVQPGRSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 45 | VL h5F9.6 | DVVMTQSPLSLPVTLGQPASISCRSSQSLE YSDGYTFLEWFQQRPGQSPRRLIYEVSNRF SGVPDRFSGSGSGTDFTLKISRVEAEDVGV YYCFQATHDPLTFGQGTKLEIKR |
| 49 | VH h5F9.7 | EVQLVESGGGLVQPGGSLRLSCAASGFTFS NYGMNWVRQAPGKGLEWVSMIYYDSSEKHY ADSVKGRFTISRDNSKNTLYLQMNSLRAED TAVYYCAKGTTPDYWGQGTMVTVSS |
| 45 | VL h5F9.7 | DVVMTQSPLSLPVTLGQPASISCRSSQSLE YSDGYTFLEWFQQRPGQSPRRLIYEVSNRF SGVPDRFSGSGSGTDFTLKISRVEAEDVGV YYCFQATHDPLTFGQGTKLEIKR |
| 50 | VH h5F9.8 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 45 | VL h5F9.8 | DVVMTQSPLSLPVTLGQPASISCRSSQSLE YSDGYTFLEWFQQRPGQSPRRLIYEVSNRF SGVPDRFSGSGSGTDFTLKISRVEAEDVGV YYCFQATHDPLTFGQGTKLEIKR |
| 47 | VH h5F9.9 | EVQLVESGGGVVQPGRSLRLSCAASGFTFS NYGMNWVRQAPGKGLEWVAMIYYDSSEKHY ADSVKGRFTISRDNSKNTLYLQMNSLRAED TAVYYCARGTTPDYWGQGTMVTVSS |
| 46 | VL h5F9.9 | DVVMTQSPLSLPVTLGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 48 | VH h5F9.10 | EVQLVESGGGVVQPGRSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 46 | VL h5F9.10 | DVVMTQSPLSLPVTLGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 49 | VH h5F9.11 | EVQLVESGGGLVQPGGSLRLSCAASGFTFS NYGMNWVRQAPGKGLEWVSMIYYDSSEKHY ADSVKGRFTISRDNSKNTLYLQMNSLRAED TAVYYCAKGTTPDYWGQGTMVTVSS |
| 46 | VL h5F9.11 | DVVMTQSPLSLPVTLGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 50 | VH h5F9.12 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 46 | VL h5F9.12 | DVVMTQSPLSLPVTLGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 48 | VH h5F9.19 | EVQLVESGGGVVQPGRSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 51 | VL h5F9.19 | DVVLTQSPLSLPVTLGQPASISCRSSQSLE YSDGYTFLEWFQQRPGQSPRLLIYEVSNRF SGVPDRFSGSGSGTDFTLKISRVEAEDVGV YYCFQATHDPLTFGQGTKLEIKR |
| 48 | VH h5F9.20 | EVQLVESGGGVVQPGRSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 52 | VL h5F9.20 | DVVLTQSPLSLPVTLGQPASISCRSSQSLE YSDGYTFLEWFQQRPGQSPRRLIYEVSNRF SGVPDRFSGSGSGTDFTLKISRVEAEDVGV YYCFQATHDPLTFGQGTKLEIKR |
| 48 | VH h5F9.21 | EVQLVESGGGVVQPGRSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 53 | VL h5F9.21 | DVVLTQSPLSLPVTLGQPASISCRSSQSLE YSDGYTFLEWFLQKPGQSPQLLIYEVSNRF SGVPDRFSGSGSGTDFTLKISRVEAEDVGV YYCFQATHDPLTFGQGTKLEIKR |
| 48 | VH h5F9.22 | EVQLVESGGGVVQPGRSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 54 | VL h5F9.22 | DVVLTQSPLSLPVTLGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |
| 50 | VH h5F9.23 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 51 | VL h5F9.23 | DVVLTQSPLSLPVTLGQPASISCRSSQSLE YSDGYTFLEWFQQRPGQSPRLLIYEVSNRF SGVPDRFSGSGSGTDFTLKISRVEAEDVGV YYCFQATHDPLTFGQGTKLEIKR |
| 50 | VH h5F9.24 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 52 | VL h5F9.24 | DVVLTQSPLSLPVTLGQPASISCRSSQSLE YSDGYTFLEWFQQRPGQSPRRLIYEVSNRF |

TABLE 8-continued

Expression of humanized antibodies

| SEQ ID No. | Protein region | Sequence 123456789012345678901234567890 |
|---|---|---|
| | | SGVPDRFSGSGSGTDFTLKISRVEAEDVGV YYCFQATHDPLTFGQGTKLEIKR |
| 50 | VH h5F9.25 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 53 | VL h5F9.25 | DVVLTQSPLSLPVTLGQPASISCRSSQSLE YSDGYTFLEWFLQKPGQSPQLLIYEVSNRF SGVPDRFSGSGSGTDFTLKISRVEAEDVGV YYCFQATHDPLTFGQGTKLEIKR |
| 50 | VH h5F9.26 | EVQLVESGGGLVQPGGSLRLSCAASGFTFS NYGMNWIRQAPGKGLEWIGMIYYDSSEKHY ADSVKGRFTISRDNSKNTLYLQMNSLRAED TAVYYCAKGTTPDYWGQGTMVTVSS |
| 54 | VL h5F9.26 | DVVLTQSPLSLPVTLGQPASISCRSSQSLE YSDGYTFLEWYLQKPGQSPQLLIYEVSNRF SGVPDRFSGSGSGTDFTLKISRVEAEDVGV YYCFQATHDPLTFGQGTKLEIKR |

Example 8

Characterization of Humanized 5F9 Antibodies Using Competition ELISA

ELISA plates (Costar 3369) were coated overnight at 4° C. with 50 µl/well of 0.25 µg/ml hRGMA in 0.2 M sodium carbonate-bicarbonate buffer, pH 9.4, washed with Wash Buffer (PBS containing 0.1% Tween 20), and blocked for 1 hr at room temperature with 200 µl/well of 2% nonfat dry milk in PBS. After washing with Wash Buffer, a mixture of a biotinylated chimeric 5F9 (0.1 µg/ml final concentration) and unlabelled competitor test antibody starting at 50 µg/ml final concentration and serially diluted 5-fold) in 50 µl/well of ELISA buffer was added in duplicate. After incubating the plates for 1 hr at room temperature, and washing with Wash Buffer, bound antibodies were detected using 100 µl/well of 1:10,000 dilution of HRP-conjugated streptavidin (Fitzgerald) in ELISA buffer. After incubating for 1 hr at room temperature, and washing with Wash Buffer, color development was performed by adding 100 µl/well of TMB Buffer (Zymed). After incubating for 15 min at room temperature, color development was stopped by adding 50 µl/well of 1N hydrochloric acid. Absorbance was read at 490 nm.

Table 9 shows the $IC_{50}$ values of humanized 5F9 antibodies obtained using the computer software GraphPad Prism (GraphPad Software Inc., San Diego, Calif.).

TABLE 9

IC50 values of humanized 5F9 antibodies in competitive ELISA

| Antibody | IC50 (µg/ml) |
|---|---|
| h5F9.1 | >10 |
| h5F9.2 | >10 |
| h5F9.3 | >10 |
| h5F9.4 | >10 |
| h5F9.5 | >10 |
| h5F9.6 | >10 |
| h5F9.7 | >10 |
| h5F9.8 | >10 |

TABLE 9-continued

IC50 values of humanized 5F9 antibodies in competitive ELISA

| Antibody | IC50 (µg/ml) |
|---|---|
| h5F9.9 | >10 |
| h5F9.10 | >10 |
| h5F9.11 | >10 |
| h5F9.12 | >10 |
| h5F9.19 | N/A |
| h5F9.20 | >2.0 |
| h5F9.21 | 0.60 |
| h5F9.22 | >2.0 |
| h5F9.23 | 0.55 |
| h5F9.24 | 1.32 |
| h5F9.25 | 0.66 |
| h5F9.26 | >2.0 |

Example 9

Affinity Determinations of Chimeric and Humanized Antibodies Using BIACORE Technology The BIACORE assay (Biacore, Inc, Piscataway, N.J.) determines the affinity of antibodies with kinetic measurements of on-, off-rate constants. Binding of antibodies to recombinant purified human RGMA was determined by surface plasmon resonance-based measurements with a Biacore® 3000 instrument (Biacore® AB, Uppsala, Sweden) using running HBS-EP (10 mM HEPES [pH 7.4], 150 mM NaCl, 3 mM EDTA, and 0.005% surfactant P20) at 25° C. All chemicals were obtained from Biacore® AB (Uppsala, Sweden). Approximately 5000 RU of goat anti-human IgG, (Fcγ), fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 µg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-human IgG in flow cell 1 and 3 was used as the reference surface. Purified antibodies were diluted in HEPES-buffered saline for capture across goat anti-humanIgG specific reaction surfaces. Human antibodies to be captured as a ligand (25 µg/ml) were injected over reaction matrices at a flow rate of 5 µl/min. The association and dissociation rate constants, $k_{on}$ (unit $M^{-1} s^{-1}$) and $k_{off}$ (unit $s^{-1}$) were determined under a continuous flow rate of 25 µl/min. Rate constants were derived by making kinetic binding measurements at ten different antigen concentrations ranging from 0.39-50 nM. For kinetic analysis, rate equations derived from the 1:1 Langmuir binding model were fitted simultaneously to association and dissociation phases of all eight injections (using global fit analysis) with the use of Biaevaluation 4.0.1 software. The equilibrium dissociation constant (unit M) of the reaction between humanized antibodies and recombinant purified human RGMA was then calculated from the kinetic rate constants by the following formula: $K_D = k_{off}/k_{on}$.

TABLE 9

Affinity of chimeric and humanized anti-RGMA Monoclonal Antibodies

| Name | $k_{on}$ (1/M · s) | $k_{off}$ (1/s) | $K_D$ (nM) |
|---|---|---|---|
| chimeric 5F9 | $7.65 \times 10^5$ | $2.36 \times 10^{-3}$ | 3.09 |
| h5F9.21 | $3.55 \times 10^5$ | $2.69 \times 10^{-3}$ | 7.59 |
| h5F9.23 | $5.07 \times 10^5$ | $2.21 \times 10^{-3}$ | 4.37 |
| h5F9.25 | $5.70 \times 10^5$ | $3.29 \times 10^{-3}$ | 5.78 |

Example 10

The Humanised 5F9 Antibodies Neutralise Chemorepulsive Activity of Human RGM A in a Neuronal SH-SY5Y Chemotaxis Assay The chemotaxis assay measures chemotactic behaviour of cells in response to diffusible factors which can exert chemoattracticve or chemorepulsive activities. RGM A has been described as a protein acting in both membrane-bound (contact-dependent repulsion) and in soluble, diffusible form (chemorepulsive) and has therefore been evaluated in an hRGM A chemotaxis assay. To this aim RGM A-sensitive human neuroblastoma cells SH-SY5Y, carrying the RGM receptor Neogenin were used (Schaffar et al. J. Neurochemistry: 107: 418-431, 2008). SH-SY5Y cells were grown in Earle's Balanced Salt Solution/F12 (EBSS/F12) medium supplemented with 10% fetal bovine serum and 1% non-essential amino acids (MEM-NEAA). For induction of neurite outgrowth cells were cultured in medium supplemented with 10 µM retinoic acid (RA). 5-6 hours later, cells were trypsinized and counted for plating in 24-well Boyden Chambers (BD Falcon 351185, HTS Multiwell System). 500 µl of the cell suspension (corresponding to $1 \times 10^5$ cells) was added to the inner circle of each well. This inner circle is separated from the larger outer circle of each well by a PET membrane with 8 µm pore diameter. 600 µl of medium +/− RGM A +/− antibodies were pipetted into the outer circle and cells were cultivated in the Multiwell Boyden Chambers overnight at 37° C. After incubation medium was aspirated and replaced by the fixative (2% paraformaledhyde. Fixation was continued for 2 hours at room temperature and after several wash steps with PBS permeabilization was performed using PBS containing 0.1% Triton-X-100 (15 min, RT). Staining of cells was done by incubating them for 1 hour in the dark in a solution of Alexa Fluor 488 Phalloidin 1:100 (Invitrogen A12379) and Bisbenzimide (H332456) 1:100. After 2 wash steps with PBS, cultures were filled by PBS, sealed by parafilm and stored in the dark for the analysis with a fluorescence microscope (Zeiss Axiovert).

Figure 10:
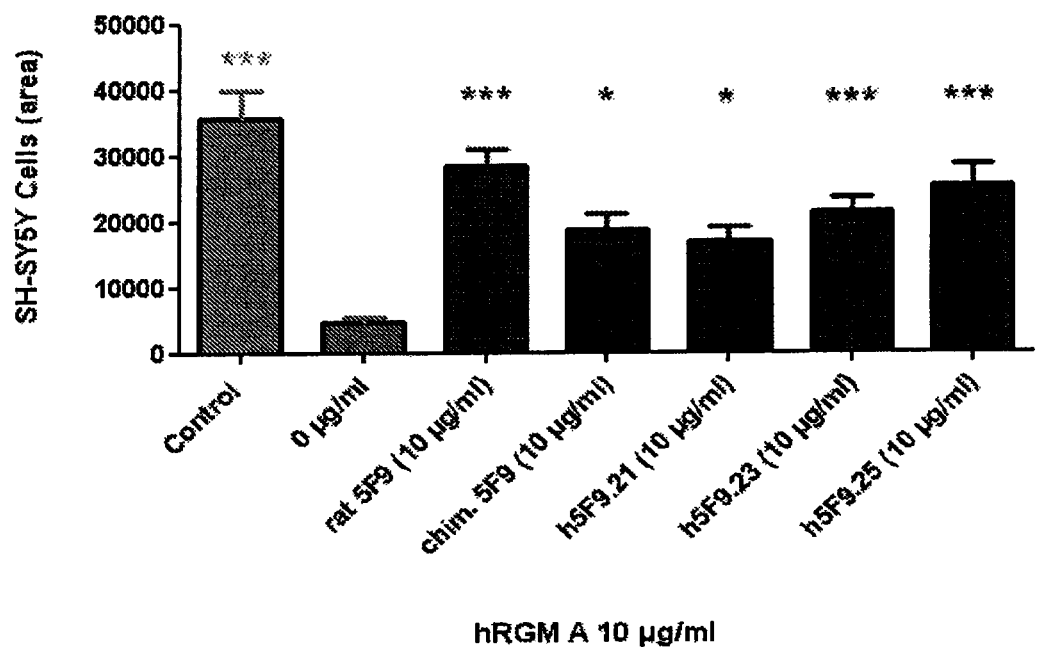
FIG. 10 shows neutralizing activity for hRGM A's chemorepulsive activity of humanized 5F9 antibodies (h5F9.21, h5F9.23, h5F9.25) in an SH-SY5Y chemotaxis assay.

In the absence of hRGM A cells migrate through the membrane pores and can be counted after fixation and staining. Only those cells are counted which attached to the bottom of the membrane, because these cells had migrated through the PET membrane. Cells on the upper side of the membrane were carefully removed before the fixation procedure. This chemotaxis assay proved that presence of hRGM A significantly reduced the number of SH-SY5Y cells migrating through the membrane by more than 80%. The rat monoclonal 5F9, the chimeric human-rat 5F9 and the humanised 5F9 but not an isotype control rat monoclonal antibody (p21) partially or completely neutralised chemorepulsive activity of hRGM A at 10 µg/ml, manifested as larger numbers of cells found at the bottom of the membrane (FIG. 10).

Example 11

5F9 Induces Regeneration of Crushed, Damaged Optic Nerve Axons in a Rat Model of Optic Nerve Injury The model of Optic Nerve Crush (or Optic Nerve Injury) provides an animal model to test various substances that stimulate regeneration of the optic nerve fibers and reduce the massive cell death of retinal ganglion cells.

The experiments were carried out in adult male Sprague Dawley and male Wistar rats obtained from Charles River (D) Laboratories (Germany). The animals are kept in single cages on a 12:12 h light/dark cycle with food and water ad libitum. The optic nerve crush is performed always only at the left eye by minimal anterior surgery. This is a minimally invasive method of optic nerve injury and was developed by us, according to human anterior visual surgical methods. Before and during the operation procedure animals are anesthetized by inhalation anesthesia using Sevoflurane (Abbott GmbH Co. & KG, Delkenheim, Germany) and are fixed on the operation table by using jawclamp and adhesive tape for the limbs. A drop in body temperature is prevented by mounting animals on a heating pad. For anterior crush surgery of the rat optic nerve, the left eye is carefully freed of ligament and connective tissue. As a first step, a microsurgical cut (2-3 mm) of the adjacent tissue in the outer corner of the eye is performed. Then the optic nerve is exposed by using a pair of forceps to move to the side the eye muscles and lacrimal gland, thus sparing it. At the next step, the meninges were longitudinally opened by using microscissors to expose the optic nerve.

This results in a higher mobility of the eye and enables lateral rotation of the eye and access to its left optic nerve. The optic nerve is injured approximately 1-3 mm behind the eye, using a pair of forceps set to provide a fixed maximum pressure for 20-30 s. Special care is taken not to damage the vascular supply to the eye.

Local Administration of Antibodies and Buffer Solution.

After crush injury of the optic nerve male Sprague Dawley rats were treated locally with 5F9 antibody (n=10 animals), the 8D1 control antibody (n=10 animals) or with a vehicle control PBS (n=10 animals). Experimenters were blinded for the different treatment groups. For local antibody application, small gelfoam pieces (length: 2.5 mm, width: 2.5 mm, height: 2.5 mm) were soaked with 20 µl of a 10 mg/ml antibody solution or with 20 µl of PBS and were placed directly adjacent to the optic nerve lesion site. After minimal invasive surgery and antibody application, animals were placed on paper towels in the clean cage mounted on the warmer to control the body temperature until they started to move. An ointment which contains antibiotic (Gentamytrex, Dr. Mann Pharma) was applied onto the eye to avoid bacterial infection and drying-out of the sclera. Carprofen (Rimadyl, 5 mg/kg, Pfizer GmbH, Karlsruhe) was applied i.p. for postoperative pain therapy directly after surgery and then twice per day for a 3 days period. The animals were observed and controlled regularly several hours directly after surgery and in the next days to make sure that all the animals survived and recovered from anesthesia and surgery. 5 weeks after surgery and antibody/vehicle application, animals were anesthesized with an overdose of Narcoren (40-60 mg/kg) and were perfused by injection of 4% paraformaledyde solution into the heart. Optic nerves were isolated and were transferred into a 4% paraformaldeyde solution for 1 h at room temperature to ensure proper fixation of the tissue. Following postfixation, rat optic nerves were stored over night in a 30% sucrose solution (4° C.). On the following day optic nerves were embedded in Tissue Tek, frozen and longitudinal sections with a thickness of 16 μm were made using a Cryostat.

For immunostainings, optic nerve sections were fixed with cold (−20° C.) Acetone (10 min), washed 3× (5 min) with Tris Buffered Saline (TBS, Fluka 93312) and were blocked and permeabilised with TBS, containing 5% Bovine Serum Albumin and 1% Triton-X-100 (30 min), at room temperature). Residual BSA and detergent was removed by 2 separate wash steps (5 min each) with TBS. Sections were incubated for 1 h at room temperature with a polyclonal rabbit anti-GAP-43 antibody (Abcam, ab 7562) diluted 1:100 in 5% BSA/TBS solution. After 3 wash steps with TBS, 0.1% Tween, sections were incubated for 1 h at room temperature with an Alexa Fluor 488-conjugated goat anti-rabbit secondary antibody (Molecular Probes A11034), diluted 1:1000 in 5% BSA/TBS, containing a 1:100 dilution of Bisbenzimid (H33258, 50 μg/ml) to visualize cell nuclei. Before embedding, stained sections were washed 3 times with TBS 0.1% Tween (5 min each step) and with distilled water. Sections were embedded in Fluoromount G, were covered by a coverslip and were stored in the dark for microscopic documentation.

Figure 11:
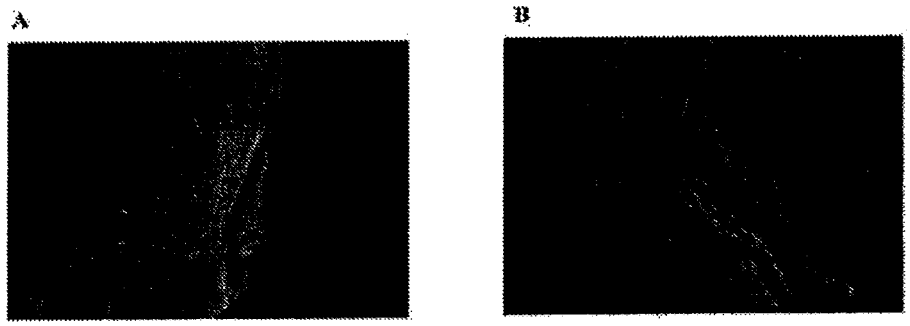
FIG. 11 shows the in vivo neuroregenerative activity of local 5F9 application in an animal model of optic nerve injury. Local application of MAB 5F9 neutralizes RGM A and stimulates regenerative growth of damaged optic nerve axons in a rat animal model of optic nerve crush. In the 5F9 treated animals (A), many GAP-43 positive fibers are extending beyond the crush site in contrast to the control MAB 8D1 (B), which does not bind to rat RGM A.
Figure 12A:
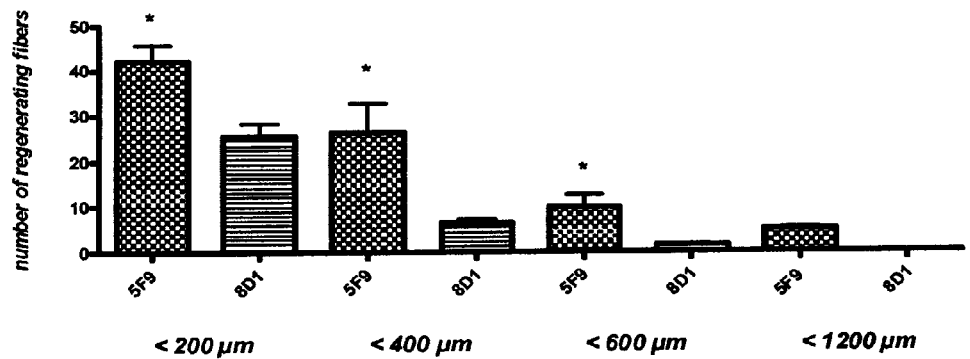
FIGS. 12 A and FIGS. 12 B show the quantitative analysis of local 5F9 application in an animal model of optic nerve injury. (A) 5F9 but not the control MAB 8D1 significantly increased the number of regenerating GAP-43 positive fibers. Significantly more fibers ($p<0.05$) were observed in animals treated with 5F9 at distances 200 µm, 400 µm and 600 µm and at 1200 µm fibers are only found in 5F9-treated animals but not in control animals (B) 5F9 significantly increased the GAP-43 positive area at the optic nerve lesion site in comparison with the control antibody 8D1 and the vehicle control PBS. The area of regenerative growth (GAP-43 positive area) was measured using the Axiovision software (Zeiss).
Figure 12B:
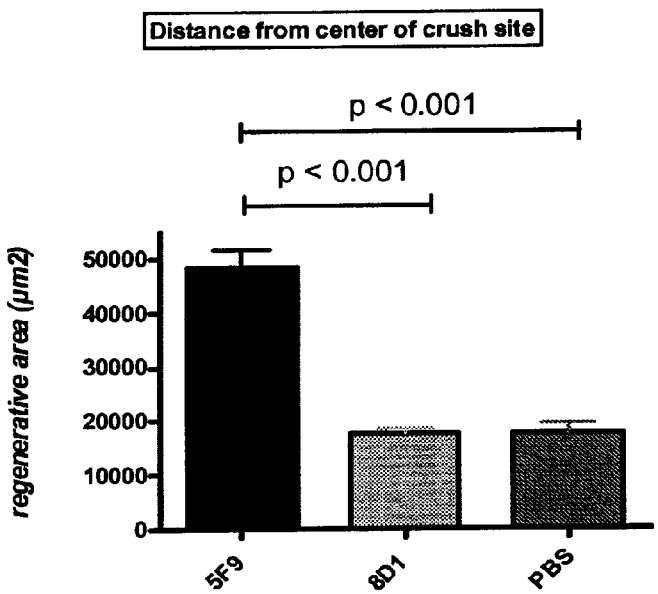

Using a Zeiss fluorescence microscope images (FIG. 11) of stained longitudinal sections were stored using the Zeiss Axiovison software. Single pictures of each nerve were mounted for analysis using Photoshop Image Analysis software (Adobe). Quantitative analysis was done in two different ways using the composite images of the optic nerves. The GAP-43-positive area at the lesion site was measured using the Axiovision software (FIG. 12B). Independent of this first quantitative analysis single regenerating fibers (GAP-43 positive) were counted in 4 different areas: 0-200 μm, 200-400 μm, 400-600 μm and 600-1200 μm beyond the crush site. Data analysis and statistical evaluation of data was done with the help of the Graphpad Prism software. (FIG. 12A)

Systemic Administration of Antibodies and Buffer Solution.

Figure 13:
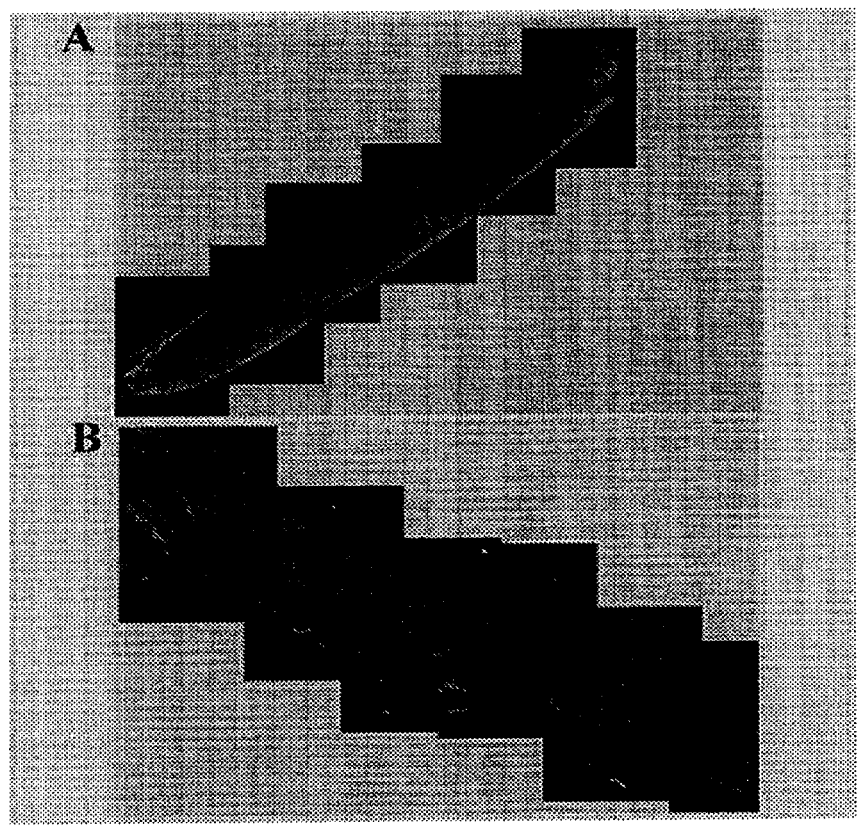
FIG. 13 shows the in vivo neuroregenerative activity of systemic 5F9 application in an animal model of optic nerve injury. Animals were treated with 5F9 at day 0 and day 21 with 2 mg/kg and 10 mg/kg, respectively. Antibody or vehicle were given intraperitoneally or intravenously. Composite images of rat optic nerves. In the 5F9 treated animals (A), many GAP-43 positive fibers are extending beyond the crush site in contrast to control animals treated with PBS (B). The crush site is located at the left margin and regenerating fibers are stained with an antibody to GAP-43. Many fibers are observed at the upper and lower rim of the optic nerve in 5F9-treated animals but not in PBS animals.

For systemic antibody delivery, male Wistar rats were treated systemically (intraperitoneally, ip) or intravenously, iv) with 5F9 antibody (n=10 animals) or with a vehicle control PBS (n=10 animals). Animals were injected two times and injections were done on day 0 shortly after inducing nerve crush and on day 21 after crush. Doses of antibody given were 2 mg/kg on day 0 and 10 mg/kg on day 21. Animals were killed five weeks after crush injury and tissue isolation, preparation of sections, stainings and quantitative analysis was done as described above. As before experimenters were blinded for the two different treatment groups. Composite images of rat optic nerves are shown in FIG. 13. In the 5F9 treated animals (A), many GAP-43 positive fibers are extending beyond the crush site in contrast to control animals treated with PBS (B). The crush site is located at the left margin and regenerating fibers are stained with an antibody to GAP-43. Many fibers are observed at the upper and lower rim of the optic nerve in 5F9-treated animals but not in PBS animals.

Figure 14A:
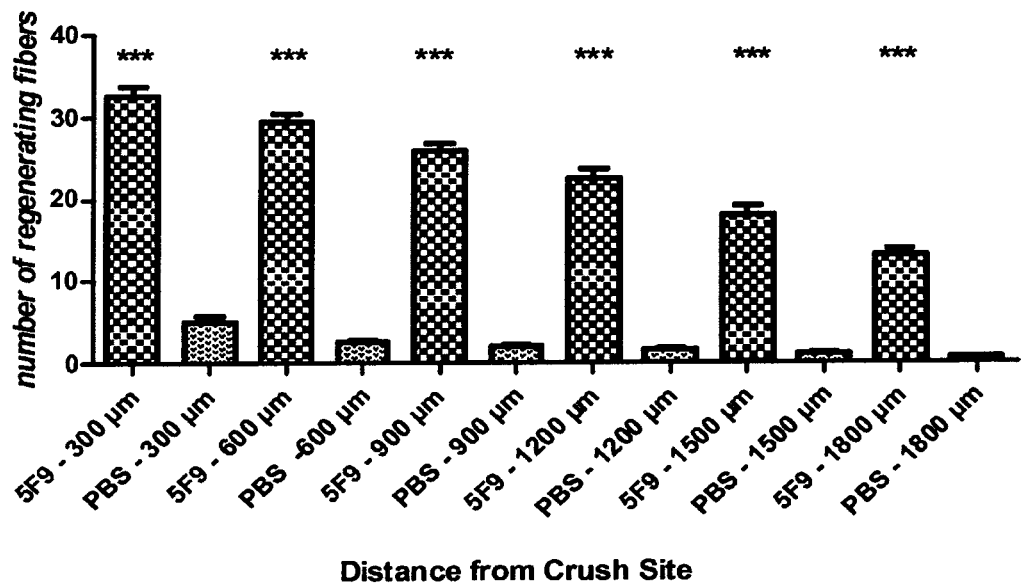
FIG. 14 A and FIG. 14 B shows the quantitative analysis of systemic 5F9 application in an animal model of optic nerve injury.

5F9 but not the vehicle control PBS significantly increased the number of regenerating GAP-43 positive fibers. Significantly more fibers (p<0.001) were found in animals treated with 5F9 at distances 300 μm to 1800 μm, than in vehicle treated animals. Animals were treated with 5F9 at day 0 and d21 with 2 mg/kg and 10 mg/kg, respectively. Antibody or vehicle were given intraperitoneally or intravenously. Data are from analysis of 9 animals per group. Per animal 3 series of cryostat sections were analysed. (FIG. 14A)

Figure 14B:
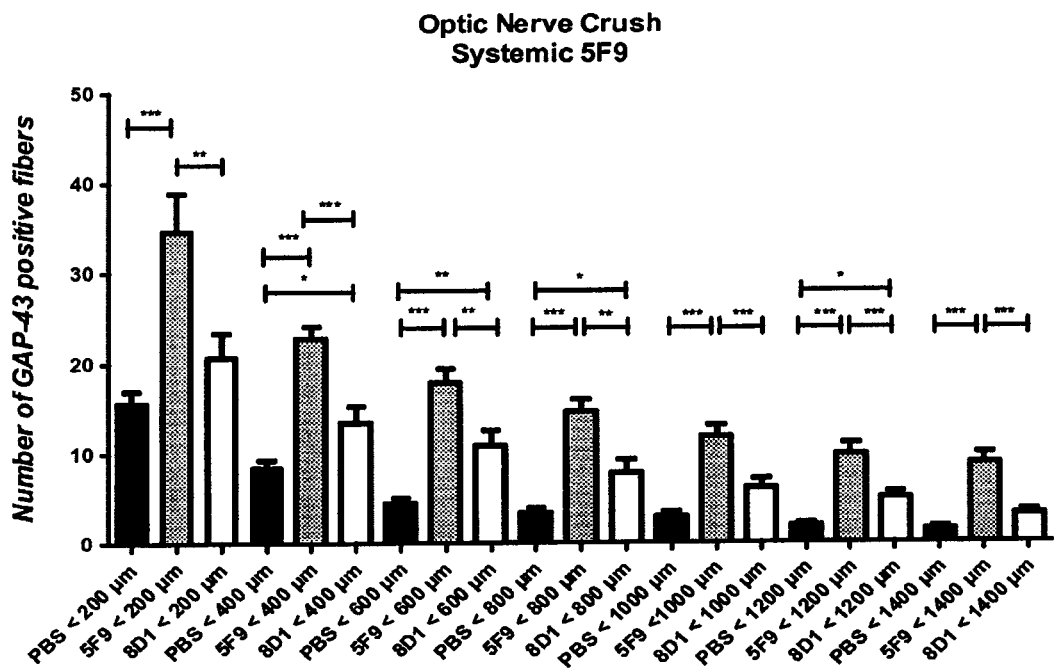

In a second experiment, male Wistar rats were treated after optic nerve injury systemically (iv) with 5F9 antibody (n=10 animals), the 8D1 control antibody (n=10 animals) or with the vehicle control PBS (n=10 animals). Rats were injected once per week with 2 mg/kg of antibody given iv and injections were started immediately after optic nerve crush. All rats received 4 injections and animals were euthanized 5 weeks after crush injury. Experimenters were blinded and tissue processing and quantitative analysis was done as described before. 5F9 but not the vehicle control PBS significantly increased the number of regenerating GAP-43 positive fibers. Significantly more fibers (p<0.001) were found in animals treated with 5F9 at distances 200 μm to 1400 μm, than in vehicle or control antibody treated animals. Animals were treated iv once per week for 4 weeks starting at day 0 with 5F9 (2 mg/kg per dose), with the control antibody 8D1 (2 mg/kg per dose) or with PBS. (FIG. 14B)

Example 11

5F9 Induces Remyelination of Crushed, Damaged Optic Nerve Axons in a Rat Model of Optic Nerve Injury A marker for oligodendrocytes and myelin is myelin-basic protein (MBP). An antibody directed against MBP was used to answer the question if differences occurred in remyelination in the different treatment groups. To visualize the process of remyelination, optic nerve sections of animals treated systemically were fixed with cold (−20° C.) Acetone (10 min), washed 3× (5 min) with Tris Buffered Saline (TBS, Fluka 93312) and were blocked and permeabilised with TBS, containing 5% Bovine Serum Albumin and 1% Triton-X-100 (30 min), at room temperature). Residual BSA and detergent was removed by 2 separate wash steps (5 min each) with TBS. Sections were incubated for 3 h or over night at 4° C. with a polyclonal rabbit anti-MBP antibody (Abcam, ab 2404) diluted 1:50 in 5% BSA/TBS solution. After 3 wash steps with TBS, 0.1% Tween, sections were incubated for 1 h at room temperature with an Alexa Fluor 488-conjugated goat anti-rabbit secondary antibody (Molecular Probes A11034), diluted 1:1000 in 5% BSA/TBS, containing a 1:100 dilution of Bisbenzimid (H33258, 50 μg/ml) to visualize cell nuclei. Before embedding, stained sections were washed 3 times with TBS 0.1% Tween (5 min each step) and with distilled water. Sections were embedded in Fluoromount G, were covered by a coverslip and were stored in the dark for microscopic documentation.

Using a Zeiss fluorescence microscope images of stained longitudinal sections were stored using the Zeiss Axiovison software. Single pictures of each nerve were mounted for analysis using Photoshop Image Analysis software (Adobe). Quantitative analysis was done in two different ways using the composite images of the optic nerves. The MBP-positive area at the lesion site was measured using the Axiovision software. Data analysis and statistical evaluation of data was done with the help of the Graphpad Prism software.

Animals were treated with 5F9 at day 0 and d21 with 2 mg/kg and 10 mg/kg, respectively. Antibody or vehicle were given intraperitoneally or intravenously. Composite images of rat optic nerves.

Figure 15:
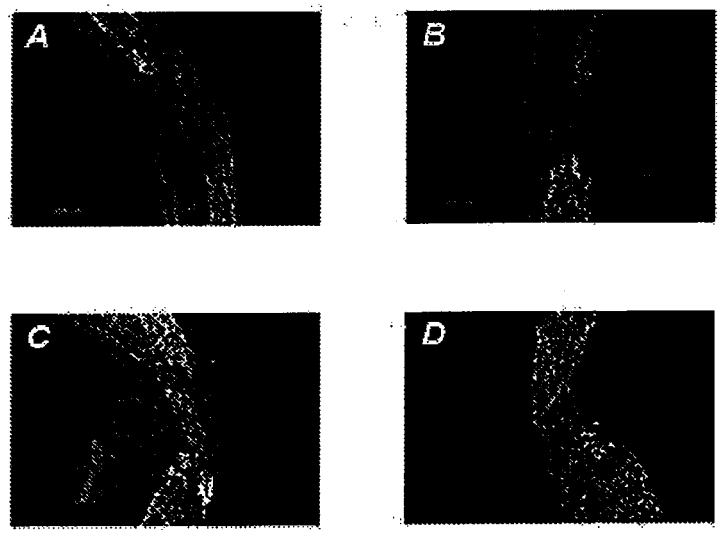
FIG. 15 shows the in vivo remyelinating activity of systemic 5F9 application in an animal model of optic nerve injury. Animals were treated with 5F9 at day 0 and d21 with 2 mg/kg and 10 mg/kg, respectively. Antibody or vehicle were given intraperitoneally or intravenously. Composite images of rat optic nerves. Myelination is visualized using an antibody directed against the myelin marker myelin basic protein MBP. Crush sites are located in the middle of the composite nerves and the area is free in vehicle treated control animals (A and B). In the 5F9 treated animals (C and D), many MBP-positive structures are observed in the middle area (crush center) of the optic nerves.

Myelination is visualized using an antibody directed against the myelin marker myelin basic protein MBP. Crush sites ate located in the middle of the composite nerves and the area is free in vehicle treated control animals (A and B). In the 5F9 treated animals (C and D), many MBP-positive structures are observed in the middle area (crush center) of the optic nerves. (FIG. 15)

Myelination is visualized using an antibody directed against the myelin marker myelin basic protein MBP. The MBP area was measured using the Zeiss Axiovison software.

Figure 16:
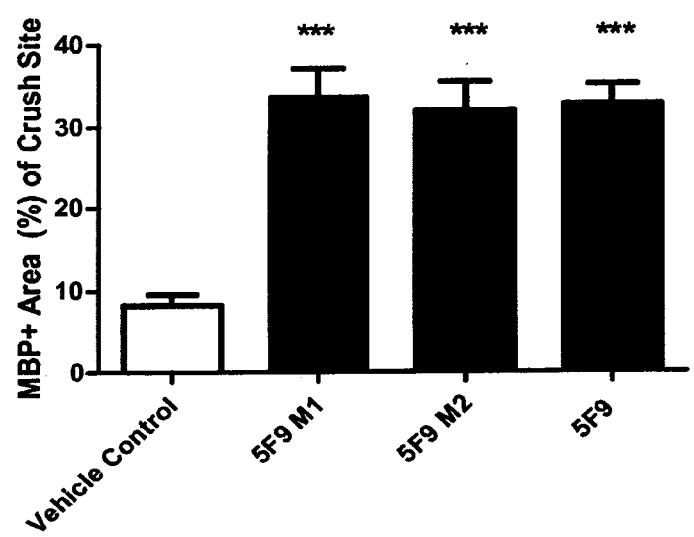
FIG. 16 shows the quantitative effect on remyelination of systemic 5F9 application in an animal model of optic nerve injury.

M1 and M2 are two independent measurements and M is the average measured MPB-positive area. 5F9 increases significantly (p<0.001 versus the vehicle control) the MBP-area of the optic nerve crush site by a factor of 3.5. (FIG. 16).

We claim:

1. An isolated antibody comprising an antigen binding domain, said antibody capable of binding an epitope of a RGM molecule, said antigen binding domain comprising a heavy chain variable domain having three complementary determining regions and a light chain variable domain having three complementary determining regions, wherein the three complementary determining regions of the heavy chain variable domain have the amino acid sequence of SEQ ID NO:57, SEQ ID NO:58 and SEQ ID NO:59 and the three complementary determining regions of the light chain variable domain have the amino acid sequence of SEQ ID NO: 60, SEQ ID NO:61 and SEQ ID NO:62.

2. The antibody of claim 1, wherein said antibody further comprises a human acceptor framework, wherein said human acceptor framework comprises at least one amino acid sequence selected from the group consisting of: SEQ ID NO: 15, 16, 17, 18, 19, 20, 21, 22, 23, 24, 25, 26, 27, 28, 29, 30, 31, 32 and 33.

3. An antigen binding fragment of the antibody of claim 1.

4. A pharmaceutical composition comprising the antibody of claim 1 and a pharmaceutically acceptable carrier.

5. A pharmaceutical composition comprising the antibody of claim 2 and a pharmaceutically acceptable carrier.

6. An isolated antibody comprising an antigen binding domain, said antibody capable of binding an epitope of a RGM molecule, said antigen binding domain comprising a heavy chain variable domain having three complementary determining regions and a light chain variable domain having three complementary determining regions, wherein the three complementary determining regions of the heavy chain variable domain have the amino acid sequence of SEQ ID NO:63, SEQ ID NO:64 and SEQ ID NO:65 and the three complementary determining regions of the light chain variable domain have the amino acid sequence of SEQ ID NO: 66, SEQ ID NO:67 and SEQ ID NO:68.

7. The antibody of claim 6, wherein said antibody further comprises a human acceptor framework, wherein said human acceptor framework comprises at least one amino acid sequence selected from the group consisting of: SEQ ID NO: 15, 16, 17, 18, 19, 20, 21, 22, 23, 24, 25, 26, 27, 28, 29, 30, 31, 32 and 33.

8. An antigen binding fragment of the antibody of claim 6.

9. A pharmaceutical composition comprising the antibody of claim 6 and a pharmaceutically acceptable carrier.

10. A pharmaceutical composition comprising the antibody of claim 7 and a pharmaceutically acceptable carrier.

11. An isolated antibody comprising an antigen binding domain, said antibody capable of binding an epitope of a RGM molecule, said antigen binding domain comprising a heavy chain variable domain and a light chain variable wherein the heavy chain variable domain has the amino acid sequence selected from the group consisting of: SEQ ID NOS: 35, 36, 37, 38, 39, 40, 41, 42, 43, 47, 48, 49 and 50 and wherein the light chain variable domain has the amino acid sequence selected from the group consisting of SEQ ID NO:44, 45, 46, 51, 52, 53 and 54.

12. The antibody of claim 11, wherein the heavy chain variable domain has the amino acid sequence of SEQ ID NO:35 and the light chain variable domain has the amino acid sequence of SEQ ID NO: 44.

13. The antibody of claim 11, wherein the heavy chain variable domain has the amino acid sequence of SEQ ID NO:36 and the light chain variable domain has the amino acid sequence of SEQ ID NO: 44.

14. The antibody of claim 11, wherein the heavy chain variable domain has the amino acid sequence of SEQ ID NO:37 and the light chain variable domain has the amino acid sequence of SEQ ID NO: 44.

15. The antibody of claim 11, wherein the heavy chain variable domain has the amino acid sequence of SEQ ID NO:38 and the light chain variable domain has the amino acid sequence of SEQ ID NO: 44.

16. The antibody of claim 11, wherein the heavy chain variable domain has the amino acid sequence of SEQ ID NO:39 and the light chain variable domain has the amino acid sequence of SEQ ID NO: 44.

17. The antibody of claim 11, wherein the heavy chain variable domain has the amino acid sequence of SEQ ID NO:40 and the light chain variable domain has the amino acid sequence of SEQ ID NO: 44.

18. The antibody of claim 11, wherein the heavy chain variable domain has the amino acid sequence of SEQ ID NO:41 and the light chain variable domain has the amino acid sequence of SEQ ID NO: 44.

19. The antibody of claim 11, wherein the heavy chain variable domain has the amino acid sequence of SEQ ID NO:42 and the light chain variable domain has the amino acid sequence of SEQ ID NO: 44.

20. The antibody of claim 11, wherein the heavy chain variable domain has the amino acid sequence of SEQ ID NO:43 and the light chain variable domain has the amino acid sequence of SEQ ID NO: 44.

21. The antibody of claim 11, wherein the heavy chain variable domain has the amino acid sequence of SEQ ID NO:35 and the light chain variable domain has the amino acid sequence of SEQ ID NO: 45.

22. The antibody of claim 11, wherein the heavy chain variable domain has the amino acid sequence of SEQ ID NO:36 and the light chain variable domain has the amino acid sequence of SEQ ID NO: 45.

23. The antibody of claim 11, wherein the heavy chain variable domain has the amino acid sequence of SEQ ID NO:37 and the light chain variable domain has the amino acid sequence of SEQ ID NO: 45.

24. The antibody of claim 11, wherein the heavy chain variable domain has the amino acid sequence of SEQ ID NO:38 and the light chain variable domain has the amino acid sequence of SEQ ID NO: 45.

25. The antibody of claim 11, wherein the heavy chain variable domain has the amino acid sequence of SEQ ID NO:39 and the light chain variable domain has the amino acid sequence of SEQ ID NO: 45.

26. The antibody of claim 11, wherein the heavy chain variable domain has the amino acid sequence of SEQ ID NO:40 and the light chain variable domain has the amino acid sequence of SEQ ID NO: 45.

27. The antibody of claim 11, wherein the heavy chain variable domain has the amino acid sequence of SEQ ID NO:41 and the light chain variable domain has the amino acid sequence of SEQ ID NO: 45.

28. The antibody of claim 11, wherein the heavy chain variable domain has the amino acid sequence of SEQ ID NO:42 and the light chain variable domain has the amino acid sequence of SEQ ID NO: 45.

29. The antibody of claim 11, wherein the heavy chain variable domain has the amino acid sequence of SEQ ID NO:43 and the light chain variable domain has the amino acid sequence of SEQ ID NO: 45.

30. The antibody of claim 11, wherein the heavy chain variable domain has the amino acid sequence of SEQ ID NO:35 and the light chain variable domain has the amino acid sequence of SEQ ID NO: 46.

31. The antibody of claim 11, wherein the heavy chain variable domain has the amino acid sequence of SEQ ID NO:36 and the light chain variable domain has the amino acid sequence of SEQ ID NO: 46.

32. The antibody of claim 11, wherein the heavy chain variable domain has the amino acid sequence of SEQ ID NO:37 and the light chain variable domain has the amino acid sequence of SEQ ID NO: 46.

33. The antibody of claim 11, wherein the heavy chain variable domain has the amino acid sequence of SEQ ID NO:38 and the light chain variable domain has the amino acid sequence of SEQ ID NO: 46.

34. The antibody of claim 11, wherein the heavy chain variable domain has the amino acid sequence of SEQ ID NO:39 and the light chain variable domain has the amino acid sequence of SEQ ID NO: 46.

35. The antibody of claim 11, wherein the heavy chain variable domain has the amino acid sequence of SEQ ID NO:40 and the light chain variable domain has the amino acid sequence of SEQ ID NO: 46.

36. The antibody of claim 11, wherein the heavy chain variable domain has the amino acid sequence of SEQ ID NO:41 and the light chain variable domain has the amino acid sequence of SEQ ID NO: 46.

37. The antibody of claim 11, wherein the heavy chain variable domain has the amino acid sequence of SEQ ID NO:42 and the light chain variable domain has the amino acid sequence of SEQ ID NO: 46.

38. The antibody of claim 11, wherein the heavy chain variable domain has the amino acid sequence of SEQ ID NO:43 and the light chain variable domain has the amino acid sequence of SEQ ID NO: 46.

39. The antibody of claim 11, wherein the heavy chain variable domain has the amino acid sequence of SEQ ID NO:47 and the light chain variable domain has the amino acid sequence of SEQ ID NO:44.

40. The antibody of claim 11, wherein the heavy chain variable domain has the amino acid sequence of SEQ ID NO:47 and the light chain variable domain has the amino acid sequence of SEQ ID NO:45.

41. The antibody of claim 11, wherein the heavy chain variable domain has the amino acid sequence of SEQ ID NO:47 and the light chain variable domain has the amino acid sequence of SEQ ID NO:46.

42. The antibody of claim 11, wherein the heavy chain variable domain has the amino acid sequence of SEQ ID NO:47 and the light chain variable domain has the amino acid sequence of SEQ ID NO:51.

43. The antibody of claim 11, wherein the heavy chain variable domain has the amino acid sequence of SEQ ID NO:47 and the light chain variable domain has the amino acid sequence of SEQ ID NO:52.

44. The antibody of claim 11, wherein the heavy chain variable domain has the amino acid sequence of SEQ ID NO:47 and the light chain variable domain has the amino acid sequence of SEQ ID NO:53.

45. The antibody of claim 11, wherein the heavy chain variable domain has the amino acid sequence of SEQ ID NO:47 and the light chain variable domain has the amino acid sequence of SEQ ID NO:54.

46. The antibody of claim 11, wherein the heavy chain variable domain has the amino acid sequence of SEQ ID NO:48 and the light chain variable domain has the amino acid sequence of SEQ ID NO:44.

47. The antibody of claim 11, wherein the heavy chain variable domain has the amino acid sequence of SEQ ID NO:48 and the light chain variable domain has the amino acid sequence of SEQ ID NO:45.

48. The antibody of claim 11, wherein the heavy chain variable domain has the amino acid sequence of SEQ ID NO:48 and the light chain variable domain has the amino acid sequence of SEQ ID NO:46.

49. The antibody of claim 11, wherein the heavy chain variable domain has the amino acid sequence of SEQ ID NO:48 and the light chain variable domain has the amino acid sequence of SEQ ID NO:51.

50. The antibody of claim 11, wherein the heavy chain variable domain has the amino acid sequence of SEQ ID NO:48 and the light chain variable domain has the amino acid sequence of SEQ ID NO:52.

51. The antibody of claim 11, wherein the heavy chain variable domain has the amino acid sequence of SEQ ID NO:48 and the light chain variable domain has the amino acid sequence of SEQ ID NO:53.

52. The antibody of claim 11, wherein the heavy chain variable domain has the amino acid sequence of SEQ ID NO:48 and the light chain variable domain has the amino acid sequence of SEQ ID NO:54.

53. A pharmaceutical composition comprising the antibody of any one of claims 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 and a pharmaceutically acceptable carrier.

54. The antibody of claim 1, wherein the antibody is a monoclonal antibody, a chimeric antibody, a CDR-grafted antibody, a humanized antibody, a multispecific antibody, a dual specific antibody or a bispecific antibody.

55. The antibody of claim 2, wherein the antibody is a monoclonal antibody, a chimeric antibody, a CDR-grafted antibody, a humanized antibody, a multispecific antibody, a dual specific antibody or a bispecific antibody.

56. The antibody of claim 6, wherein the antibody is a monoclonal antibody, a chimeric antibody, a CDR-grafted antibody, a humanized antibody, a multispecific antibody, a dual specific antibody or a bispecific antibody.

57. The antibody of claim 7, wherein the antibody is a monoclonal antibody, a chimeric antibody, a CDR-grafted antibody, a humanized antibody, a multispecific antibody, a dual specific antibody or a bispecific antibody.

58. The antibody of claim 11, wherein the antibody is a monoclonal antibody, a chimeric antibody, a CDR-grafted antibody, a humanized antibody, a multispecific antibody, a dual specific antibody or a bispecific antibody.

59. The antibody of claim 11, wherein the heavy chain variable domain has the amino acid sequence of SEQ ID NO:49 and the light chain variable domain has the amino acid sequence of SEQ ID NO:44.

60. The antibody of claim 11, wherein the heavy chain variable domain has the amino acid sequence of SEQ ID NO:50 and the light chain variable domain has the amino acid sequence of SEQ ID NO:44.

61. The antibody of claim 11, wherein the heavy chain variable donain has the amino acid sequence of SEQ ID NO:49 and the light chain variable domain has the amino acid sequence of SEQ ID NO:45.

62. The antibody of claim 11, wherein the heavy chain variable donain has the amino acid sequence of SEQ ID NO:50 and the light chain variable domain has the amino acid sequence of SEQ ID NO:45.

63. The antibody of claim 11, wherein the heavy chain variable domain has the amino acid sequence of SEQ ID NO:49 and the light chain variable domain has the amino acid sequence of SEQ ID NO:46.

64. The antibody of claim 11, wherein the heavy chain variable domain has the amino acid sequence of SEQ ID NO:50 and the light chain variable domain has the amino acid sequence of SEQ ID NO:46.

65. The antibody of claim 11, wherein the heavy chain variable doamin has the amino acid sequence of SEQ ID NO:50 and the light chain variable domain has the amino acid sequence of SEQ ID NO:51.

66. The antibody of claim 11, wherein the heavy chain variable domain has the amino acid sequence of SEQ ID NO:50 and the light chain variable domain has the amino acid sequence of SEQ ID NO:52.

67. The antibody of claim 11, wherein the heavy chain variable domain has the amino acid sequence of SEQ ID NO:50 and the light chain variable domain has the amino acid sequence of SEQ ID NO:53.

68. The antibody of claim 11, wherein the heavy chain variable domain has the amino acid sequence of SEQ ID NO:50 and the light chain variable domain has the amino acid sequence of SEQ ID NO:54.

69. A pharmaceutical composition comprising the antibody of claims 59, 60, 61, 62, 63, 64, 65, 66, 67, or 68 and a pharmaceutical acceptable carrier.

* * * * *

UNITED STATES PATENT AND TRADEMARK OFFICE
CERTIFICATE OF CORRECTION

| | | |
|---|---|---|
| PATENT NO. | : 8,962,803 B2 | Page 1 of 1 |
| APPLICATION NO. | : 12/389927 | |
| DATED | : February 24, 2015 | |
| INVENTOR(S) | : Mueller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 145 days.

Signed and Sealed this
Nineteenth Day of January, 2016

Michelle K. Lee
*Director of the United States Patent and Trademark Office*

```
                         SEQUENCE LISTING

<160> NUMBER OF SEQ ID NOS: 68

<210> SEQ ID NO 1
<211> LENGTH: 1353
<212> TYPE: DNA
<213> ORGANISM: Homo sapiens
<220> FEATURE:
<221> NAME/KEY: CDS
<222> LOCATION: (1)..(1353)

<400> SEQUENCE: 1 atg cag ccg cca agg gag agg cta gtg gta aca ggc cga gct gga tgg      48
Met Gln Pro Pro Arg Glu Arg Leu Val Val Thr Gly Arg Ala Gly Trp
1               5                   10                  15 atg ggt atg ggg aga ggg gca gga cgt tca gcc ctg gga ttc tgg ccg      96
Met Gly Met Gly Arg Gly Ala Gly Arg Ser Ala Leu Gly Phe Trp Pro
            20                  25                  30 acc ctc gcc ttc ctt ctc tgc agc ttc ccc gca gcc acc tcc ccg tgc     144
Thr Leu Ala Phe Leu Leu Cys Ser Phe Pro Ala Ala Thr Ser Pro Cys
        35                  40                  45 aag atc ctc aag tgc aac tct gag ttc tgg agc gcc acg tcg ggc agc     192
Lys Ile Leu Lys Cys Asn Ser Glu Phe Trp Ser Ala Thr Ser Gly Ser
    50                  55                  60 cac gcc cca gcc tca gac gac acc ccc gag ttc tgt gca gcc ttg cgc     240
His Ala Pro Ala Ser Asp Asp Thr Pro Glu Phe Cys Ala Ala Leu Arg
65                  70                  75                  80 agc tac gcc ctg tgc acg cgg cgg acg gcc cgc acc tgc cgg ggt gac     288
Ser Tyr Ala Leu Cys Thr Arg Arg Thr Ala Arg Thr Cys Arg Gly Asp
                85                  90                  95 ctg gcc tac cac tcg gcc gtc cat ggc ata gag gac ctc atg agc cag     336
Leu Ala Tyr His Ser Ala Val His Gly Ile Glu Asp Leu Met Ser Gln
            100                 105                 110 cac aac tgc tcc aag gat ggc ccc acc tcg cag cca cgc ctg cgc acg     384
His Asn Cys Ser Lys Asp Gly Pro Thr Ser Gln Pro Arg Leu Arg Thr
        115                 120                 125 ctc cca ccg gcc gga gac agc cag gag cgc tcg gac agc ccc gag atc     432
Leu Pro Pro Ala Gly Asp Ser Gln Glu Arg Ser Asp Ser Pro Glu Ile
    130                 135                 140 tgc cat tac gag aag agc ttt cac aag cac tcg gcc acc ccc aac tac     480
Cys His Tyr Glu Lys Ser Phe His Lys His Ser Ala Thr Pro Asn Tyr
145                 150                 155                 160 acg cac tgt ggc ctc ttc ggg gac cca cac ctc agg act ttc acc gac     528
Thr His Cys Gly Leu Phe Gly Asp Pro His Leu Arg Thr Phe Thr Asp
                165                 170                 175 cgc ttc cag acc tgc aag gtg cag ggc gcc tgg ccg ctc atc gac aat     576
Arg Phe Gln Thr Cys Lys Val Gln Gly Ala Trp Pro Leu Ile Asp Asn
            180                 185                 190 aat tac ctg aac gtg cag gcc acc aac acg cct gtg ctg ccc ggc tca     624
Asn Tyr Leu Asn Val Gln Ala Thr Asn Thr Pro Val Leu Pro Gly Ser
        195                 200                 205 gcg gcc act gcc acc agc aag ctc acc atc atc ttc aag aac ttc cag     672
Ala Ala Thr Ala Thr Ser Lys Leu Thr Ile Ile Phe Lys Asn Phe Gln
    210                 215                 220 gag tgt gtg gac cag aag gtg tac cag gct gag atg gac gag ctc ccg     720
Glu Cys Val Asp Gln Lys Val Tyr Gln Ala Glu Met Asp Glu Leu Pro
225                 230                 235                 240 gcc gcc ttc gtg gat ggc tct aag aac ggt ggg gac aag cac ggg gcc     768
Ala Ala Phe Val Asp Gly Ser Lys Asn Gly Gly Asp Lys His Gly Ala
                245                 250                 255
```

```
aac agc ctg aag atc act gag aag gtg tca ggc cag cac gtg gag atc    816
Asn Ser Leu Lys Ile Thr Glu Lys Val Ser Gly Gln His Val Glu Ile
        260                 265                 270 cag gcc aag tac atc ggc acc acc atc gtg gtg cgc cag gtg ggc cgc    864
Gln Ala Lys Tyr Ile Gly Thr Thr Ile Val Val Arg Gln Val Gly Arg
            275                 280                 285 tac ctg acc ttt gcc gtc cgc atg cca gag gaa gtg gtc aat gct gtg    912
Tyr Leu Thr Phe Ala Val Arg Met Pro Glu Glu Val Val Asn Ala Val
        290                 295                 300 gag gac tgg gac agc cag ggt ctc tac ctc tgc ctg cgg ggc tgc ccc    960
Glu Asp Trp Asp Ser Gln Gly Leu Tyr Leu Cys Leu Arg Gly Cys Pro
305                 310                 315                 320 ctc aac cag cag atc gac ttc cag gcc ttc cac acc aat gct gag ggc   1008
Leu Asn Gln Gln Ile Asp Phe Gln Ala Phe His Thr Asn Ala Glu Gly
                325                 330                 335 acc ggt gcc cgc agg ctg gca gcc gcc agc cct gca ccc aca gcc ccc   1056
Thr Gly Ala Arg Arg Leu Ala Ala Ala Ser Pro Ala Pro Thr Ala Pro
            340                 345                 350 gag acc ttc cca tac gag aca gcc gtg gcc aag tgc aag gag aag ctg   1104
Glu Thr Phe Pro Tyr Glu Thr Ala Val Ala Lys Cys Lys Glu Lys Leu
        355                 360                 365 ccg gtg gag gac ctg tac tac cag gcc tgc gtc ttc gac ctc ctc acc   1152
Pro Val Glu Asp Leu Tyr Tyr Gln Ala Cys Val Phe Asp Leu Leu Thr
370                 375                 380 acg ggc gac gtg aac ttc aca ctg gcc gcc tac tac gcg ttg gag gat   1200
Thr Gly Asp Val Asn Phe Thr Leu Ala Ala Tyr Tyr Ala Leu Glu Asp
385                 390                 395                 400 gtc aag atg ctc cac tcc aac aaa gac aaa ctg cac ctg tat gag agg   1248
Val Lys Met Leu His Ser Asn Lys Asp Lys Leu His Leu Tyr Glu Arg
                405                 410                 415 act cgg gac ctg cca ggc agg gcg gct gcg ggg ctg ccc ctg gcc ccc   1296
Thr Arg Asp Leu Pro Gly Arg Ala Ala Ala Gly Leu Pro Leu Ala Pro
            420                 425                 430 cgg ccc ctc ctg ggc gcc ctc gtc ccg ctc ctg gcc ctg ctc cct gtg   1344
Arg Pro Leu Leu Gly Ala Leu Val Pro Leu Leu Ala Leu Leu Pro Val
        435                 440                 445 ttc tgc tag                                                       1353
Phe Cys
    450

<210> SEQ ID NO 2
<211> LENGTH: 450
<212> TYPE: PRT
<213> ORGANISM: Homo sapiens

<400> SEQUENCE: 2

Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
            20                  25                  30

Thr Leu Ala Phe Leu Leu Cys Ser Phe Pro Ala Ala Thr Ser Pro Cys
        35                  40                  45

Lys Ile Leu Lys Cys Asn Ser Glu Phe Trp Ser Ala Thr Ser Gly Ser
    50                  55                  60

His Ala Pro Ala Ser Asp Asp Thr Pro Glu Phe Cys Ala Ala Leu Arg
65                  70                  75                  80

Ser Tyr Ala Leu Cys Thr Arg Arg Thr Ala Arg Thr Cys Arg Gly Asp
                85                  90                  95
```

Leu Ala Tyr His Ser Ala Val His Gly Ile Glu Asp Leu Met Ser Gln
                100                 105                 110

His Asn Cys Ser Lys Asp Gly Pro Thr Ser Gln Pro Arg Leu Arg Thr
        115                 120                 125

Leu Pro Pro Ala Gly Asp Ser Gln Glu Arg Ser Asp Ser Pro Glu Ile
    130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
                165                 170                 175

Arg Phe Gln Thr Cys Lys Val Gln Gly Ala Trp Pro Leu Ile Asp Asn
        180                 185                 190

Asn Tyr Leu Asn Val Gln Ala Thr Asn Thr Pro Val Leu Pro Gly Ser
    195                 200                 205

Ala Ala Thr Ala Thr Ser Lys Leu Thr Ile Ile Phe Lys Asn Phe Gln
210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
                245                 250                 255

Asn Ser Leu Lys Ile Thr Glu Lys Val Ser Gly Gln His Val Glu Ile
        260                 265                 270

Gln Ala Lys Tyr Ile Gly Thr Thr Ile Val Val Arg Gln Val Gly Arg
    275                 280                 285

Tyr Leu Thr Phe Ala Val Arg Met Pro Glu Glu Val Val Asn Ala Val
290                 295                 300

Glu Asp Trp Asp Ser Gln Gly Leu Tyr Leu Cys Leu Arg Gly Cys Pro
305                 310                 315                 320

Leu Asn Gln Gln Ile Asp Phe Gln Ala Phe His Thr Asn Ala Glu Gly
                325                 330                 335

Thr Gly Ala Arg Arg Leu Ala Ala Ala Ser Pro Ala Pro Thr Ala Pro
        340                 345                 350

Glu Thr Phe Pro Tyr Glu Thr Ala Val Ala Lys Cys Lys Glu Lys Leu
    355                 360                 365

Pro Val Glu Asp Leu Tyr Tyr Gln Ala Cys Val Phe Asp Leu Leu Thr
370                 375                 380

Thr Gly Asp Val Asn Phe Thr Leu Ala Ala Tyr Tyr Ala Leu Glu Asp
385                 390                 395                 400

Val Lys Met Leu His Ser Asn Lys Asp Lys Leu His Leu Tyr Glu Arg
                405                 410                 415

Thr Arg Asp Leu Pro Gly Arg Ala Ala Ala Gly Leu Pro Leu Ala Pro
        420                 425                 430

Arg Pro Leu Leu Gly Ala Leu Val Pro Leu Leu Ala Leu Leu Pro Val
    435                 440                 445

Phe Cys
    450

<210> SEQ ID NO 3
<211> LENGTH: 1929
<212> TYPE: DNA
<213> ORGANISM: Artificial
<220> FEATURE:
<223> OTHER INFORMATION: hRGMA fc
<220> FEATURE:
<221> NAME/KEY: CDS
<222> LOCATION: (1)..(1929)

```
<220> FEATURE:
<221> NAME/KEY: sig_peptide
<222> LOCATION: (1)..(102)
<220> FEATURE:
<221> NAME/KEY: misc_feature
<222> LOCATION: (103)..(1230)
<223> OTHER INFORMATION: hRGMA Fragment 47-422
<220> FEATURE:
<221> NAME/KEY: misc_feature
<222> LOCATION: (1231)..(1929)
<223> OTHER INFORMATION: fc portion

<400> SEQUENCE: 3 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcg cgc cgt acg      96
Gly Ser Thr Gly Asp Ala Ala Gln Pro Ala Arg Arg Ala Arg Arg Thr
            20                  25                  30 aag ctt ccg tgc aag atc ctc aag tgc aac tct gag ttc tgg agc gcc     144
Lys Leu Pro Cys Lys Ile Leu Lys Cys Asn Ser Glu Phe Trp Ser Ala
        35                  40                  45 acg tcg ggc agc cac gcc cca gcc tca gac gac acc ccc gag ttc tgt     192
Thr Ser Gly Ser His Ala Pro Ala Ser Asp Asp Thr Pro Glu Phe Cys
    50                  55                  60 gca gcc ttg cgc agc tac gcc ctg tgc acg cgg cgg acg gcc cgc acc     240
Ala Ala Leu Arg Ser Tyr Ala Leu Cys Thr Arg Arg Thr Ala Arg Thr
65                  70                  75                  80 tgc cgg ggt gac ctg gcc tac cac tcg gcc gtc cat ggc ata gag gac     288
Cys Arg Gly Asp Leu Ala Tyr His Ser Ala Val His Gly Ile Glu Asp
                85                  90                  95 ctc atg agc cag cac aac tgc tcc aag gat ggc ccc acc tcg cag cca     336
Leu Met Ser Gln His Asn Cys Ser Lys Asp Gly Pro Thr Ser Gln Pro
            100                 105                 110 cgc ctg cgc acg ctc cca ccg gcc gga gac agc cag gag cgc tcg gac     384
Arg Leu Arg Thr Leu Pro Pro Ala Gly Asp Ser Gln Glu Arg Ser Asp
        115                 120                 125 agc ccc gag atc tgc cat tac gag aag agc ttt cac aag cac tcg gcc     432
Ser Pro Glu Ile Cys His Tyr Glu Lys Ser Phe His Lys His Ser Ala
    130                 135                 140 acc ccc aac tac acg cac tgt ggc ctc ttc ggg gac cca cac ctc agg     480
Thr Pro Asn Tyr Thr His Cys Gly Leu Phe Gly Asp Pro His Leu Arg
145                 150                 155                 160 act ttc acc gac cgc ttc cag acc tgc aag gtg cag ggc gcc tgg ccg     528
Thr Phe Thr Asp Arg Phe Gln Thr Cys Lys Val Gln Gly Ala Trp Pro
                165                 170                 175 ctc atc gac aat aat tac ctg aac gtg cag gtc acc aac acg cct gtg     576
Leu Ile Asp Asn Asn Tyr Leu Asn Val Gln Val Thr Asn Thr Pro Val
            180                 185                 190 ctg ccc ggc tca gcg gcc act gcc acc agc aag ctc acc atc atc ttc     624
Leu Pro Gly Ser Ala Ala Thr Ala Thr Ser Lys Leu Thr Ile Ile Phe
        195                 200                 205 aag aac ttc cag gag tgt gtg gac cag aag gtg tac cag gct gag atg     672
Lys Asn Phe Gln Glu Cys Val Asp Gln Lys Val Tyr Gln Ala Glu Met
    210                 215                 220 gac gag ctc ccg gcc gcc ttc gtg gat ggc tct aag aac ggt ggg gac     720
Asp Glu Leu Pro Ala Ala Phe Val Asp Gly Ser Lys Asn Gly Gly Asp
225                 230                 235                 240 aag cac ggg gcc aac agc ctg aag atc act gag aag gtg tca ggc cag     768
Lys His Gly Ala Asn Ser Leu Lys Ile Thr Glu Lys Val Ser Gly Gln
                245                 250                 255 cac gtg gag atc cag gcc aag tac atc ggc acc acc atc gtg gtg cgc     816
```

```
              His Val Glu Ile Gln Ala Lys Tyr Ile Gly Thr Thr Ile Val Val Arg
                          260                 265                 270 cag gtg ggc cgc tac ctg acc ttt gcc gtc cgc atg cca gag gaa gtg        864
Gln Val Gly Arg Tyr Leu Thr Phe Ala Val Arg Met Pro Glu Glu Val
            275                 280                 285 gtc aat gct gtg gag gac tgg gac agc cag ggt ctc tac ctc tgc ctg        912
Val Asn Ala Val Glu Asp Trp Asp Ser Gln Gly Leu Tyr Leu Cys Leu
290                 295                 300 cgg ggc tgc ccc ctc aac cag cag atc gac ttc cag gcc ttc cac acc        960
Arg Gly Cys Pro Leu Asn Gln Gln Ile Asp Phe Gln Ala Phe His Thr
305                 310                 315                 320 aat gct gag ggc acc ggt gcc cgc agg ctg gca gcc gcc agc cct gca       1008
Asn Ala Glu Gly Thr Gly Ala Arg Arg Leu Ala Ala Ala Ser Pro Ala
                325                 330                 335 ccc aca gcc ccc gag acc ttc cca tac gag aca gcc gtg gcc aag tgc       1056
Pro Thr Ala Pro Glu Thr Phe Pro Tyr Glu Thr Ala Val Ala Lys Cys
            340                 345                 350 aag gag aag ctg ccg gtg gag gac ctg tac tac cag gcc tgc gtc ttc       1104
Lys Glu Lys Leu Pro Val Glu Asp Leu Tyr Tyr Gln Ala Cys Val Phe
        355                 360                 365 gac ctc ctc acc acg ggc gac gtg aac ttc aca ctg gcc gcc tac tac       1152
Asp Leu Leu Thr Thr Gly Asp Val Asn Phe Thr Leu Ala Ala Tyr Tyr
370                 375                 380 gcg ttg gag gat gtc aag atg ctc cac tcc aac aaa gac aaa ctg cac       1200
Ala Leu Glu Asp Val Lys Met Leu His Ser Asn Lys Asp Lys Leu His
385                 390                 395                 400 ctg tat gag agg act cgg gac ctg cca ggc ttg aat tct gca gat atc       1248
Leu Tyr Glu Arg Thr Arg Asp Leu Pro Gly Leu Asn Ser Ala Asp Ile
                405                 410                 415 gag gga cga atg gat cca ccg tgc cca gca cct gaa ctc ctg ggg gga       1296
Glu Gly Arg Met Asp Pro Pro Cys Pro Ala Pro Glu Leu Leu Gly Gly
            420                 425                 430 ccg tca gtc ttc ctc ttc ccc cca aaa ccc aag gac acc ctc atg atc       1344
Pro Ser Val Phe Leu Phe Pro Pro Lys Pro Lys Asp Thr Leu Met Ile
        435                 440                 445 tcc cgg acc cct gag gtc aca tgc gtg gtg gtg gac gtg agc cac gaa       1392
Ser Arg Thr Pro Glu Val Thr Cys Val Val Val Asp Val Ser His Glu
450                 455                 460 gac cct gag gtc aag ttc aac tgg tac gtg gac ggc gtg gag gtg cat       1440
Asp Pro Glu Val Lys Phe Asn Trp Tyr Val Asp Gly Val Glu Val His
465                 470                 475                 480 aat gcc aag aca aag ccg cgg gag gag cag tac aac agc acg tac cgt       1488
Asn Ala Lys Thr Lys Pro Arg Glu Glu Gln Tyr Asn Ser Thr Tyr Arg
                485                 490                 495 gtg gtc agc gtc ctc acc gtc ctg cac cag gac tgg ctg aat ggc aag       1536
Val Val Ser Val Leu Thr Val Leu His Gln Asp Trp Leu Asn Gly Lys
            500                 505                 510 gag tac aag tgc aag gtc tcc aac aaa gcc ctc cca gcc ccc atc gag       1584
Glu Tyr Lys Cys Lys Val Ser Asn Lys Ala Leu Pro Ala Pro Ile Glu
        515                 520                 525 aaa acc atc tcc aaa gcc aaa ggg cag ccc cga gaa cca cag gtg tac       1632
Lys Thr Ile Ser Lys Ala Lys Gly Gln Pro Arg Glu Pro Gln Val Tyr
530                 535                 540 acc ctg ccc cca tcc cgg gag gag atg acc aag aac cag gtc agc ctg       1680
Thr Leu Pro Pro Ser Arg Glu Glu Met Thr Lys Asn Gln Val Ser Leu
545                 550                 555                 560 acc tgc ctg gtc aaa ggc ttc tat ccc agc gac atc gcc gtg gag tgg       1728
Thr Cys Leu Val Lys Gly Phe Tyr Pro Ser Asp Ile Ala Val Glu Trp
                565                 570                 575
```

```
gag agc aat ggg cag ccg gag aac aac tac aag acc acg cct ccc gtg     1776
Glu Ser Asn Gly Gln Pro Glu Asn Asn Tyr Lys Thr Thr Pro Pro Val
        580                 585                 590 ctg gac tcc gac ggc tcc ttc ttc ctc tat agc aag ctc acc gtg gac     1824
Leu Asp Ser Asp Gly Ser Phe Phe Leu Tyr Ser Lys Leu Thr Val Asp
            595                 600                 605 aag agc agg tgg cag cag ggg aac gtc ttc tca tgc tcc gtg atg cat     1872
Lys Ser Arg Trp Gln Gln Gly Asn Val Phe Ser Cys Ser Val Met His
610                 615                 620 gag gct ctg cac aac cac tac acg cag aag agc ctc tcc ctg tct ccg     1920
Glu Ala Leu His Asn His Tyr Thr Gln Lys Ser Leu Ser Leu Ser Pro
625                 630                 635                 640 ggt aaa tga                                                          1929
Gly Lys <210> SEQ ID NO 4
<211> LENGTH: 642
<212> TYPE: PRT
<213> ORGANISM: Artificial
<220> FEATURE:
<223> OTHER INFORMATION: Synthetic Construct

<400> SEQUENCE: 4

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Pro Cys Lys Ile Leu Lys Cys Asn Ser Glu Phe Trp Ser Ala
        35                  40                  45

Thr Ser Gly Ser His Ala Pro Ala Ser Asp Asp Thr Pro Glu Phe Cys
    50                  55                  60

Ala Ala Leu Arg Ser Tyr Ala Leu Cys Thr Arg Arg Thr Ala Arg Thr
65                  70                  75                  80

Cys Arg Gly Asp Leu Ala Tyr His Ser Ala Val His Gly Ile Glu Asp
                85                  90                  95

Leu Met Ser Gln His Asn Cys Ser Lys Asp Gly Pro Thr Ser Gln Pro
            100                 105                 110

Arg Leu Arg Thr Leu Pro Pro Ala Gly Asp Ser Gln Glu Arg Ser Asp
        115                 120                 125

Ser Pro Glu Ile Cys His Tyr Glu Lys Ser Phe His Lys His Ser Ala
    130                 135                 140

Thr Pro Asn Tyr Thr His Cys Gly Leu Phe Gly Asp Pro His Leu Arg
145                 150                 155                 160

Thr Phe Thr Asp Arg Phe Gln Thr Cys Lys Val Gln Gly Ala Trp Pro
                165                 170                 175

Leu Ile Asp Asn Asn Tyr Leu Asn Val Gln Val Thr Asn Thr Pro Val
            180                 185                 190

Leu Pro Gly Ser Ala Ala Thr Ala Thr Ser Lys Leu Thr Ile Ile Phe
        195                 200                 205

Lys Asn Phe Gln Glu Cys Val Asp Gln Lys Val Tyr Gln Ala Glu Met
    210                 215                 220

Asp Glu Leu Pro Ala Ala Phe Val Asp Gly Ser Lys Asn Gly Gly Asp
225                 230                 235                 240

Lys His Gly Ala Asn Ser Leu Lys Ile Thr Glu Lys Val Ser Gly Gln
                245                 250                 255

His Val Glu Ile Gln Ala Lys Tyr Ile Gly Thr Thr Ile Val Val Arg
            260                 265                 270
```

```
Gln Val Gly Arg Tyr Leu Thr Phe Ala Val Arg Met Pro Glu Glu Val
            275                 280                 285

Val Asn Ala Val Glu Asp Trp Asp Ser Gln Gly Leu Tyr Leu Cys Leu
290                 295                 300

Arg Gly Cys Pro Leu Asn Gln Gln Ile Asp Phe Gln Ala Phe His Thr
305                 310                 315                 320

Asn Ala Glu Gly Thr Gly Ala Arg Arg Leu Ala Ala Ala Ser Pro Ala
                325                 330                 335

Pro Thr Ala Pro Glu Thr Phe Pro Tyr Glu Thr Ala Val Ala Lys Cys
                340                 345                 350

Lys Glu Lys Leu Pro Val Glu Asp Leu Tyr Tyr Gln Ala Cys Val Phe
            355                 360                 365

Asp Leu Leu Thr Thr Gly Asp Val Asn Phe Thr Leu Ala Ala Tyr Tyr
370                 375                 380

Ala Leu Glu Asp Val Lys Met Leu His Ser Asn Lys Asp Lys Leu His
385                 390                 395                 400

Leu Tyr Glu Arg Thr Arg Asp Leu Pro Gly Leu Asn Ser Ala Asp Ile
                405                 410                 415

Glu Gly Arg Met Asp Pro Cys Pro Ala Pro Glu Leu Leu Gly Gly
                420                 425                 430

Pro Ser Val Phe Leu Phe Pro Pro Lys Pro Lys Asp Thr Leu Met Ile
            435                 440                 445

Ser Arg Thr Pro Glu Val Thr Cys Val Val Val Asp Val Ser His Glu
450                 455                 460

Asp Pro Glu Val Lys Phe Asn Trp Tyr Val Asp Gly Val Glu Val His
465                 470                 475                 480

Asn Ala Lys Thr Lys Pro Arg Glu Glu Gln Tyr Asn Ser Thr Tyr Arg
                485                 490                 495

Val Val Ser Val Leu Thr Val Leu His Gln Asp Trp Leu Asn Gly Lys
            500                 505                 510

Glu Tyr Lys Cys Lys Val Ser Asn Lys Ala Leu Pro Ala Pro Ile Glu
            515                 520                 525

Lys Thr Ile Ser Lys Ala Lys Gly Gln Pro Arg Glu Pro Gln Val Tyr
            530                 535                 540

Thr Leu Pro Pro Ser Arg Glu Glu Met Thr Lys Asn Gln Val Ser Leu
545                 550                 555                 560

Thr Cys Leu Val Lys Gly Phe Tyr Pro Ser Asp Ile Ala Val Glu Trp
                565                 570                 575

Glu Ser Asn Gly Gln Pro Glu Asn Asn Tyr Lys Thr Thr Pro Pro Val
                580                 585                 590

Leu Asp Ser Asp Gly Ser Phe Phe Leu Tyr Ser Lys Leu Thr Val Asp
            595                 600                 605

Lys Ser Arg Trp Gln Gln Gly Asn Val Phe Ser Cys Ser Val Met His
            610                 615                 620

Glu Ala Leu His Asn His Tyr Thr Gln Lys Ser Leu Ser Leu Ser Pro
625                 630                 635                 640

Gly Lys

<210> SEQ ID NO 5
<211> LENGTH: 1167
<212> TYPE: DNA
<213> ORGANISM: Artificial
<220> FEATURE:
<223> OTHER INFORMATION: hRGMA LC fc
```

```
<220> FEATURE:
<221> NAME/KEY: CDS
<222> LOCATION: (1)..(1167)
<220> FEATURE:
<221> NAME/KEY: sig_peptide
<222> LOCATION: (1)..(102)
<220> FEATURE:
<221> NAME/KEY: misc_feature
<222> LOCATION: (103)..(468)
<223> OTHER INFORMATION: hRGMA Fragment 47-168
<220> FEATURE:
<221> NAME/KEY: misc_feature
<222> LOCATION: (469)..(1167)
<223> OTHER INFORMATION: fc portion

<400> SEQUENCE: 5 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcg cgc gtc acg      96
Gly Ser Thr Gly Asp Ala Ala Gln Pro Ala Arg Arg Ala Arg Arg Thr
            20                  25                  30 aag ctt ccg tgc aag atc ctc aag tgc aac tct gag ttc tgg agc gcc     144
Lys Leu Pro Cys Lys Ile Leu Lys Cys Asn Ser Glu Phe Trp Ser Ala
        35                  40                  45 acg tcg ggc agc cac gcc cca gcc tca gac gac acc ccc gag ttc tgt     192
Thr Ser Gly Ser His Ala Pro Ala Ser Asp Asp Thr Pro Glu Phe Cys
    50                  55                  60 gca gcc ttg cgc agc tac gcc ctg tgc acg cgg cgg acg gcc cgc acc     240
Ala Ala Leu Arg Ser Tyr Ala Leu Cys Thr Arg Arg Thr Ala Arg Thr
65                  70                  75                  80 tgc cgg ggt gac ctg gcc tac cac tcg gcc gtc cat ggc ata gag gac     288
Cys Arg Gly Asp Leu Ala Tyr His Ser Ala Val His Gly Ile Glu Asp
                85                  90                  95 ctc atg agc cag cac aac tgc tcc aag gat ggc ccc acc tcg cag cca     336
Leu Met Ser Gln His Asn Cys Ser Lys Asp Gly Pro Thr Ser Gln Pro
            100                 105                 110 cgc ctg cgc acg ctc cca ccg gcc gga gac agc cag gag cgc tcg gac     384
Arg Leu Arg Thr Leu Pro Pro Ala Gly Asp Ser Gln Glu Arg Ser Asp
        115                 120                 125 agc ccc gag atc tgc cat tac gag aag agc ttt cac aag cac tcg gcc     432
Ser Pro Glu Ile Cys His Tyr Glu Lys Ser Phe His Lys His Ser Ala
130                 135                 140 acc ccc aac tac acg cac tgt ggc ctc ttc ggg gac ttg aat tct gca     480
Thr Pro Asn Tyr Thr His Cys Gly Leu Phe Gly Asp Leu Asn Ser Ala
145                 150                 155                 160 gat atc gag gga cga atg gat cca ccg tgc cca gca cct gaa ctc ctg     528
Asp Ile Glu Gly Arg Met Asp Pro Pro Cys Pro Ala Pro Glu Leu Leu
                165                 170                 175 ggg gga ccg tca gtc ttc ctc ttc ccc cca aaa ccc aag gac acc ctc     576
Gly Gly Pro Ser Val Phe Leu Phe Pro Pro Lys Pro Lys Asp Thr Leu
            180                 185                 190 atg atc tcc cgg acc cct gag gtc aca tgc gtg gtg gtg gac gtg agc     624
Met Ile Ser Arg Thr Pro Glu Val Thr Cys Val Val Val Asp Val Ser
        195                 200                 205 cac gaa gac cct gag gtc aag ttc aac tgg tac gtg gac ggc gtg gag     672
His Glu Asp Pro Glu Val Lys Phe Asn Trp Tyr Val Asp Gly Val Glu
    210                 215                 220 gtg cat aat gcc aag aca aag ccg cgg gag gag cag tac aac agc acg     720
Val His Asn Ala Lys Thr Lys Pro Arg Glu Glu Gln Tyr Asn Ser Thr
225                 230                 235                 240 tac cgt gtg gtc agc gtc ctc acc gtc ctg cac cag gac tgg ctg aat     768
Tyr Arg Val Val Ser Val Leu Thr Val Leu His Gln Asp Trp Leu Asn
```

```
                    245                 250                 255
ggc aag gag tac aag tgc aag gtc tcc aac aaa gcc ctc cca gcc ccc      816
Gly Lys Glu Tyr Lys Cys Lys Val Ser Asn Lys Ala Leu Pro Ala Pro
            260                 265                 270 atc gag aaa acc atc tcc aaa gcc aaa ggg cag ccc cga gaa cca cag      864
Ile Glu Lys Thr Ile Ser Lys Ala Lys Gly Gln Pro Arg Glu Pro Gln
        275                 280                 285 gtg tac acc ctg ccc cca tcc cgg gag gag atg acc aag aac cag gtc      912
Val Tyr Thr Leu Pro Pro Ser Arg Glu Glu Met Thr Lys Asn Gln Val
    290                 295                 300 agc ctg acc tgc ctg gtc aaa ggc ttc tat ccc agc gac atc gcc gtg      960
Ser Leu Thr Cys Leu Val Lys Gly Phe Tyr Pro Ser Asp Ile Ala Val
305                 310                 315                 320 gag tgg gag agc aat ggg cag ccg gag aac aac tac aag acc acg cct     1008
Glu Trp Glu Ser Asn Gly Gln Pro Glu Asn Asn Tyr Lys Thr Thr Pro
                325                 330                 335 ccc gtg ctg gac tcc gac ggc tcc ttc ttc ctc tat agc aag ctc acc     1056
Pro Val Leu Asp Ser Asp Gly Ser Phe Phe Leu Tyr Ser Lys Leu Thr
            340                 345                 350 gtg gac aag agc agg tgg cag cag ggg aac gtc ttc tca tgc tcc gtg     1104
Val Asp Lys Ser Arg Trp Gln Gln Gly Asn Val Phe Ser Cys Ser Val
        355                 360                 365 atg cat gag gct ctg cac aac cac tac acg cag aag agc ctc tcc ctg     1152
Met His Glu Ala Leu His Asn His Tyr Thr Gln Lys Ser Leu Ser Leu
    370                 375                 380 tct ccg ggt aaa tga                                                  1167
Ser Pro Gly Lys
385

<210> SEQ ID NO 6
<211> LENGTH: 388
<212> TYPE: PRT
<213> ORGANISM: Artificial
<220> FEATURE:
<223> OTHER INFORMATION: Synthetic Construct

<400> SEQUENCE: 6

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Pro Cys Lys Ile Leu Lys Cys Asn Ser Glu Phe Trp Ser Ala
        35                  40                  45

Thr Ser Gly Ser His Ala Pro Ala Ser Asp Asp Thr Pro Glu Phe Cys
    50                  55                  60

Ala Ala Leu Arg Ser Tyr Ala Leu Cys Thr Arg Arg Thr Ala Arg Thr
65                  70                  75                  80

Cys Arg Gly Asp Leu Ala Tyr His Ser Ala Val His Gly Ile Glu Asp
                85                  90                  95

Leu Met Ser Gln His Asn Cys Ser Lys Asp Gly Pro Thr Ser Gln Pro
            100                 105                 110

Arg Leu Arg Thr Leu Pro Pro Ala Gly Asp Ser Gln Glu Arg Ser Asp
        115                 120                 125

Ser Pro Glu Ile Cys His Tyr Glu Lys Ser Phe His Lys His Ser Ala
    130                 135                 140

Thr Pro Asn Tyr Thr His Cys Gly Leu Phe Gly Asp Leu Asn Ser Ala
145                 150                 155                 160

Asp Ile Glu Gly Arg Met Asp Pro Pro Cys Pro Ala Pro Glu Leu Leu
```

```
                        165                 170                 175
Gly Gly Pro Ser Val Phe Leu Phe Pro Pro Lys Pro Lys Asp Thr Leu
                180                 185                 190

Met Ile Ser Arg Thr Pro Glu Val Thr Cys Val Val Val Asp Val Ser
            195                 200                 205

His Glu Asp Pro Glu Val Lys Phe Asn Trp Tyr Val Asp Gly Val Glu
        210                 215                 220

Val His Asn Ala Lys Thr Lys Pro Arg Glu Glu Gln Tyr Asn Ser Thr
225                 230                 235                 240

Tyr Arg Val Val Ser Val Leu Thr Val Leu His Gln Asp Trp Leu Asn
                245                 250                 255

Gly Lys Glu Tyr Lys Cys Lys Val Ser Asn Lys Ala Leu Pro Ala Pro
            260                 265                 270

Ile Glu Lys Thr Ile Ser Lys Ala Lys Gly Gln Pro Arg Glu Pro Gln
        275                 280                 285

Val Tyr Thr Leu Pro Pro Ser Arg Glu Glu Met Thr Lys Asn Gln Val
    290                 295                 300

Ser Leu Thr Cys Leu Val Lys Gly Phe Tyr Pro Ser Asp Ile Ala Val
305                 310                 315                 320

Glu Trp Glu Ser Asn Gly Gln Pro Glu Asn Asn Tyr Lys Thr Thr Pro
                325                 330                 335

Pro Val Leu Asp Ser Asp Gly Ser Phe Phe Leu Tyr Ser Lys Leu Thr
            340                 345                 350

Val Asp Lys Ser Arg Trp Gln Gln Gly Asn Val Phe Ser Cys Ser Val
        355                 360                 365

Met His Glu Ala Leu His Asn His Tyr Thr Gln Lys Ser Leu Ser Leu
    370                 375                 380

Ser Pro Gly Lys
385

<210> SEQ ID NO 7
<211> LENGTH: 1431
<212> TYPE: DNA
<213> ORGANISM: Rattus sp.
<220> FEATURE:
<221> NAME/KEY: CDS
<222> LOCATION: (1)..(1431)

<400> SEQUENCE: 7 atg gag aca gac aca ctc ctg cta tgg gta ctg ctg ctc tgg gtt cca        48
Met Glu Thr Asp Thr Leu Leu Leu Trp Val Leu Leu Leu Trp Val Pro
1               5                   10                  15 ggt tcc act ggt gac gcg gcc cag ccg gcc agg cgc gcg cgc cgt acg        96
Gly Ser Thr Gly Asp Ala Ala Gln Pro Ala Arg Arg Ala Arg Arg Thr
            20                  25                  30 aag ctt ggt acc gag ctc gga tcc act agt cca gtg tgg tgg aat tct       144
Lys Leu Gly Thr Glu Leu Gly Ser Thr Ser Pro Val Trp Trp Asn Ser
        35                  40                  45 gca gat atc aca agt ttg tac aaa aaa gca ggc tcc ccg tgc aag atc       192
Ala Asp Ile Thr Ser Leu Tyr Lys Lys Ala Gly Ser Pro Cys Lys Ile
    50                  55                  60 ctc aag tgc aac tct gag ttc tgg agc gcc acg tcg tca ggc agc cac       240
Leu Lys Cys Asn Ser Glu Phe Trp Ser Ala Thr Ser Ser Gly Ser His
65                  70                  75                  80 gcc cct gcc tct gac gac gtg ccc gag ttc tgt gct gcc ctg cgc acc       288
Ala Pro Ala Ser Asp Asp Val Pro Glu Phe Cys Ala Ala Leu Arg Thr
                85                  90                  95
```

-continued

| | |
|---|---|
| tac gcc ctg tgc acg cga cgg aca gcc cgc acc tgc cgg ggc gac ctg<br>Tyr Ala Leu Cys Thr Arg Arg Thr Ala Arg Thr Cys Arg Gly Asp Leu<br>            100                  105                  110 | 336 |
| gct tac cac tcg gct gtc cat ggc ata gag gac ctc atg agc cag cac<br>Ala Tyr His Ser Ala Val His Gly Ile Glu Asp Leu Met Ser Gln His<br>    115                  120                  125 | 384 |
| aac tgc tcc aag gat ggc ccc acc tca cag cct cga gtg cgc acg ctc<br>Asn Cys Ser Lys Asp Gly Pro Thr Ser Gln Pro Arg Val Arg Thr Leu<br>130                  135                  140 | 432 |
| ccg cca gct ggg gac agc cag gag cgc tca gat agc ccc gag atc tgc<br>Pro Pro Ala Gly Asp Ser Gln Glu Arg Ser Asp Ser Pro Glu Ile Cys<br>145                  150                  155                  160 | 480 |
| cac tat gag aag agt ttc cac aag cac tca gct gcc ccc aac tac act<br>His Tyr Glu Lys Ser Phe His Lys His Ser Ala Ala Pro Asn Tyr Thr<br>                  165                  170                  175 | 528 |
| cac tgc ggc ctc ttt ggg gac cca cac ctc agg act ttc aca gac cac<br>His Cys Gly Leu Phe Gly Asp Pro His Leu Arg Thr Phe Thr Asp His<br>                  180                  185                  190 | 576 |
| ttc cag aca tgt aag gtg caa ggc gct tgg cct ctc atc gac aat aat<br>Phe Gln Thr Cys Lys Val Gln Gly Ala Trp Pro Leu Ile Asp Asn Asn<br>            195                  200                  205 | 624 |
| tac ctg aac gtg cag gtc acc aat aca cct gtg ctg ccc ggc tct gcc<br>Tyr Leu Asn Val Gln Val Thr Asn Thr Pro Val Leu Pro Gly Ser Ala<br>210                  215                  220 | 672 |
| gcc act gcc acc agc aag ctc acc atc atc ttc aag aac ttc caa gag<br>Ala Thr Ala Thr Ser Lys Leu Thr Ile Ile Phe Lys Asn Phe Gln Glu<br>225                  230                  235                  240 | 720 |
| tgt gtg gac cag aaa gta tac caa gcc gag atg gac gag ctt ccg tcc<br>Cys Val Asp Gln Lys Val Tyr Gln Ala Glu Met Asp Glu Leu Pro Ser<br>                  245                  250                  255 | 768 |
| gcc ttt gcc gat ggc tcc aaa aac ggt gga gat aaa cac gga gcc aac<br>Ala Phe Ala Asp Gly Ser Lys Asn Gly Gly Asp Lys His Gly Ala Asn<br>                  260                  265                  270 | 816 |
| agc ctg aag atc aca gag aag gtg tca ggc cag cac gtg gag atc cag<br>Ser Leu Lys Ile Thr Glu Lys Val Ser Gly Gln His Val Glu Ile Gln<br>            275                  280                  285 | 864 |
| gcc aag tac atc ggc acc acc atc gtg gtg aga cag gtg ggc cgc tac<br>Ala Lys Tyr Ile Gly Thr Thr Ile Val Val Arg Gln Val Gly Arg Tyr<br>290                  295                  300 | 912 |
| ctg acc ttc gcc gtc cgg atg ccc gag gag gta gtc aac gcc gtg gag<br>Leu Thr Phe Ala Val Arg Met Pro Glu Glu Val Val Asn Ala Val Glu<br>305                  310                  315                  320 | 960 |
| gac cgt gac agc caa ggc ctc tac ctc tgc ctg cgg ggc tgc ccg ctc<br>Asp Arg Asp Ser Gln Gly Leu Tyr Leu Cys Leu Arg Gly Cys Pro Leu<br>                  325                  330                  335 | 1008 |
| aac cag cag atc gac ttc cag gct ttc cgt gcc aac gcc gag agc cct<br>Asn Gln Gln Ile Asp Phe Gln Ala Phe Arg Ala Asn Ala Glu Ser Pro<br>              340                  345                  350 | 1056 |
| cgc agg cca gca gct gcc agc ccc tct cct gtg gtc ccc gag aca ttt<br>Arg Arg Pro Ala Ala Ala Ser Pro Ser Pro Val Val Pro Glu Thr Phe<br>            355                  360                  365 | 1104 |
| ccg tac gag aca gct gtg gcc aag tgc aaa gag aag ctg cct gta gaa<br>Pro Tyr Glu Thr Ala Val Ala Lys Cys Lys Glu Lys Leu Pro Val Glu<br>370                  375                  380 | 1152 |
| gac ttg tac tac cag gcc tgt gtc ttc gac ctc ctc acg act ggc gac<br>Asp Leu Tyr Tyr Gln Ala Cys Val Phe Asp Leu Leu Thr Thr Gly Asp<br>385                  390                  395                  400 | 1200 |
| gtg aac ttc acg ctg gcc gcc tac tat gct ttg gag gat ggc aag atg<br>Val Asn Phe Thr Leu Ala Ala Tyr Tyr Ala Leu Glu Asp Gly Lys Met<br>                  405                  410                  415 | 1248 |

-continued

```
ctc cac tcc aac aag gac aag cta cac ctg ttt gaa agg act cgg gag      1296
Leu His Ser Asn Lys Asp Lys Leu His Leu Phe Glu Arg Thr Arg Glu
        420                 425                 430 ctg cct gac cca gct ttc ttg tac aaa gtg gtg ata tcc agc aca gtg      1344
Leu Pro Asp Pro Ala Phe Leu Tyr Lys Val Val Ile Ser Ser Thr Val
435                 440                 445 gcg gcc gct cga gga ggg ccc gaa caa aaa ctc atc tca gaa gag gat      1392
Ala Ala Ala Arg Gly Gly Pro Glu Gln Lys Leu Ile Ser Glu Glu Asp
    450                 455                 460 ctg aat agc gcc gtc gac cat cat cat cat cat cat tga                  1431
Leu Asn Ser Ala Val Asp His His His His His His
465                 470                 475

<210> SEQ ID NO 8
<211> LENGTH: 476
<212> TYPE: PRT
<213> ORGANISM: Rattus sp.

<400> SEQUENCE: 8

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Lys Leu Gly Thr Glu Leu Gly Ser Thr Ser Pro Val Trp Trp Asn Ser
        35                  40                  45

Ala Asp Ile Thr Ser Leu Tyr Lys Lys Ala Gly Ser Pro Cys Lys Ile
    50                  55                  60

Leu Lys Cys Asn Ser Glu Phe Trp Ser Ala Thr Ser Ser Gly Ser His
65                  70                  75                  80

Ala Pro Ala Ser Asp Asp Val Pro Glu Phe Cys Ala Ala Leu Arg Thr
                85                  90                  95

Tyr Ala Leu Cys Thr Arg Arg Thr Ala Arg Thr Cys Arg Gly Asp Leu
            100                 105                 110

Ala Tyr His Ser Ala Val His Gly Ile Glu Asp Leu Met Ser Gln His
        115                 120                 125

Asn Cys Ser Lys Asp Gly Pro Thr Ser Gln Pro Arg Val Arg Thr Leu
    130                 135                 140

Pro Pro Ala Gly Asp Ser Gln Glu Arg Ser Asp Ser Pro Glu Ile Cys
145                 150                 155                 160

His Tyr Glu Lys Ser Phe His Lys His Ser Ala Ala Pro Asn Tyr Thr
                165                 170                 175

His Cys Gly Leu Phe Gly Asp Pro His Leu Arg Thr Phe Thr Asp His
            180                 185                 190

Phe Gln Thr Cys Lys Val Gln Gly Ala Trp Pro Leu Ile Asp Asn Asn
        195                 200                 205

Tyr Leu Asn Val Gln Val Thr Asn Thr Pro Val Leu Pro Gly Ser Ala
    210                 215                 220

Ala Thr Ala Thr Ser Lys Leu Thr Ile Ile Phe Lys Asn Phe Gln Glu
225                 230                 235                 240

Cys Val Asp Gln Lys Val Tyr Gln Ala Glu Met Asp Glu Leu Pro Ser
                245                 250                 255

Ala Phe Ala Asp Gly Ser Lys Asn Gly Gly Asp Lys His Gly Ala Asn
            260                 265                 270

Ser Leu Lys Ile Thr Glu Lys Val Ser Gly Gln His Val Glu Ile Gln
        275                 280                 285
```

```
Ala Lys Tyr Ile Gly Thr Thr Ile Val Val Arg Gln Val Gly Arg Tyr
    290             295                 300
Leu Thr Phe Ala Val Arg Met Pro Glu Glu Val Val Asn Ala Val Glu
305                 310                 315                 320
Asp Arg Asp Ser Gln Gly Leu Tyr Leu Cys Leu Arg Gly Cys Pro Leu
                325                 330                 335
Asn Gln Gln Ile Asp Phe Gln Ala Phe Arg Ala Asn Ala Glu Ser Pro
                340                 345                 350
Arg Arg Pro Ala Ala Ser Pro Ser Pro Val Val Pro Glu Thr Phe
                355                 360                 365
Pro Tyr Glu Thr Ala Val Ala Lys Cys Lys Glu Lys Leu Pro Val Glu
370                 375                 380
Asp Leu Tyr Tyr Gln Ala Cys Val Phe Asp Leu Leu Thr Thr Gly Asp
385                 390                 395                 400
Val Asn Phe Thr Leu Ala Ala Tyr Tyr Ala Leu Glu Asp Gly Lys Met
                405                 410                 415
Leu His Ser Asn Lys Asp Lys Leu His Leu Phe Glu Arg Thr Arg Glu
                420                 425                 430
Leu Pro Asp Pro Ala Phe Leu Tyr Lys Val Val Ile Ser Ser Thr Val
                435                 440                 445
Ala Ala Ala Arg Gly Gly Pro Glu Gln Lys Leu Ile Ser Glu Glu Asp
                450                 455                 460
Leu Asn Ser Ala Val Asp His His His His His
465                 470                 475

<210> SEQ ID NO 9
<211> LENGTH: 115
<212> TYPE: PRT
<213> ORGANISM: Artificial
<220> FEATURE:
<223> OTHER INFORMATION: VH 5F9
<220> FEATURE:
<221> NAME/KEY: misc_feature
<222> LOCATION: (62)..(62)
<223> OTHER INFORMATION: Xaa can be any naturally occurring amino acid

<400> SEQUENCE: 9

Glu Val Gln Leu Val Glu Ser Gly Gly Gly Leu Val Gln Pro Gly Ser
1               5                   10                  15
Ser Leu Lys Leu Ser Cys Val Ala Ser Gly Phe Thr Phe Ser Asn Tyr
                20                  25                  30
Gly Met Asn Trp Ile Arg Gln Ala Pro Lys Lys Gly Leu Glu Trp Ile
            35                  40                  45
Gly Met Ile Tyr Tyr Asp Ser Ser Glu Lys His Tyr Ala Xaa Ser Val
        50                  55                  60
Lys Gly Arg Phe Thr Ile Ser Arg Asp Asn Ser Lys Asn Thr Leu Tyr
65                  70                  75                  80
Leu Glu Met Asn Ser Leu Arg Ser Glu Asp Thr Ala Ile Tyr Tyr Cys
                85                  90                  95
Ala Lys Gly Thr Thr Pro Asp Tyr Trp Gly Gln Gly Val Met Val Thr
                100                 105                 110
Val Ser Ser
        115

<210> SEQ ID NO 10
<211> LENGTH: 113
<212> TYPE: PRT
<213> ORGANISM: Artificial
```

```
<220> FEATURE:
<223> OTHER INFORMATION: VL 5F9

<400> SEQUENCE: 10

Asp Val Val Leu Thr Gln Thr Pro Val Ser Leu Ser Val Thr Leu Gly
1               5                   10                  15

Asp Gln Ala Ser Met Ser Cys Arg Ser Ser Gln Ser Leu Glu Tyr Ser
            20                  25                  30

Asp Gly Tyr Thr Phe Leu Glu Trp Phe Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Pro Glu Asp Leu Gly Val Tyr Tyr Cys Phe Gln Ala
                85                  90                  95

Thr His Asp Pro Leu Thr Phe Gly Ser Gly Thr Lys Leu Glu Ile Lys
            100                 105                 110

Arg

<210> SEQ ID NO 11
<211> LENGTH: 330
<212> TYPE: PRT
<213> ORGANISM: Artificial
<220> FEATURE:
<223> OTHER INFORMATION: Ig gamma-1 constant region

<400> SEQUENCE: 11

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 12
<211> LENGTH: 330
<212> TYPE: PRT
<213> ORGANISM: Artificial
<220> FEATURE:
<223> OTHER INFORMATION: Ig gamma-1 constant region mutant

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 106
<212> TYPE: PRT
<213> ORGANISM: Artificial
<220> FEATURE:
<223> OTHER INFORMATION: Ig Kappa constant region

<400> SEQUENCE: 13

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 14
<211> LENGTH: 105
<212> TYPE: PRT
<213> ORGANISM: Artificial
<220> FEATURE:
<223> OTHER INFORMATION: lg Lambda constant region

<400> SEQUENCE: 14

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

```
<210> SEQ ID NO 15
<211> LENGTH: 30
<212> TYPE: PRT
<213> ORGANISM: Artificial
<220> FEATURE:
<223> OTHER INFORMATION: VH3-48/JH3 FR1

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 16
<211> LENGTH: 14
<212> TYPE: PRT
<213> ORGANISM: Artificial
<220> FEATURE:
<223> OTHER INFORMATION: VH3-48/JH3 FR2

<400> SEQUENCE: 16

Trp Val Arg Gln Ala Pro Gly Lys Gly Leu Glu Trp Val Ser
1               5                   10

<210> SEQ ID NO 17
<211> LENGTH: 32
<212> TYPE: PRT
<213> ORGANISM: Artificial
<220> FEATURE:
<223> OTHER INFORMATION: VH3-48/JH3 FR3

<400> SEQUENCE: 17

Arg Phe Thr Ile Ser Arg Asp Asn Ala Lys Asn Ser Leu Tyr Leu Gln
1               5                   10                  15

Met Asn Ser Leu Arg Asp Glu Asp Thr Ala Val Tyr Tyr Cys Ala Arg
            20                  25                  30

<210> SEQ ID NO 18
<211> LENGTH: 11
<212> TYPE: PRT
<213> ORGANISM: Artificial
<220> FEATURE:
<223> OTHER INFORMATION: VH3-49/JH3 FR4

<400> SEQUENCE: 18

Trp Gly Gln Gly Thr Met Val Thr Val Ser Ser
1               5                   10

<210> SEQ ID NO 19
<211> LENGTH: 11
<212> TYPE: PRT
<213> ORGANISM: Artificial
<220> FEATURE:
<223> OTHER INFORMATION: VH3-48/JH4 FR4

<400> SEQUENCE: 19

Trp Gly Gln Gly Thr Leu Val Thr Val Ser Ser
1               5                   10

<210> SEQ ID NO 20
<211> LENGTH: 11
<212> TYPE: PRT
<213> ORGANISM: Artificial
<220> FEATURE:
<223> OTHER INFORMATION: VH3-48/JH6 FR4

<400> SEQUENCE: 20
```

```
Trp Gly Gln Gly Thr Thr Val Thr Val Ser Ser
1               5                   10

<210> SEQ ID NO 21
<211> LENGTH: 30
<212> TYPE: PRT
<213> ORGANISM: Artificial
<220> FEATURE:
<223> OTHER INFORMATION: VH3-33/JH6 FR

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 22
<211> LENGTH: 14
<212> TYPE: PRT
<213> ORGANISM: Artificial
<220> FEATURE:
<223> OTHER INFORMATION: VH3-33/JH6 FR2

<400> SEQUENCE: 22

Trp Val Arg Gln Ala Pro Gly Lys Gly Leu Glu Trp Val Ala
1               5                   10

<210> SEQ ID NO 23
<211> LENGTH: 32
<212> TYPE: PRT
<213> ORGANISM: Artificial
<220> FEATURE:
<223> OTHER INFORMATION: VH3-33/JH6 FR3

<400> SEQUENCE: 23

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 24
<211> LENGTH: 30
<212> TYPE: PRT
<213> ORGANISM: Artificial
<220> FEATURE:
<223> OTHER INFORMATION: VH3-23/JH3 FR1

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 25
<211> LENGTH: 14
<212> TYPE: PRT
<213> ORGANISM: Artificial
<220> FEATURE:
<223> OTHER INFORMATION: VH3-23/JH3 FR2

<400> SEQUENCE: 25

Trp Val Arg Gln Ala Pro Gly Lys Gly Leu Glu Trp Val Ser
1               5                   10
```

```
<210> SEQ ID NO 26
<211> LENGTH: 32
<212> TYPE: PRT
<213> ORGANISM: Artificial
<220> FEATURE:
<223> OTHER INFORMATION: VH3-23/JH3 FR3

<400> SEQUENCE: 26

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 27
<211> LENGTH: 23
<212> TYPE: PRT
<213> ORGANISM: Artificial
<220> FEATURE:
<223> OTHER INFORMATION: A18/JK2 FR1

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 28
<211> LENGTH: 15
<212> TYPE: PRT
<213> ORGANISM: Artificial
<220> FEATURE:
<223> OTHER INFORMATION: A18/JK2 FR2

<400> SEQUENCE: 28

Trp Tyr Leu Gln Lys Pro Gly Gln Ser Pro Gln Leu Leu Ile Tyr
1               5                   10                  15

<210> SEQ ID NO 29
<211> LENGTH: 32
<212> TYPE: PRT
<213> ORGANISM: Artificial
<220> FEATURE:
<223> OTHER INFORMATION: A18/JK2 FR3

<400> SEQUENCE: 29

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 30
<211> LENGTH: 11
<212> TYPE: PRT
<213> ORGANISM: Artificial
<220> FEATURE:
<223> OTHER INFORMATION: A18/JK2 FR4

<400> SEQUENCE: 30

Phe Gly Gln Gly Thr Lys Leu Glu Ile Lys Arg
1               5                   10

<210> SEQ ID NO 31
<211> LENGTH: 23
<212> TYPE: PRT
<213> ORGANISM: Artificial
<220> FEATURE:
```

<223> OTHER INFORMATION: A17/JK2 FR1

<400> SEQUENCE: 31

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 32
<211> LENGTH: 15
<212> TYPE: PRT
<213> ORGANISM: Artificial
<220> FEATURE:
<223> OTHER INFORMATION: A17/JK2 FR2

<400> SEQUENCE: 32

Trp Phe Gln Gln Arg Pro Gly Gln Ser Pro Arg Leu Ile Tyr
1               5                   10                  15

<210> SEQ ID NO 33
<211> LENGTH: 32
<212> TYPE: PRT
<213> ORGANISM: Artificial
<220> FEATURE:
<223> OTHER INFORMATION: A17/JK2 FR3

<400> SEQUENCE: 33

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 34
<211> LENGTH: 115
<212> TYPE: PRT
<213> ORGANISM: Artificial
<220> FEATURE:
<223> OTHER INFORMATION: VH 5F9

<400> SEQUENCE: 34

Glu Val Gln Leu Val Glu Ser Gly Gly Gly Leu Val Gln Pro Gly Ser
1               5                   10                  15

Ser Leu Lys Leu Ser Cys Val Ala Ser Gly Phe Thr Phe Ser Asn Tyr
            20                  25                  30

Gly Met Asn Trp Ile Arg Gln Ala Pro Lys Gly Leu Glu Trp Ile
        35                  40                  45

Gly Met Ile Tyr Tyr Asp Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Ile Tyr Tyr Cys
                85                  90                  95

Ala Lys Gly Thr Thr Pro Asp Tyr Trp Gly Gln Gly Val Met Val Thr
            100                 105                 110

Val Ser Ser
        115

<210> SEQ ID NO 35
<211> LENGTH: 115
<212> TYPE: PRT
<213> ORGANISM: Artificial
<220> FEATURE:

<223> OTHER INFORMATION: VH 5F9.1-GL

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Met Ile Tyr Tyr Asp Ser Ser Glu Lys His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Thr Thr Pro Asp Tyr Trp Gly Gln Gly Thr Met Val Thr
            100                 105                 110

Val Ser Ser
        115

<210> SEQ ID NO 36
<211> LENGTH: 115
<212> TYPE: PRT
<213> ORGANISM: Artificial
<220> FEATURE:
<223> OTHER INFORMATION: VH 5F9.2-GL

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Met Ile Tyr Tyr Asp Ser Ser Glu Lys His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Thr Thr Pro Asp Tyr Trp Gly Gln Gly Thr Leu Val Thr
            100                 105                 110

Val Ser Ser
        115

<210> SEQ ID NO 37
<211> LENGTH: 115
<212> TYPE: PRT
<213> ORGANISM: Artificial
<220> FEATURE:
<223> OTHER INFORMATION: VH 5F9.3-GL

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val

```
                35                  40                  45
Ser Met Ile Tyr Tyr Asp Ser Ser Glu Lys His Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Gly Thr Thr Pro Asp Tyr Trp Gly Gln Gly Thr Thr Val Thr
                100                 105                 110

Val Ser Ser
        115

<210> SEQ ID NO 38
<211> LENGTH: 115
<212> TYPE: PRT
<213> ORGANISM: Artificial
<220> FEATURE:
<223> OTHER INFORMATION: VH 5F9.4-GL

<400> SEQUENCE: 38

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
                20                  25                  30

Gly Met Asn Trp Val Arg Gln Ala Pro Gly Lys Gly Leu Glu Trp Val
                35                  40                  45

Ala Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Thr Thr Pro Asp Tyr Trp Gly Gln Gly Thr Met Val Thr
                100                 105                 110

Val Ser Ser
        115

<210> SEQ ID NO 39
<211> LENGTH: 115
<212> TYPE: PRT
<213> ORGANISM: Artificial
<220> FEATURE:
<223> OTHER INFORMATION: VH 5F9.5-GL

<400> SEQUENCE: 39

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
                20                  25                  30

Gly Met Asn Trp Val Arg Gln Ala Pro Gly Lys Gly Leu Glu Trp Val
                35                  40                  45

Ala Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95
```

Ala Arg Gly Thr Thr Pro Asp Tyr Trp Gly Gln Gly Thr Leu Val Thr
            100                 105                 110

Val Ser Ser
        115

<210> SEQ ID NO 40
<211> LENGTH: 115
<212> TYPE: PRT
<213> ORGANISM: Artificial
<220> FEATURE:
<223> OTHER INFORMATION: VH 5F9.6-GL

<400> SEQUENCE: 40

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ala Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Thr Pro Asp Tyr Trp Gly Gln Gly Thr Thr Val Thr
            100                 105                 110

Val Ser Ser
        115

<210> SEQ ID NO 41
<211> LENGTH: 115
<212> TYPE: PRT
<213> ORGANISM: Artificial
<220> FEATURE:
<223> OTHER INFORMATION: VH 5F9.7-GL

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115

<210> SEQ ID NO 42
<211> LENGTH: 115
<212> TYPE: PRT
<213> ORGANISM: Artificial

```
<220> FEATURE:
<223> OTHER INFORMATION: VH 5F9.8-GL

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Leu Val Thr
            100                 105                 110

Val Ser Ser
        115

<210> SEQ ID NO 43
<211> LENGTH: 115
<212> TYPE: PRT
<213> ORGANISM: Artificial
<220> FEATURE:
<223> OTHER INFORMATION: VH 5F9.9-GL

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Leu Val Thr
            100                 105                 110

Val Ser Ser
        115

<210> SEQ ID NO 44
<211> LENGTH: 113
<212> TYPE: PRT
<213> ORGANISM: Artificial
<220> FEATURE:
<223> OTHER INFORMATION: VL 5F9.1-GL

<400> SEQUENCE: 44

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Glu Tyr Ser
            20                  25                  30
```

Asp Gly Tyr Thr Phe Leu Glu Trp Tyr Leu Gln Lys Pro Gly Gln Ser
            35                  40                  45

Pro Gln Leu Leu Ile Tyr Glu Val Ser Asn Arg Phe Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ala
                 85                  90                  95

Thr His Asp Pro Leu Thr Phe Gly Gln Gly Thr Lys Leu Glu Ile Lys
                100                 105                 110

Arg

<210> SEQ ID NO 45
<211> LENGTH: 113
<212> TYPE: PRT
<213> ORGANISM: Artificial
<220> FEATURE:
<223> OTHER INFORMATION: VL 5F9.2-GL

<400> SEQUENCE: 45

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Glu Tyr Ser
             20                  25                  30

Asp Gly Tyr Thr Phe Leu Glu Trp Phe Gln Gln Arg Pro Gly Gln Ser
            35                  40                  45

Pro Arg Arg Leu Ile Tyr Glu Val Ser Asn Arg Phe Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ala
                 85                  90                  95

Thr His Asp Pro Leu Thr Phe Gly Gln Gly Thr Lys Leu Glu Ile Lys
                100                 105                 110

Arg

<210> SEQ ID NO 46
<211> LENGTH: 113
<212> TYPE: PRT
<213> ORGANISM: Artificial
<220> FEATURE:
<223> OTHER INFORMATION: VL 5F9.3-GL

<400> SEQUENCE: 46

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Glu Tyr Ser
             20                  25                  30

Asp Gly Tyr Thr Phe Leu Glu Trp Tyr Leu Gln Lys Pro Gly Gln Ser
            35                  40                  45

Pro Gln Leu Leu Ile Tyr Glu Val Ser Asn Arg Phe Ser Gly Val Pro
 50                      55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Ala
                 85                  90                  95

Thr His Asp Pro Leu Thr Phe Gly Gln Gly Thr Lys Leu Glu Ile Lys

-continued

Arg

<210> SEQ ID NO 47
<211> LENGTH: 115
<212> TYPE: PRT
<213> ORGANISM: Artificial
<220> FEATURE:
<223> OTHER INFORMATION: VH h5F9.1

<400> SEQUENCE: 47

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ala Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Thr Pro Asp Tyr Trp Gly Gln Gly Thr Met Val Thr
            100                 105                 110

Val Ser Ser
        115

<210> SEQ ID NO 48
<211> LENGTH: 115
<212> TYPE: PRT
<213> ORGANISM: Artificial
<220> FEATURE:
<223> OTHER INFORMATION: VH h5F9.2

<400> SEQUENCE: 48

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
        35                  40                  45

Gly Met Ile Tyr Tyr Asp Ser Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115

<210> SEQ ID NO 49
<211> LENGTH: 115
<212> TYPE: PRT
<213> ORGANISM: Artificial
<220> FEATURE:
<223> OTHER INFORMATION: VH h5F9.3

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Val Arg Gln Ala Pro Gly Lys Gly Leu Glu Trp Val
        35                  40                  45

Ser Met Ile Tyr Tyr Asp Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115

<210> SEQ ID NO 50
<211> LENGTH: 115
<212> TYPE: PRT
<213> ORGANISM: Artificial
<220> FEATURE:
<223> OTHER INFORMATION: VH h5F9.4

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Asn Trp Ile Arg Gln Ala Pro Gly Lys Gly Leu Glu Trp Ile
        35                  40                  45

Gly Met Ile Tyr Tyr Asp Ser Glu Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Thr Pro Asp Tyr Trp Gly Gln Gly Thr Met Val Thr
            100                 105                 110

Val Ser Ser
        115

<210> SEQ ID NO 51
<211> LENGTH: 113
<212> TYPE: PRT
<213> ORGANISM: Artificial
<220> FEATURE:
<223> OTHER INFORMATION: VL h5F9.19

<400> SEQUENCE: 51

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Tyr Ser
            20                  25                  30

Asp Gly Tyr Thr Phe Leu Glu Trp Phe Gln Gln Arg Pro Gly Gln Ser
        35                  40                  45

```
Pro Arg Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
                100                 105                 110

Arg
```

<210> SEQ ID NO 52
<211> LENGTH: 113
<212> TYPE: PRT
<213> ORGANISM: Artificial
<220> FEATURE:
<223> OTHER INFORMATION: VL h5F9.20

<400> SEQUENCE: 52

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Tyr Ser
                20                  25                  30

Asp Gly Tyr Thr Phe Leu Glu Trp Phe Gln Gln Arg Pro Gly Gln Ser
            35                  40                  45

Pro Arg Arg Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
                100                 105                 110

Arg
```

<210> SEQ ID NO 53
<211> LENGTH: 113
<212> TYPE: PRT
<213> ORGANISM: Artificial
<220> FEATURE:
<223> OTHER INFORMATION: VL h5F9.21

<400> SEQUENCE: 53

```
Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Tyr Ser
                20                  25                  30

Asp Gly Tyr Thr Phe Leu Glu Trp Phe Leu Gln Lys Pro Gly Gln Ser
            35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
                100                 105                 110
```

Arg

<210> SEQ ID NO 54
<211> LENGTH: 113
<212> TYPE: PRT
<213> ORGANISM: Artificial
<220> FEATURE:
<223> OTHER INFORMATION: VL h5F9.22

<400> SEQUENCE: 54

Asp Val Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Glu Tyr Ser
            20                  25                  30

Asp Gly Tyr Thr Phe Leu Glu Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Thr His Asp Pro Leu Thr Phe Gly Gln Gly Thr Lys Leu Glu Ile Lys
            100                 105                 110

Arg

<210> SEQ ID NO 55
<211> LENGTH: 121
<212> TYPE: PRT
<213> ORGANISM: Artificial
<220> FEATURE:
<223> OTHER INFORMATION: VH 8D1

<400> SEQUENCE: 55

Glu Val Gln Leu Gln Gln Ser Gly Pro Glu Leu Val Lys Pro Gly Thr
1               5                   10                  15

Ser Val Lys Met Ser Cys Lys Thr Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Asn Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Arg Asn Glu Tyr Tyr Gly Ser Ser Phe Phe Asp Tyr Trp Gly
            100                 105                 110

Gln Gly Thr Thr Leu Thr Val Ser Ser
        115                 120

<210> SEQ ID NO 56
<211> LENGTH: 108
<212> TYPE: PRT
<213> ORGANISM: Artificial
<220> FEATURE:
<223> OTHER INFORMATION: VL 8D1

<400> SEQUENCE: 56

```
Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Asp Asn Tyr
            20                  25                  30

Leu Ala Trp Tyr His Gln Lys Pro Gly Lys Ser Pro Arg Leu Leu Ile
        35                  40                  45

Tyr Gly Ala Thr Asn Leu Ala Asp Gly Val Pro Ser Arg Phe Ser Gly
    50                  55                  60

Ser Arg Ser Gly Thr Gln Phe Ser Leu Lys Ile Asn Arg Leu Gln Ile
65                  70                  75                  80

Glu Asp Leu Gly Ile Tyr Tyr Cys Leu Gln Gly Tyr Ile Pro Pro Arg
                85                  90                  95

Thr Phe Gly Gly Gly Thr Lys Leu Glu Leu Lys Arg
            100                 105
```

```
<210> SEQ ID NO 57
<211> LENGTH: 5
<212> TYPE: PRT
<213> ORGANISM: Artificial
<220> FEATURE:
<223> OTHER INFORMATION: VH 5F9 CDR H1

<400> SEQUENCE: 57

Asn Tyr Gly Met Asn
1               5
```

```
<210> SEQ ID NO 58
<211> LENGTH: 17
<212> TYPE: PRT
<213> ORGANISM: Artificial
<220> FEATURE:
<223> OTHER INFORMATION: VH 5F9 CDR-H2

<400> SEQUENCE: 58

Met Ile Tyr Tyr Asp Ser Ser Glu Lys His Tyr Ala Asp Ser Val Lys
1               5                   10                  15

Gly
```

```
<210> SEQ ID NO 59
<211> LENGTH: 6
<212> TYPE: PRT
<213> ORGANISM: Artificial
<220> FEATURE:
<223> OTHER INFORMATION: VH 5F9 CDR-H3

<400> SEQUENCE: 59

Gly Thr Thr Pro Asp Tyr
1               5
```

```
<210> SEQ ID NO 60
<211> LENGTH: 16
<212> TYPE: PRT
<213> ORGANISM: Artificial
<220> FEATURE:
<223> OTHER INFORMATION: VL 5F9 CDR-L1

<400> SEQUENCE: 60

Arg Ser Ser Gln Ser Leu Glu Tyr Ser Asp Gly Tyr Thr Phe Leu Glu
1               5                   10                  15
```

```
<210> SEQ ID NO 61
<211> LENGTH: 7
<212> TYPE: PRT
```

```
<213> ORGANISM: Artificial
<220> FEATURE:
<223> OTHER INFORMATION: VL 5F9 CDR-L2

<400> SEQUENCE: 61

Glu Val Ser Asn Arg Phe Ser
1               5

<210> SEQ ID NO 62
<211> LENGTH: 9
<212> TYPE: PRT
<213> ORGANISM: Artificial
<220> FEATURE:
<223> OTHER INFORMATION: VL 5F9 CDR-L3

<400> SEQUENCE: 62

Phe Gln Ala Thr His Asp Pro Leu Thr
1               5

<210> SEQ ID NO 63
<211> LENGTH: 5
<212> TYPE: PRT
<213> ORGANISM: Artificial
<220> FEATURE:
<223> OTHER INFORMATION: VH 8D1 CDR-H1

<400> SEQUENCE: 63

Ser Tyr Val Met His
1               5

<210> SEQ ID NO 64
<211> LENGTH: 17
<212> TYPE: PRT
<213> ORGANISM: Artificial
<220> FEATURE:
<223> OTHER INFORMATION: VH 8D1 CDR-H2

<400> SEQUENCE: 64

Tyr Ile Ile Pro Tyr Asn Asp Asn Thr Lys Tyr Asn Glu Lys Phe Lys
1               5                   10                  15

Gly

<210> SEQ ID NO 65
<211> LENGTH: 14
<212> TYPE: PRT
<213> ORGANISM: Artificial
<220> FEATURE:
<223> OTHER INFORMATION: VH 8D1 CDR-H3

<400> SEQUENCE: 65

Ala Arg Arg Asn Glu Tyr Tyr Gly Ser Ser Phe Phe Asp Tyr
1               5                   10

<210> SEQ ID NO 66
<211> LENGTH: 11
<212> TYPE: PRT
<213> ORGANISM: Artificial
<220> FEATURE:
<223> OTHER INFORMATION: VL 8D1 CDR-L1

<400> SEQUENCE: 66

Gln Ala Ser Gln Asp Ile Asp Asn Tyr Leu Ala
1               5                   10

<210> SEQ ID NO 67
<211> LENGTH: 7
```

```
<212> TYPE: PRT
<213> ORGANISM: Artificial
<220> FEATURE:
<223> OTHER INFORMATION: VL 8D1 CDR-L2

<400> SEQUENCE: 67

Gly Ala Thr Asn Leu Ala Asp
1               5

<210> SEQ ID NO 68
<211> LENGTH: 9
<212> TYPE: PRT
<213> ORGANISM: Artificial
<220> FEATURE:
<223> OTHER INFORMATION: VL 8D1 CDR-L3

<400> SEQUENCE: 68

Leu Gln Gly Tyr Ile Pro Pro Arg Thr
1               5
```